US012061187B2

(12) United States Patent
Birnbaum et al.

(10) Patent No.: US 12,061,187 B2
(45) **Date of Patent: *Aug. 13, 2024**

(54) LIGAND DISCOVERY AND GENE DELIVERY VIA RETROVIRAL SURFACE DISPLAY

(71) Applicant: Massachusetts Institute of Technology, Cambridge, MA (US)

(72) Inventors: Michael Birnbaum, Cambridge, MA (US); Connor Dobson, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1179 days.

This patent is subject to a terminal disclaimer.

(21) Appl. No.: 16/826,665

(22) Filed: Mar. 23, 2020

(65) Prior Publication Data

US 2020/0371088 A1 Nov. 26, 2020

Related U.S. Application Data

(60) Provisional application No. 62/851,889, filed on May 23, 2019.

(51) Int. Cl.

| | |
|---|---|
| ***G01N 33/50*** | (2006.01) |
| ***C07K 14/005*** | (2006.01) |
| ***C07K 14/47*** | (2006.01) |
| ***C07K 14/54*** | (2006.01) |
| ***C07K 14/705*** | (2006.01) |
| ***C07K 14/74*** | (2006.01) |
| ***C07K 16/28*** | (2006.01) |
| ***C12N 15/86*** | (2006.01) |

(52) U.S. Cl.

CPC ......... *G01N 33/505* (2013.01); *C07K 14/005* (2013.01); *C07K 14/4748* (2013.01); *C07K 14/5437* (2013.01); *C07K 14/70532* (2013.01); *C07K 14/70539* (2013.01); *C07K 16/2803* (2013.01); *C12N 15/86* (2013.01); *C07K 2317/622* (2013.01); *C07K 2319/02* (2013.01); *C07K 2319/035* (2013.01); *C07K 2319/60* (2013.01); *C12N 2740/15045* (2013.01)

(58) Field of Classification Search

CPC ............. G01N 33/505; G01N 33/5047; G01N 33/5008; C07K 14/005; C07K 14/4748; C07K 14/5437; C07K 14/70532; C07K 14/70539; C07K 16/2803; C07K 2317/622; C07K 2319/02; C07K 2319/035; C07K 2319/60; C07K 14/47; C12N 15/86; C12N 2740/15045; C12N 2740/16043; C12N 2740/16045; C12N 2810/85; C12N 2810/852; C12N 2810/855; C12N 2810/859; C40B 30/04

See application file for complete search history.

(56) References Cited

U.S. PATENT DOCUMENTS

| | | | | |
|---|---|---|---|---|
| 7,901,671 | B2 | 3/2011 | Leboulch et al. | |
| 9,994,867 | B2 | 6/2018 | Baltimore et al. | |
| 2015/0316511 | A1 | 11/2015 | Guo | |
| 2017/0176435 | A1* | 6/2017 | Seidell, III ....... | C07K 14/70539 |
| 2017/0192011 | A1 | 7/2017 | Birnbaum et al. | |
| 2017/0356010 | A1* | 12/2017 | Frost ...................... | C12N 15/86 |
| 2018/0362966 | A1 | 12/2018 | Flechtner et al. | |
| 2020/0216502 | A1* | 7/2020 | Albertini .................. | C12N 7/00 |

FOREIGN PATENT DOCUMENTS

| | | | | |
|---|---|---|---|---|
| WO | WO 2008/037458 | A2 | 4/2008 | |
| WO | WO 2012/088381 | A2 | 6/2012 | |
| WO | WO 2015/104376 | A1 | 7/2015 | |
| WO | WO 2015/112541 | A2 | 7/2015 | |
| WO | WO 2015/117027 | A1 | 8/2015 | |
| WO | WO 2017/182585 | A1 | 12/2017 | |
| WO | WO 2019/056015 | A2 | 3/2019 | |
| WO | WO 2019/057974 | A1 | 3/2019 | |
| WO | WO-2019057974 | A1 * | 3/2019 | ........... C07K 14/005 |

OTHER PUBLICATIONS

Hastie E, Cataldi M, Marriott I, Grdzelishvili VZ. Understanding and altering cell tropism of vesicular stomatitis virus. Virus Res. Sep. 2013;176(1-2):16-32. Epub Jun. 22, 2013. (Year: 2013).*

Sevier CS, Weisz OA, Davis M, Machamer CE. Efficient export of the vesicular stomatitis virus G protein from the endoplasmic reticulum requires a signal in the cytoplasmic tail that includes both tyrosine-based and di-acidic motifs. Mol Biol Cell. Jan. 2000;11(1):13-22. (Year: 2000).*

Ou W, Marino MP, Suzuki A, Joshi B, Husain SR, Maisner A, Galanis E, Puri RK, Reiser J. Specific targeting of human interleukin (IL)-13 receptor α2-positive cells with lentiviral vectors displaying IL-13. Hum Gene Ther Methods. Apr. 2012;23(2):137-47. Epub May 21, 2012. (Year: 2012).*

Frank AM, Buchholz CJ. Surface-Engineered Lentiviral Vectors for Selective Gene Transfer into Subtypes of Lymphocytes. Mol Ther Methods Clin Dev. Oct. 17, 2018712:19-31. (Year: 2018).*

Cire S, Da Rocha S, Yao R, Fisson S, Buchholz CJ, Collins MK, Galy A. Immunization of mice with lentiviral vectors targeted to MHC class II+ cells is due to preferential transduction of dendritic cells in vivo. PLoS One. Jul. 24, 2014;9(7):e101644. (Year: 2014).*

Zhang N, Huang H, Tan B, Wei Y, Xiong Q, Yan Y, Hou L, Wu N, Siwko S, et al. Leucine-rich repeat-containing G protein-coupled receptor 4 facilitates vesicular stomatitis virus infection by binding vesicular stomatitis virus glycoprotein. J Biol Chem. Oct. 6, 2017;292(40):16527-16538. Epub Aug. 23, 2017. (Year: 2017).*

Bowie Ju, et al. Science. 1990 Mar. 16;247(4948):1306-10. (Year: 1990).*

(Continued)

*Primary Examiner* — Rachel B Gill

(74) *Attorney, Agent, or Firm* — Wolf, Greenfield & Sacks, P.C.

(57) ABSTRACT

Compositions of retroviruses and methods of using the same for gene delivery, wherein the retroviruses comprise a viral envelope protein comprising at least one mutation that diminishes its native function, a non-viral membrane-bound protein comprising a membrane-bound domain and an extra-cellular targeting domain.

20 Claims, 26 Drawing Sheets

Specification includes a Sequence Listing.

(56) References Cited

OTHER PUBLICATIONS

Winkler K, et al. J Immunol. Oct. 15, 2000; 165(8):4505-14. (Year: 2000).*
Kussie PH, et al. J Immunol. Jan. 1, 1994;152(1):146-52. (Year: 1994).*
Chen Z, et al. Nat Commun. Mar. 30, 2015;6:6714. (Year: 2015).*
Sela-Culang I, et al. Front Immunol. Oct. 8, 2013;4:302. (Year: 2013).*
Sirin S, et al. Protein Sci. Feb. 2016;25(2):393-409. Epub Nov. 6, 2015. (Year: 2015).*
Höfig I, Barth S, Salomon M, Jagusch V, Atkinson MJ, Anastasov N, Thirion C. Systematic improvement of lentivirus transduction protocols by antibody fragments fused to VSV-G as envelope glycoprotein. Biomaterials. Apr. 2014;35(13):4204-12. doi: 10.1016/j.biomaterials.2014.01.051. Epub Feb. 12, 2014. (Year: 2014).*
Dreja H, Piechaczyk M. The effects of N-terminal insertion into VSV-G of an scFv peptide. Virol J. Sep. 2, 2006;3:69. doi: 10.1186/1743-422X-3-69. PMID: 16948856; PMCID: PMC1564393. (Year: 2006).*
Kameyama Y, Kawabe Y, Ito A, Kamihira M. Antibody-dependent gene transduction using gammaretroviral and lentiviral vectors pseudotyped with chimeric vesicular stomatitis virus glycoprotein. J Virol Methods. Oct. 2008;153(1):49-54. doi: 10.1016/j.jviromet.2008.06.013. Epub Jul. 18, 2008. (Year: 2008).*
Yu B, Shi Q, Belk JA, Yost KE, Parker KR, Li R, Liu BB, Huang H, Lingwood D, Greenleaf WJ, Davis MM, Satpathy AT, Chang HY. Engineered cell entry links receptor biology with single-cell genomics. Cell. Dec. 22, 2022;185(26):4904-4920.e22. doi: 10.1016/j.cell.2022.11.016. Epub Dec. 13, 2022. (Year: 2022).*
Nikolic J, Belot L, Raux H, Legrand P, Gaudin Y, A Albertini A. Structural basis for the recognition of LDL-receptor family members by VSV glycoprotein. Nat Commun. Mar. 12, 2018;9(1):1029. doi: 10.1038/s41467-018-03432-4. PMID: 29531262; PMCID: PMC5847621. (Year: 2018).*
Yang H, Joo KI, Ziegler L, Wang P. Cell type-specific targeting with surface-engineered lentiviral vectors co-displaying OKT3 antibody and fusogenic molecule. Pharm Res. Jun. 2009;26(6):1432-45. doi: 10.1007/s11095-009-9853-y. Epub Mar. 4, 2009. PMID: 19259792; PMCID: PMC2798122. (Year: 2009).*
Frank AM, Buchholz CJ. Surface-Engineered Lentiviral Vectors for Selective Gene Transfer into Subtypes of Lymphocytes. Mol Ther Methods Clin Dev. Oct. 17, 2018; 12:19-31. doi: 10.1016/j.omtm.2018.10.006. PMID: 30417026; PMCID: PMC6216101. (Year: 2018).*
Milani M, Annoni A, Bartolaccini S, Biffi M, Russo F, Di Tomaso T, Raimondi A, Lengler J, Holmes MC, Scheiflinger F, Lombardo A, Cantore A, Naldini L. Genome editing for scalable production of alloantigen-free lentiviral vectors for in vivo gene therapy. EMBO Mol Med. Nov. 2017;9(11):1558-1573. (Year: 2017).*
Bentzen et al., Evolution of MHC-based technologies used for detection of antigen-responsive T cells. Cancer Immunol Immunother. Mar. 17, 2017;66:657-66.
Funke et al., Targeted Cell Entry of Lentiviral Vectors. Mol Ther. Aug. 2008;16(8):1427-36.
Grubaugh et al., Proteins as T cell antigens: methods for high-throughput identification. Vaccine. Aug. 20, 2013;31(37).
Guideng et al., T cell antigen discovery via trogocytosis. Nature Methods. Feb. 2019;16(2):183-90.
Joglekar et al., T cell antigen discovery via signaling and antigen-presenting bifunctional receptors. Nature Methods. Sep. 23, 2019;16(2):191-8.
Nikolic et al., Structural basis for the recognition of LDL-receptor family members by VSV glycoprotein. Nat Commun. Mar. 12, 2018;9:1029.
Yang et al., Targeting lentiviral vectors to specific cell types in vivo. PNAS. Aug. 1, 2006;103(31):11479-84.
Singaporean Search Report dated Sep. 15, 2023, for Application No. 11202112344V.
Invitation to Pay Additional Fees mailed Jul. 15, 2020, for Application No. PCT/US2020/024175.
International Search Report and Written Opinion mailed Sep. 14, 2020, for Application No. PCT/US2020/024175.
International Preliminary Report on Patentability mailed Dec. 2, 2021, for Application No. PCT/US2020/024175.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Buchholz et al., Retroviral display and high throughput screening. Comb Chem High Throughput Screen. Feb. 2008;11(2):99-110.
Karlin et al., Methods for assessing the statistical significance of molecular sequence features by using general scoring schemes. Proc Natl Acad Sci U S A. Mar. 1990;87(6):2264-8.
Karlin et al., Applications and statistics for multiple high-scoring segments in molecular sequences. Proc Natl Acad Sci U S A. Jun. 15, 1993;90(12):5873-7.
Taube et al., Lentivirus display: stable expression of human antibodies on the surface of human cells and virus particles. PLoS One. Sep. 11, 2008;3(9):e3181.
Urban et al., Selection of functional human antibodies from retroviral display libraries. Nucleic Acids Res. Feb. 24, 2005;33(4):e35.
Urban et al., Retroviral display in gene therapy, protein engineering, and vaccine development. ACS Chem Biol. Jan. 21, 2011;6(1):61-74. doi: 10.1021/cb100285n. Epub Dec. 20, 2010.
Yang et al., Cell type-specific targeting with surface-engineered lentiviral vectors co-displaying OKT3 antibody and fusogenic molecule. Pharm Res. Jun. 2009;26(6):1432-45. doi: 10.1007/s11095-009-9853-y. Epub Mar. 4, 2009.
Chan et al., Conjugation of lentivirus to paramagnetic particles via nonviral proteins allows efficient concentration and infection of primary acute myeloid leukemia cells. J Virol. Oct. 2005;79(20):13190-4.
Goyvaerts et al., Targeting of human antigen-presenting cell subsets. J Virol. Oct. 2013;87(20):11304-8. doi: 10.1128/JVI.01498-13. Epub Jul. 17, 2013.
Goyvaerts et al., Development of the Nanobody display technology to target lentiviral vectors to antigen-presenting cells. Gene Ther. Dec. 2012;19(12):1133-40. doi: 10.1038/gt.2011.206. Epub Jan. 12, 2012.
Peach et al., Both extracellular immunoglobin-like domains of CD80 contain residues critical for binding T cell surface receptors CTLA-4 and CD28. J Biol Chem. Sep. 8, 1995;270(36):21181-7.
Zhang et al., Cell-specific targeting of lentiviral vectors mediated by fusion proteins derived from Sindbis virus, vesicular stomatitis virus, or avian sarcoma/leukosis virus. Retrovirology. Jan. 25, 2010;7:3.

* cited by examiner

| Sample | % Positive | GFP MFI |
|---|---|---|
| Untransduced | 0 | 1377 |
| 1G4hi (26 pM) | 73.2 | 21890 |
| C5-C100 (5 nM) | 82.3 | 31325 |
| C10-C1 (84 nM) | 84.8 | 26000 |
| 1G4 WT (32 μM) | 51.3 | 10225 |

LIGAND DISCOVERY AND GENE DELIVERY VIA RETROVIRAL SURFACE DISPLAY

RELATED APPLICATION

This application claims the benefit under 35 U.S.C. § 119(e) of the filing date of U.S. Provisional Application Ser. No. 62/851,889, entitled "LIGAND DISCOVERY AND GENE DELIVERY VIA RETROVIRAL SURFACE DISPLAY" and filed on May 23, 2019, the entire contents of which are incorporated herein by reference.

GOVERNMENT SUPPORT

This invention was made with government support under Grant No. P30 CA014051 awarded by the National Institutes of Health (NIH), and Grant No. W81XWH-18-1-0208 awarded by the U.S. Army. The government has certain rights in the invention.

BACKGROUND

It has been well established that retroviruses (e.g., lentiviruses) can have their natural tropism redirected to targets of interest via pseudotyping a virus to express the envelope protein of a different virus. This is most commonly accomplished via pseudotyping with the VSV glycoprotein, which targets the LDL receptor and therefore enables viral entry into a wide range of cells. Recently, groups have shown that if lentiviruses are pseudotyped with envelope proteins from paramyxoviruses such as measles virus or nipah virus, and if mutations are created that abolish native tropism, C-terminal fusions to these viruses allow receptor-mediated entry to the target cell of choice.

SUMMARY

Herein, the inventors have surprisingly demonstrated that a combination of mutations to abolish native function (e.g., tropism) and overexpression of a second membrane protein allows for that second protein to function as the basis for viral entry. These discoveries, as described herein, enable new and innovative methodologies, for example, to screen of cells that are notoriously challenging to screen for specific antigens and function (e.g., T cells), and to deliver nucleic acids to target cells in a target-specific manner.

Some aspects of the disclosure provide compositions of a retrovirus (e.g., a lentivirus) comprising (i) a nucleic acid comprising a non-viral membrane-bound protein comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter; and (ii) a mutated viral envelope protein comprising at least one mutation that diminishes its native function.

Some aspects of the disclosure provide compositions of a retrovirus (e.g., a lentivirus), comprising (i) a CD80 protein domain; and (ii) a mutated viral envelope protein comprising at least one mutation that diminishes its native function. The CD80 protein domain may be an extracellular domain. In some embodiments, the CD80 extracellular domain binds to a receptor on a target cell.

Some aspects of the disclosure provide methods of screening a population of cells, the method comprising (i) providing a retrovirus (e.g., a lentivirus) comprising a viral envelope protein comprising at least one mutation that diminishes its native function, a non-viral membrane-bound protein comprising a membrane-bound domain and an extracellular targeting domain, and a nucleic acid encoding a reporter; (ii) combining the retrovirus with a population of cells; and (iii) sorting the population of cells based on the presence or absence of the reporter. In some embodiments, the retrovirus (e.g., a lentivirus) comprises a nucleic acid comprising a non-viral membrane-bound protein comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter.

In some embodiments, the cells are somatic cells (e.g., antigen-specific cells, e.g., T cells or B cells). In some embodiments, the cells are isolated from a subject (e.g., a human subject). In some embodiments, the cells are isolated from the blood or a tumor of a subject. In some embodiments, the cells are maintained in liquid culture prior to being combined with the retrovirus.

In some embodiments, the viral envelope protein is a VSV-G envelope protein, a measles virus envelope protein, a nipah virus envelope protein, or a cocal virus G protein. A VSV-G envelope protein may be a mutated at one or more of any one of H8, K47, Y209, and/or R354. A measles virus envelope protein may be a mutated at one or more of any one of Y481, R533, S548, and/or F549. A nipah virus envelope protein may be a mutated at one or more of any one of E501, W504, Q530, and/or E533. A cocal virus G protein may be a mutated at K64 and/or R371.

In some embodiments, the non-viral membrane-bound protein comprises a Major Histocompatibility Complex (MHC) protein. In some embodiments, the extracellular targeting domain is a protein (e.g., interleukin-13), a peptide, or an antibody (e.g., anti-CD19 antibody, an anti-TCR antibody, or an anti-CD3 antibody). In some embodiments, the reporter is a fluorescent protein (e.g., green fluorescent protein, yellow fluorescent protein, red fluorescent protein) or an antibiotic resistance marker. In some embodiments, a linker is positioned between the membrane-bound domain and the extracellular targeting domain. A linker may be a rigid linker (e.g., a PDGFR stalk or a CD8a stalk), a flexible linker (e.g., comprising an amino acid sequence comprising GAPGAS (SEQ ID NO: 5) or GGGGS (SEQ ID NO: 7)), or an oligomerized linker (e.g., an IgG4 hinge or an amino acid sequence that can form a tetrameric coiled coil).

In some embodiments, the retrovirus is combined with the population of cells in (ii) for one minute to seventy-two hours and at a temperature ranging from 4° C. to 42° C. In some embodiments, the retrovirus and the population of cells are combined in (ii) in the presence of (a) a cell culture media, optionally RPMI or DMEM cell culture media; (b) a buffered saline solution, optionally phosphate-buffered saline or HEPES-buffered saline; and/or (c) an enhancer of retroviral transduction, optionally heparin sulfate, polybrene, protamine sulfate, and/or dextran. In some embodiments, the extracellular targeting domain is capable of binding to a cognate protein (e.g., a protein receptor) that is present on the cell surface of a subset of the population of cells. In some embodiments, the population of cells is washed between (ii) and (iii) (e.g., using phosphate-buffered saline (PBS), e.g., to remove the retrovirus from the population of cells). In some embodiments, sorting the population of cells is performed using fluorescence-activated cell sorting, single-cell next-generation sequencing, or antibiotic selection.

In some embodiments, the methods further comprise a second retrovirus, wherein the second retrovirus comprises a different extracellular targeting domain and/or a different reporter compared to the first retrovirus.

Other aspects of the disclosure provide methods of delivering a nucleic acid (e.g., a gene of interest, e.g., that encodes a protein) to an cell, the method comprising (i) providing a retrovirus comprising the nucleic acid, a viral envelope protein comprising at least one mutation that diminishes its native function, and a non-viral membrane-bound protein comprising an extracellular targeting domain that is capable of binding to a cognate ligand of the cell; and (ii) contacting the retrovirus with the cell, thereby delivering the nucleic acid to the cell. In some embodiments, the retrovirus enters or infects the cell during (ii).

Some aspects of the disclosure provide methods of delivering a nucleic acid to a cell, the method comprising (i) providing a retrovirus comprising the nucleic acid, a viral envelope protein comprising at least one mutation that diminishes its native function, and a CD80 protein domain; and (ii) contacting the retrovirus with the cell, thereby delivering the nucleic acid to the cell.

Yet other aspects of the disclosure provide methods of detecting an interaction between a retrovirus and an cell, the method comprising: (i) contacting a sample comprising the retrovirus and an cell with an antibody, wherein the retrovirus comprises a viral envelope protein comprising at least one mutation that diminishes its native function, a non-viral membrane-bound protein comprising an extracellular targeting domain, and wherein the antibody binds to the extracellular targeting domain of the retrovirus; (ii) optionally removing unbound antibody from the sample; and (iii) imaging the sample to detect whether the antibody-retrovirus complex is bound to the cell.

In some embodiments, the antibody further comprises a fluorescent label, optionally wherein the antibody is covalently linked to a fluorescent label. In some embodiments, the sample is imaged in (iii) using confocal or fluorescence microscopy.

Some aspects of the disclosure provide libraries of retroviruses, comprising a plurality of unique retroviruses, wherein each unique retrovirus comprises a viral envelope protein comprising at least one mutation that diminishes its native function, a non-viral membrane-bound protein comprising a membrane-bound domain and an extracellular targeting domain (e.g., comprising at least 5, at least 10, at least 15, at least 20, or at least 50 amino acids), and a nucleic acid encoding a reporter, and wherein each unique retrovirus comprises a different and unique extracellular targeting domain.

In some embodiments, a library is capable of being screened against a population of antigen-specific cells, optionally wherein the antigen-specific cells are B cells or T cells. A library may comprise at least $10^2$, at least $10^3$, at least $10^4$, at least $10^5$, at least $10^6$, at least $10^7$, at least $10^8$, at least $10^9$, or at least $10^{10}$ unique retroviruses. In some embodiments, each different and unique extracellular targeting domain is generated through site-directed mutagenesis.

Some aspects of the disclosure provide populations of cells, wherein a subset of the population of cells contain a retrovirus comprising: a viral envelope protein comprising at least one mutation that diminishes its native function, a non-viral membrane-bound protein comprising a membrane-bound domain and an extracellular targeting domain, and a nucleic acid encoding a reporter. In some embodiments, a subset of the population of cells (e.g., antigen-specific cells, e.g., B cells or T cells) contains a retrovirus as described herein. In some embodiments, the subset of the population of cells contains a retrovirus inside each cell of the subset. The subset of the population that contain the retrovirus may be isolated and/or sorted from the cells of the population that do not contain the retrovirus.

BRIEF DESCRIPTION OF THE DRAWINGS

FIG. 3A demonstrates that the binding interaction of an extracellular targeting domain present in a retrovirus to a cognate ligand of a target cell leads to entry of the retrovirus and subsequent expression of reporter (GFP). FIG. 3B demonstrates that contacting a retrovirus with a non-target cell does not lead to entry of the retrovirus.

FIG. 5A demonstrates that the binding interaction of an extracellular targeting domain present in a retrovirus to a cognate ligand of a target cell leads to entry of the retrovirus and T cell signaling activation. FIG. 5B demonstrates that contacting a retrovirus with a non-target cell does not lead to entry of the retrovirus or T cell signaling activation.

FIG. 7A demonstrates that the binding interaction of an interleuken-13 (IL-13) protein domain present in a retrovirus to an IL-13 protein receptor of a target cell leads to entry of the retrovirus and subsequent expression of reporter (GFP). FIG. 7B demonstrates that contacting a retrovirus comprising an IL-13 protein domain with a non-target cell that does not express an IL-13 protein receptor does not lead to entry of the retrovirus.

FIG. 16A shows the ability of NYESO-1 displaying lentiviruses to transduce IG4-expressing T cells. SL-1 displaying lentiviruses do not transduce IG4-expressing T cells. FIG. 16B shows the mean fluorescence provided by the interaction between NYESO-1 displaying lentiviruses and IG4-expressing T cells.

FIG. 18A depicts an exemplary binding schematic. FIG. 18B depicts graphs showing ability of retroviral constructs to interact with a target cell.

FIG. 22A depicts the transduction rate for each lentivirus. FIG. 22B depicts graphs showing FACS data for GL9 virus and NYESO-1 virus.

DETAILED DESCRIPTION OF THE INVENTION

Figure 1:
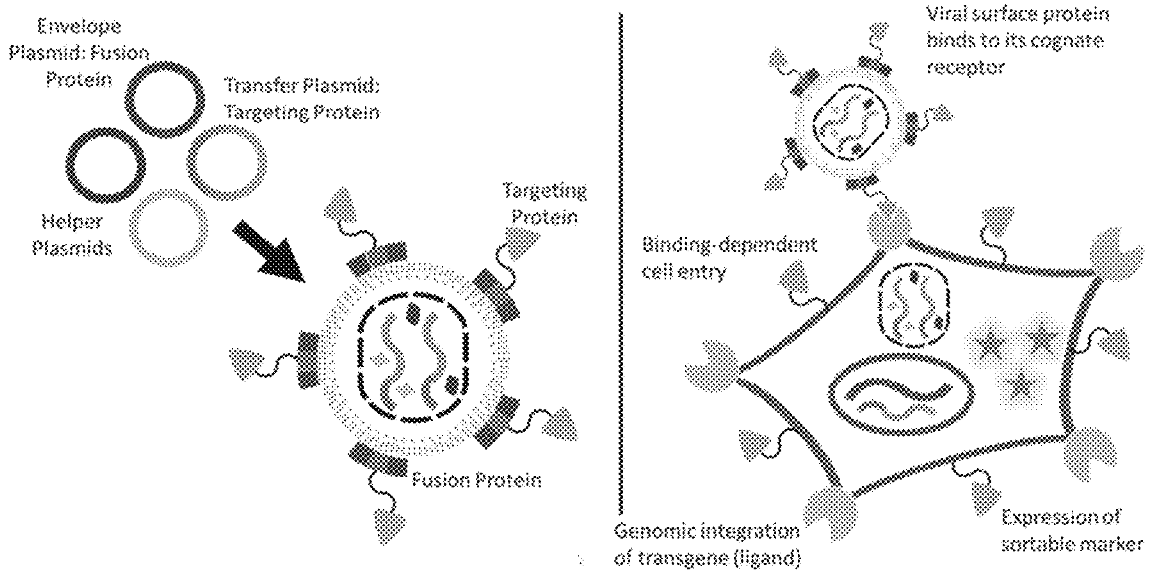
FIG. 1 depicts an exemplary schematic of a retrovirus of the current invention interacting with a cognate ligand of a target cell.

Herein are provided new and innovative methods, for example, to screen cells that are notoriously challenging to screen for specific antigens and function (e.g., T cells), and to deliver nucleic acids to target cells in a target-specific manner. In some embodiments, described herein are systems that enable, for example, repertoire-scale analysis of T cell receptor (TCR)-peptide-Major Histocompatibility Complex (pMHC) specificity, a previously intractable bottleneck, as previously described methods required considerable effort to determine what a single T cell clone can recognize (e.g., as in a typical immune response). In some embodiments, described herein are retrovirus-based systems that repurpose viral tropism as a method of selecting for molecular interactions and replace the binding functions of wild-type virus surface proteins with those of protein variants of interest, for example, by encoding these protein variants on the corresponding transfer plasmid used to make the virus, thereby ensuring that the resulting virus displays the protein variant on its surface and packaging the corresponding genetic sequence. As such, when the virus enters a target cell (e.g., bearing a receptor that binds the displayed extracellular targeting domain of the protein variant), cell entry results in integration of the genetic sequence of the displayed protein into the genome of the target cell.

Previous approaches for studying T cell specificity required a combination of generated T cell lines, recombinant expression of T cell receptors, and/or the individual validation of T cell binding or activity via a candidate antigen-based approach. Each of these elements provided an inherent limitation in the throughput of T cells or antigens screened. For example, yeast display based methods to deorphanize T cell receptors alleviated the bottleneck of number of antigens examined (with the ability to screen $>10^8$ ligands), but were still severely limited by the need to recombinantly express TCRs. The current strategies of the present invention described herein represents a tremendous advance in the study of T cell specificity and screening of T cells by allowing for screening of $>10^8$ ligands and without need for recombinant TCR expression.

Retroviruses

Described herein are retroviruses comprising a viral envelope protein comprising at least one mutation that diminishes its native function, a non-viral membrane-bound protein comprising a membrane-bound domain and an extracellular targeting domain, and a nucleic acid encoding a reporter. In some embodiments, a retrovirus comprises a viral envelope protein comprising at least one mutation that diminishes its native function and a non-viral membrane-bound protein comprising a membrane-bound domain and an extracellular targeting domain.

The retrovirus disclosed herein comprise one or more elements derived from a retroviral genome (naturally-occurring or modified) of a suitable species. Retroviruses include 7 families: alpharetrovirus (Avian leucosis virus), betaretrovirus (Mouse mammary tumor virus), gammaretrovirus (Murine leukemia virus), deltaretrovirus (Bovine leukemia virus), epsilonretrovirus (Walleye dermal sarcoma virus), lentivirus (Human immunodeficiency virus 1), and spumavirus (Human spumavirus). Six additional examples of retroviruses are provided in U.S. Pat. No. 7,901,671.

In some embodiments, a retrovirus is a lentivirus. Lentivirus is a genus of retroviruses that typically gives rise to slowly developing diseases due to their ability to incorporate into a host genome. Modified lentiviral genomes are useful as viral vectors for the delivery of a nucleic acids to a host cell. Host cells can be transfected with lentiviral vectors, and optionally additional vectors for expressing lentiviral packaging proteins (e.g., VSV-G, Rev, and Gag/Pol) to produce lentiviral particles in the culture medium.

Retrovirus and lentivirus constructs are well known in the art and any suitable retrovirus can be used to construct the retrovirus (or a plurality or library of retroviruses) as described herein. Non-limiting examples of retrovirus constructs include lentiviral vectors, human immunodeficiency viral (HIV) vector, avian leucosis viral (ALV) vector, murine leukemia viral (MLV) vector, murine mammary tumor viral (MMTV) vector, murine stem cell virus, and human T cell leukemia viral (HTLV) vector. These retrovirus constructs comprise proviral sequences from the corresponding retrovirus.

The retrovirus described herein may comprise the viral elements such as those described herein from one or more suitable retroviruses, which are RNA viruses with a single strand positive-sense RNA molecule. Retroviruses comprise a reverse transcriptase enzyme and an integrase enzyme. Upon entry into a target cell, retroviruses utilize their reverse transcriptase to transcribe their RNA molecule into a DNA molecule. Subsequently, the integrase enzyme is used to integrate the DNA molecule into the host cell genome. Upon integration into the host cell genome, the sequence from the retrovirus is referred to as a provirus (e.g., proviral sequence or provirus sequence). The retroviral vectors described herein may further comprise additional functional elements as known in the art to address safety concerns and/or to improve vector functions, such as packaging efficiency and/or viral titer. Additional information may be found in US20150316511 and WO2015/117027, the relevant disclosures of each of which are herein incorporated by reference for the purpose and subject matter referenced herein. Additional information for lentiviruses can be found in, e.g., WO2019/056015, the relevant disclosures of which are incorporated by reference herein for this particular purpose.

In some embodiments, lentiviruses are able to be targeted to target-specific cells via the pMHC-TCR interaction or any other protein-protein cell-to-cell interaction. In some embodiments, T cells with a known and relevant specificity can be enhanced (in the case of cancer or infection) or ablated (in the case of autoimmunity) without affecting other T cells, dramatically limiting the risk of off-target effects. In some embodiments, lentiviruses may encode an extracellular domain to target any other surface-expressed molecule on a target cell.

Viral Envelope Protein

The retroviruses described herein comprise a viral envelope protein comprising at least one mutation that diminishes its native function (e.g., wild-type function of a non-mutated viral envelope protein). In some embodiments, a viral envelope protein is any viral envelope protein of any retrovirus (e.g., lentivirus). A viral envelope protein may be a VSV-G envelope protein, a measles virus envelope protein, a nipah virus envelope protein, or a cocal virus G protein. In some embodiments, the native function that is diminished by a mutation of a viral envelope protein is viral tropism (e.g., ability to infect cells, bind to cells, etc.)

In some embodiments, a viral envelope protein comprising at least one mutation that diminishes its native function is a mutated VSV-G envelope protein. In some embodiments, a viral envelope protein comprising at least one mutation that diminishes its native function is a mutated measles virus envelope protein. In some embodiments, a viral envelope protein comprising at least one mutation that diminishes its native function is a mutated nipah virus envelope protein. In some embodiments, a viral envelope protein comprising at least one mutation that diminishes its native function is a mutated cocal virus G protein.

In some embodiments, a mutated VSV-G envelope protein comprises a mutation at H8, K47, Y209, and/or R354. In some embodiments, a mutated VSV-G envelope protein comprises a H8A, K47A, K47Q, Y209A, R354A, and/or R354Q mutation. In some embodiments, a mutated VSV-G envelope protein is as described in Nikolic et al., "Structural basis for the recognition of LDL-receptor family members by VSV glycoprotein." Nature Comm., 2018, 9:1029, the relevant disclosures of which are incorporated by reference herein for this particular purpose.

In some embodiments, a mutated measles virus envelope protein comprises a mutation at Y481, R533, S548, and/or F549. In some embodiments, a mutated measles virus envelope protein comprises a Y481A, R533A, S548L, and/or F549S mutation.

In some embodiments, a mutated Nipah virus envelope protein comprises a mutation at E501, W504, Q530, and/or E533. In some embodiments, a mutated measles virus envelope protein comprises a E501A, W504A, Q530A, and/or E533A mutation.

In some embodiments, a mutated cocal virus G protein comprises a mutation at K64 and/or R371. In some embodiments, a mutated cocal virus G protein comprises a mutation at K64Q and/or R371A.

In some embodiments, the mutated envelope protein is derived from any other enveloped virus including but not limited to baculovirus, herpes simplex virus (HSV), cytomegalovirus (CMV), lymphocytic choriomeningitis virus (LCMV), Epstein-Barr virus (EBV), vaccinia virus, Hepatitis A, B, or C virus, vaccinia virus, alphavirus, dengue virus, yellow fever virus, Zika virus, influenza virus, hantavirus, Ebola virus, rabies virus, human immunodeficiency virus (HIV), coronavirus, and other members of rhabdoviridae.

In some embodiments, a viral envelope protein comprising at least one mutation comprises 1, 2, 3, 4, 5, 6, 7, 8, 9, 10, or more mutations. In some embodiments, a viral envelope protein comprising at least one mutation comprises a nucleotide sequence and/or amino acid sequence that is at least 50%, 60%, 70%, 80%, 90%, 95%, or 97% identical to a wild-type viral envelope protein. In some embodiments, a viral envelope protein comprising at least one mutation that diminishes its native function retains less than 95%, 90%, 80%, 70%, 60%, 50%, 40%, 30%, 20%, or 10% of the function of a wild-type viral envelope protein. In some embodiments, a viral envelope protein comprising at least one mutation lacks all of its native function. In some embodiments, a retrovirus comprising a viral envelope protein comprising at least one mutation that diminishes its native function comprises less than 95%, 90%, 80%, 70%, 60%, 50%, 40%, 30%, 20%, or 10% of the cellular infectivity of a retrovirus comprising a wild-type viral envelope protein.

Non-Viral Membrane-Bound Protein

The retroviruses described herein comprise a non-viral membrane-bound protein. A non-viral membrane-bound protein may comprise a membrane-bound domain and an extracellular targeting domain. In some embodiments, a non-viral membrane-bound protein is a chimeric protein comprising sequences from at least two different proteins. In some embodiments, a non-viral membrane-bound protein is a full-length or truncated protein comprising sequence from a single protein.

A membrane-bound domain is a protein or peptide that has an amino acid sequence that enables the protein or peptide to be fully or partially embedded or associated with the membrane (e.g., envelope) of the retrovirus. In some embodiments, a membrane-bound domain enables presentation and delivery of the extracellular targeting domain to the extracellular environment. In some embodiments, a membrane-bound domain comprises an intracellular domain, a transmembrane domain, and/or an extracellular domain. In some embodiments, a membrane-bound domain comprises an intracellular domain and a transmembrane domain. In some embodiments, the membrane-bound domain comprises a Major Histocompatibility Complex (MHC) protein or fragment thereof. A MHC protein may be a Class I or Class II MHC protein.

In some embodiments, a membrane-bound domain comprises 10-50, 10-100, 25-100, 50-200, 50-150, 100-500, 100-250, 250-500, or any reasonable number of total amino acids.

In some embodiments, a retrovirus present in a library of retroviruses comprises the same membrane-bound domain as some or all of the other retroviruses in the library. In some embodiments, each retrovirus present in a library of retroviruses comprises a different membrane-bound domain relative to some or all of the other retroviruses in the library.

In some embodiments, an extracellular targeting domain is any protein or peptide that has an amino acid sequence and is a binding partner for a target molecule or ligand (e.g., a cognate protein) on a cell surface. When present in the extracellular environment beyond the interior of the retrovirus, an extracellular targeting domain is capable of binding to a target cell. In some embodiments, an extracellular targeting domain binds or targets to a cognate protein or ligand (e.g., a protein receptor present on a target cell) that is present on the cell surface of a cell or a subset of a population of cells. In some embodiments, an extracellular targeting domain binds to a cognate protein or ligand that is present on the cell surface of a single T cell or a subset of a population of T cells. In some embodiments, a binding interaction between an extracellular targeting domain of a retrovirus and a cognate protein or ligand of a cell enables the retrovirus to enter the cell (e.g., an antigen-specific cell, e.g., a T cell).

In some embodiments, an extracellular targeting domain comprises 10-50, 10-100, 25-100, 50-200, 50-150, 100-500, 100-250, 250-500, or any reasonable number of total amino acids. In some embodiments, an extracellular targeting domain comprises at least 5, at least 10, at least 15, at least 20, or at least 50 amino acids.

In some embodiments, an extracellular targeting domain is a protein, an antibody or peptide. In some embodiments, an antibody is a full-length antibody, an antibody fragment, a nanobody, or a single chain antibody (scFv). In some embodiments, an extracellular targeting domain is an antibody that binds to a cognate protein of a target cell. In some embodiments, an extracellular targeting domain is an antibody that binds to a B-cell or T cell antigen. In some embodiments, an extracellular targeting domain is an anti-CD19 antibody (e.g., an antibody that binds to CD19). In some embodiments, an extracellular targeting domain is an antibody that binds to any cell surface molecule. In some embodiments, an extracellular targeting domain is an antibody that binds to a lineage marker (e.g., CD3, CD20, integrins, or other receptors), phenotypic markers (PD-1, CD25, CD45, or others). In some embodiments, an extracellular targeting domain is a protein or peptide that binds to a receptor (e.g., a receptor that is present on the surface of a target cell). In some embodiments, an extracellular targeting domain is a protein or peptide that binds to a cytokine receptor (e.g., interleukin-13 (IL-13) receptor). In some embodiments, an extracellular targeting domain is a cytokine (e.g., IL-2, IL-6, IL-12, IL-13). In some embodiments, an extracellular targeting domain is a chemokine ligand (e.g. CXCL9, CXCL10, CXCL 11, etc.). In some embodiments, an extracellular targeting domain is a cellular receptor, including cytokine receptors (e.g. IL-13Rα1, IL-13Rα2, IL-2 receptors, common gamma chain), GPCRs (including chemokine receptors such as CSCR3, CXCR4, etc.), and integrins. In some embodiments, an extracellular targeting domain is a peptide that is displayed by a MHC protein. In some embodiments, non-viral membrane-bound protein comprises a membrane-bound domain comprising a MHC protein or fragment and an extracellular targeting domain comprising a peptide that is displayed by a MHC protein. In some embodiments, an extracellular domain binds to a T cell receptor and/or a B cell receptor. T-cell receptors are expressed in nature on the surface of T-cells usually as alpha/beta and gamma/delta heterodimeric integral membrane proteins, each subunit comprising a short intracellular segment, a single transmembrane alpha-helix and two globular extracellular Ig-superfamily domains. B-cell receptors are transmembrane receptor proteins located on the outer surface of B cells.

In some embodiments, an extracellular targeting domain binds to a target cell or cell surface molecule with a binding affinity of $10^{-9}$ to $10^{-8}$ M, $10^{-8}$ to $10^{-7}$ M, $10^{-7}$ to $10^{-6}$ M, $10^{-6}$ to $10^{-5}$ M, $10^{-5}$ to $10^{-4}$ M, $10^{-4}$ to $10^{-3}$ M, or $10^{-3}$ to $10^{-2}$ M. In some embodiments, an extracellular targeting domain binds to a cognate protein or ligand of a target cell with a binding affinity of $10^{-9}$ to $10^{-8}$ M, $10^{-8}$ to $10^{-7}$ M, $10^{-7}$ to $10^{-6}$ M, $10^{-6}$ to $10^{-5}$ M, $10^{-5}$ to $10^{-4}$ M, $10^{-4}$ to $10^{-3}$ M, or $10^{-3}$ to $10^{-2}$ M. In some embodiments, the binding affinity between an extracellular targeting domain and a cognate protein or ligand is in the picomolar to nanomolar range (e.g., between about $10^{-12}$ and about $10^{-9}$ M). In some embodiments, the binding affinity between an extracellular targeting domain and a cognate protein or ligand is in the nanomolar to micromolar range (e.g., between about $10^{-9}$ and about $10^{-6}$ M). In some embodiments, the binding affinity between an extracellular targeting domain and a cognate protein or ligand is in the micromolar to millimolar range (e.g., between about $10^{-6}$ and about $10^{-3}$ M). In some embodiments, the binding affinity between an extracellular targeting domain and a cognate protein or ligand is in the picomolar to micromolar range (e.g., between about $10^{-12}$ and about $10^{-6}$ M). In some embodiments, the binding affinity between an extracellular targeting domain and a cognate protein or ligand is in the nanomolar to millimolar range (e.g., between about $10^{-9}$ and about $10^{-3}$ M).

As used herein, the term antibody generally refers to a protein that includes at least one immunoglobulin variable domain or immunoglobulin variable domain sequence. For example, an antibody can include a heavy (H) chain variable region (abbreviated herein as $V_H$), and/or a light (L) chain variable region (abbreviated herein as $V_L$). In another example, an antibody includes two heavy (H) chain variable regions and/or two light (L) chain variable regions. An antibody can have the structural features of IgA, IgG, IgE, IgD, IgM (as well as subtypes thereof). The $V_H$ and $V_L$ regions can be further subdivided into regions of hypervariability, termed “complementarity determining regions” (“CDR”), interspersed with regions that are more conserved, termed “framework regions” (“FR”). Each $V_H$ and/or $V_L$ is typically composed of three CDRs and four FRs, arranged from amino-terminus to carboxy-terminus in the following order: FR1, CDR1, FR2, CDR2, FR3, CDR3, FR4. The $V_H$ or $V_L$ chain of the antibody can further include a heavy or light chain constant region, to thereby form a heavy or light immunoglobulin chain, respectively. In some embodiments, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3.

In some embodiments, a retrovirus present in a library of retroviruses comprises the same extracellular targeting domain as some or all of the other retroviruses in the library. In some embodiments, each retrovirus present in a library of retroviruses comprises a different extracellular targeting domain relative to some or all of the other retroviruses in the library.

In some embodiments, a non-viral membrane-bound protein further comprises a signal sequence (also referred to as a signal peptide of localization sequence). In some embodiments, the signal sequence is at the N- or C-terminal ends of the non-viral membrane-bound protein. A signal sequence functions to translocate the non-viral membrane-bound protein to the membrane (or envelope) of the retrovirus. In some embodiments, a signal sequence is 5-10, 5-15, 10-20, 15-20, 15-30, 20-30, or 25-30 amino acids. In some embodiments, the signal sequence is an Ig Kappa leader sequence (e.g., a murine Ig Kappa leader sequence comprising: METDTLLLWVLLLWVPGSTG (SEQ ID NO: 1)) or a B2M signal peptide sequence (e.g., a B2M signal peptide sequence comprising: MSRSVALAVLALLSLSGLEA (SEQ ID NO: 2)). In some embodiments, a retrovirus present in a library of retroviruses comprises the same signal sequence as some or all of the other retroviruses in the library. In some embodiments, each retrovirus present in a library of retroviruses comprises a different signal sequence relative to some or all of the other retroviruses in the library.

In some embodiments, a nucleic acid encoding a non-viral membrane-bound protein further comprises an internal ribosome entry site (IRES). An IRES is an RNA sequence that allows for initiation of translation during protein synthesis. In some embodiments, the IRES is located at or near the C-terminal end. In some embodiments, the IRES is located C-terminal relative to the membrane-bound domain and the extracellular targeting domain. In some embodiments, the IRES is a viral IRES. In some embodiments, the IRES is an IRES that is native to the retrovirus. In some embodiments, the IRES is a sequence derived from encephalomyocarditis virus (EMCV). In some embodiments, a retrovirus present in a library of retroviruses comprises the same IRES as some or all of the other retroviruses in the library. In some embodiments, each retrovirus present in a library of retroviruses comprises a different IRES relative to some or all of the other retroviruses in the library.

In some embodiments, a non-viral membrane-bound protein further comprises a linker positioned between the membrane-bound domain and the extracellular targeting domain. A linker is an amino acid linker and may be a rigid linker, a flexible linker, or an oligomerized linker. A rigid linker is an amino acid sequence that lacks flexibility (e.g., may comprise at least one proline). In some embodiments, a rigid linker comprises a platelet-derived growth factor receptor (PDGFR) stalk or a CD8α stalk. In some embodiments, a PDGFR stalk comprises an amino acid sequence comprising AVGQDTQEVIVVPHSLPFK (SEQ ID NO: 3). In some embodiments, a PDGFR stalk comprises an amino acid sequence comprising

```
                                    (SEQ ID NO: 4)
ASAKPTTTPAPRPPTPAPTIASQPLSLRPEAARPAAGGAVHTRGLDFAK
```

A flexible linker is an amino acid sequence that has many degrees of freedom (e.g., may comprise a plurality of amino acids with small side chains, e.g., glycine or alanine). In some embodiments, a flexible linker comprises an amino acid sequence comprising GAPGAS (SEQ ID NO: 5). In some embodiments, a flexible linker comprises an amino acid sequence consisting of GAPGSGGGGSGGGGSAS (SEQ ID NO: 6). In some embodiments, a flexible linker comprises an amino acid sequence comprising GGGGS (SEQ ID NO: 7). In some embodiments, a flexible linker comprises an amino acid sequence comprising $(GAPGAS)_N$ (SEQ ID NO: 29) or $(G_4S)_N$ (SEQ ID NO: 30), wherein N is 1, 2, 3, 4, 5, 6, 7, 8, 9, 10, or more. An oligomerized linker is an amino acid that can oligomerize to another related amino amid. In some embodiments, an oligomerized linker is an amino acid sequence that can form a dimer, trimer, or tetramer. In some embodiments, an oligomerized linker comprises an IgG4 hinge domain (e.g., ASESKYGPPCPPCPAVGQDTQEVIVVPHSLPFK (SEQ ID NO: 8)). In some embodiments, an oligomerized linker comprises an amino acid sequence that can form a tetrameric coiled coil (e.g., ASGGGGSGELAAIKQELAAIKKELAAIKWELAAIKQGAG (SEQ ID NO: 9)). In some embodiments, an oligomerized linker comprises an amino acid sequence that can form a dimeric coiled coil (e.g., ASESKYGPPCPPCP (SEQ ID NO: 10)).

Reporter

In some embodiments, the retroviruses described herein may comprise a reporter (e.g., a reporter protein). In some embodiments, the retroviruses described herein comprise a nucleic acid encoding a reporter (e.g., a reporter protein). As used herein, a reporter is generally a protein or gene that can be detected when expressed in a retrovirus and/or target cell. In some embodiments, the presence or absence of a reporter in a target cell or a subset of a target cells in a population of cells allows for the ability to sort cells (e.g., using flow cytometry and/or fluorescence-activated cell sorting).

In some embodiments, a reporter is a fluorescent protein. A fluorescent protein may be a green fluorescent protein (GFP), yellow fluorescent protein (YFP), red fluorescent protein (RFP). A fluorescent protein may be as described in U.S. Pat. No. 7,060,869, entitled “Fluorescent protein sensors for detection of analytes”.

In some embodiments, a reporter is an antibiotic resistance marker. In some embodiments, an antibiotic resistance marker is a protein or gene that confers a competitive advantage to a target cell that contains the marker. In some embodiments, the antibiotic resistance marker comprises a hygromycin resistance protein or gene, a kanamycin resistance protein or gene, ampicillin resistant protein or gene, streptromycin resistant protein or gene, or a neomycin resistance protein or gene.

Cells

A cell as described herein may be any bacterial, mammalian, or yeast cell. In some embodiments, a cell is a human, mouse, rat, or a non-human primate cell. In some embodiments, a cell is a somatic cell or a reproductive cell. In some embodiments, a cell is an epithelial cell, a neural cell, a hormone-secreting cell, an immune cell, a secretory cell, a blood cell, an interstitial cell, or a germ cell. In some embodiments, a cell is an antigen-specific cell (e.g., a cell that binds to a specific antigen). In some embodiments, an antigen-specific cell is an immune cell. In some embodiments, an antigen-specific cell is a B cell or a T cell. In some embodiments, a cell is a target cell (e.g., that comprises a cognate protein or ligand capable of being targeted by a retrovirus described herein)

A population of cells as described herein may be any bacterial, mammalian, or yeast cell population. In some embodiments, a population of cells is a population of human, mouse, rat, or non-human primate cells. In some embodiments, a population of cells is a somatic cell population or a reproductive cell population. In some embodiments, a population of cells comprises epithelial cells, neural cells, hormone-secreting cells, immune cells, secretory cells, blood cells, interstitial cells, and/or germ cells. In some embodiments, a population of cells comprises antigen-specific cells (e.g., cells that binds to a specific antigen). In some embodiments, a population of antigen-specific cells comprises immune cells. In some embodiments, a population of antigen-specific cells comprises B cells and/or T cells. In some embodiments, a population of cells comprises a homogenous population of cells. In some embodiments, a population of cells comprises a heterogeneous population of cells.

In some embodiments, a population of cells is a population of cells isolated from a subject. A subject may be a human subject (e.g., a human subject suffering from a disease), a mouse subject, a rat subject, or a non-human primate subject. In some embodiments, a population of cells is isolated from the blood or a tumor of a subject.

In some embodiments, a population of cells has been previously frozen and thawed (e.g., 1, 2, 3, 4, 5, or more freeze/thaw cycles). In some embodiments, a population of cells are maintained in liquid culture media. In some embodiments, a population of cells have been passaged 1, 2, 3, 4, 5, or more times, using any known method. In some embodiments, a population of cells are maintained in liquid culture media prior to being combined with a retrovirus or plurality of retroviruses. In some embodiments, a population of cells are maintained in liquid culture media after to being combined with a retrovirus or plurality of retroviruses. In some embodiments, a population of cells are maintained in liquid culture media prior to while being combined with a retrovirus or plurality of retroviruses.

In some embodiments, a population of cells comprises any of the retroviruses described herein. In some embodiments, a subset of a population of cells contain any of the retroviruses described herein. In some embodiments, a subset of a population of cells contains the retrovirus inside each cell of the subset (e.g., inside the nucleus of each cell of the subset). In some embodiments, a population of cells or a subset thereof expresses a reporter (e.g., a fluorescent protein or an antibiotic resistance marker). In some embodiments, a population of cells or a subset thereof (e.g., containing a retrovirus) are isolated and/or sorted based on the presence or absence of a reporter. In some embodiments, a subset of a population of cells that contain retrovirus described herein are isolated and/or sorted based on the presence or absence of a reporter away from the cells of the population that do not contain the retrovirus. In some embodiments, at least 50%, 60%, 70%, 80%, 90%, or 95% of a population of cells prior to cell sorting contain a retrovirus. In some embodiments, at least 70%, 80%, 90%, 95%, or 100% of a population of cells contain a retrovirus following isolation and/or sorting based on the presence or absence of a reporter.

Methods of Screening

Described herein are methods of screening a population of cells comprising: (i) providing a retrovirus comprising a viral envelope protein comprising at least one mutation that diminishes its native function, a non-viral membrane-bound protein comprising a membrane-bound domain and an extracellular targeting domain, and a nucleic acid encoding a reporter; (ii) combining the retrovirus with a population of cells; and (iii) sorting the population of cells based on the presence or absence of the reporter. In some embodiments, the retrovirus of (i) comprises a nucleic acid comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter; and a mutated viral envelope protein comprising at least one mutation that diminishes its native function.

As used herein, the term "combining" (which, in some embodiments, is synonymous with the terms "providing" and "contacting") generally refers to the act of bringing a retrovirus into close, physical contact with a population of cells, such that the extracellular targeting domain of the retrovirus is capable of binding to the cognate ligand present on a subset of cells of the population. In some embodiments, combining of a retrovirus and a population of cells occurs when a solution comprising the retrovirus and a solution comprising the population of cells are mixed. In some embodiments, combining of a retrovirus and a population of cells occurs when a lyophilized retrovirus and a solution comprising the population of cells are mixed. In some embodiments, combining of a retrovirus and a population of cells occurs when a lyophilized retrovirus and a lyophilized population of cells are mixed and reconstituted with a solution. In some embodiments, the cells of the population are maintained in cell culture media, in a monolayer of cells, and/or are attached to a tissue culture plate or petri dish.

Generally, a retrovirus and a population of cells are combined (e.g., physically combined or contacted) for a defined period of time. In some embodiments, a period of time is measured in seconds, minutes, hours or days. In some embodiments, period of time is 0-30 seconds, 15-45 seconds, 30-60 seconds, 45-90 seconds, 60-90 seconds, or 60-120 seconds. In some embodiments, a retrovirus and a population of cells are combined and in contact for 0-30 seconds, 15-45 seconds, 30-60 seconds, 45-90 seconds, 60-90 seconds, or 60-120 seconds. In some embodiments, period of time is 1-2 minutes, 1-5 minutes, 1-10 minutes, 2-10 minutes, 5-10 minutes, 5-20 minutes, 10-20 minutes, 25-30 minutes, 25-60 minutes, 30-45 minutes, 30-40 minutes, 40-60 minutes, 50-70 minutes, or 60-120 minutes. In some embodiments, a retrovirus and a population of cells are combined and in contact for 1-2 minutes, 1-5 minutes, 1-10 minutes, 2-10 minutes, 5-10 minutes, 5-20 minutes, 10-20 minutes, 25-30 minutes, 25-60 minutes, 30-45 minutes, 30-40 minutes, 40-60 minutes, 50-70 minutes, or 60-120 minutes. In some embodiments, a period of time is 1-2 hours, 1-5 hours, 1-3 hours, 2-5 hours, 3-6 hours, 3-12 hours, 6-12 hours, 12-18 hours, 12-24 hours, 15-30 hours, 18-24 hours, 24-48 hours, 24-36 hours, or 36-50 hours. In some embodiments, a retrovirus and a population of cells are combined and in contact for 1-2 hours, 1-5 hours, 1-3 hours, 2-5 hours, 3-6 hours, 3-12 hours, 6-12 hours, 12-18 hours, 12-24 hours, 15-30 hours, 18-24 hours, 24-48 hours, 24-36 hours, or 36-50 hours. In some embodiments, a period of time is 1, 2, 3, 4, 5, 6, 7, 8, 9, 10, or 5-15 days. In some embodiments, a retrovirus and a population of cells are combined and in contact for 1, 2, 3, 4, 5, 6, 7, 8, 9, 10, or 5-15 days.

In some embodiments, a population of cells are sorted based on the presence or absence of the reporter. In some embodiments, a subset of the population of cells containing the reporter (e.g., express the reporter) are sorted from the remaining subset of the population of cells that do not contain the reporter. In some embodiments, sorting of the population of cells is performed using flow cytometry (e.g., fluorescence-activated cell sorting), next-generation genome sequencing (e.g., single-cell next-generation sequencing), or antibiotic selection.

In some embodiments, the conditions of step (ii) that allow for the retrovirus to have cell-to-cell interactions with a subset of the population of cells comprise combining the retrovirus and the population of cells in the presence of defined solutions, compositions and at specific temperatures. In some embodiments, the retrovirus and the population of cells are combined in the presence of a cell culture media (e.g., RPMI or DMEM cell culture media). In some embodiments, the retrovirus and the population of cells are combined in the presence of a buffered saline solution. In some embodiments, a buffered saline solution is a phosphate-buffered saline or HEPES-buffered saline. In some embodiments, a buffered saline solution comprises bovine serum albumin and/or EDTA. In some embodiments, the retrovirus and the population of cells are combined in the presence of an enhancer of retroviral transduction (e.g., heparin sulfate, polybrene, protamine sulfate, or dextran). In some embodiments, the retrovirus and the population of cells are combined in (ii) at a temperature ranging from 4° C. to 42° C., 4° C. to 8° C., 4° C. to 10° C., 8° C. to 15° C., 10° C. to 20° C., 18° C. to 23° C., 20° C. to 30° C., 25° C. to 35° C., 30° C. to 40° C., or 37° C. to 42° C.

In some embodiments, the methods of screening described herein further comprise washing the population of cells between steps (ii) and (iii) with a wash solution. In some embodiments, a wash solution is any liquid solution that allows for maintenance of healthy cells (e.g., solution comprising neutral pH, low-to-moderate levels of ionic strength). In some embodiments, washing the population of cells removes excess and/or remaining retrovirus from the population of cells. In some embodiments, the population of cells are washed using a cell culture media (e.g., RPMI or DMEM cell culture media). In some embodiments, the population of cells are washed using a buffered saline solution. In some embodiments, a buffered saline solution is a phosphate-buffered saline or HEPES-buffered saline. In some embodiments, a buffered saline solution comprises bovine serum albumin and/or EDTA. In some embodiments, the population of cells are washed at a temperature ranging from 4° C. to 42° C., 4° C. to 8° C., 4° C. to 10° C., 8° C. to 15° C., 10° C. to 20° C., 18° C. to 23° C., 20° C. to 30° C., 25° C. to 35° C., 30° C. to 40° C., or 37° C. to 42° C.

In some embodiments, the population of cells are maintained in liquid culture prior to being combined with the retrovirus. In some embodiments, the population of cells are maintained in liquid culture after being combined with the retrovirus. In some embodiments, the population of cells are maintained in liquid culture during the combining step with the retrovirus. In some embodiments, the population of cells are attached to a cell culture plate or petri dish. In some embodiments, the population of cells are maintained in a monolayer, an embryoid body, or any cell aggregate.

In some embodiments, methods of screening comprise the use of a plurality of retroviruses. In certain embodiments, a plurality of retroviruses comprises at least $10^2$, $10^3$, $10^4$, $10^5$, $10^6$, $10^7$, $10^8$, $10^9$, $10^{10}$, $10^{11}$, or $10^{12}$ unique retroviruses. In some embodiments, there may be at least $10^2$, $10^3$, $10^4$, $10^5$, $10^6$, $10^7$, $10^8$, $10^9$, $10^{10}$, $10^{11}$, or $10^{12}$ copies of each unique retrovirus present in a plurality of retroviruses.

In some embodiments, methods of screening comprise screening a population of cells with at least two different, unique retroviruses. In some embodiments, a different, unique retrovirus comprises a different extracellular targeting domain and/or a different reporter. In some embodiments, methods of screening comprise a first retrovirus and a second retrovirus, wherein the first and second retrovirus comprise different extracellular targeting domains and/or different reporters. In some embodiments, methods of screening comprise screening a population of cells with 2, 3, 4, 5, 6, 7, 8, 9, 10, 50, 100 or more different retroviruses. In some embodiments, methods of screening comprise screening a population of cells with a library of retroviruses. In some embodiments, a library of retroviruses comprises at least $10^2$, at least $10^3$, at least $10^4$, at least $10^5$, at least $10^6$, at least $10^7$, at least $10^8$, at least $10^9$, or at least $10^{10}$ unique retroviruses.

Library of Retroviruses

Described herein are libraries of retroviruses, wherein a library comprises a plurality of unique retroviruses, wherein each unique retrovirus comprises a viral envelope protein comprising at least one mutation that diminishes its native function, a non-viral membrane-bound protein comprising a membrane-bound domain and an extracellular targeting domain, and a nucleic acid encoding a reporter, and wherein each unique retrovirus comprises a different and unique extracellular targeting domain. Also described herein are libraries of cells comprising retroviruses, wherein a library comprises a plurality of unique cells, wherein each unique cell comprises a unique retrovirus.

In some embodiments, libraries include pMHC-encoded (peptide/MHC-encoded) retroviral (e.g., lentiviral) libraries for use in screening populations of T cells. In such libraries, the pMHC displayed on the virus surface will enable T cell infection in a TCR-specific manner. Infected T cells can be collected and sequenced, allowing for the identification of pMHC ligands that can infect a subset of a T cell population of interest and the ability to simultaneously track TCR sequences and reactive pMHC ligands. In some embodiments, pMHC retroviral libraries minimally comprise randomized transfer vectors containing randomized pMHC targeting elements. In some embodiments, randomly derived libraries are generated using degenerate oligonucleotide primers. In some embodiments, targeted libraries that are specific for a unique set of antigens (e.g., all possible viral or bacterial antigens for a particular target of interest—human immunodeficiency virus, tuberculosis TB, etc.; or all possible neoantigens for a particular subject) are generated.

In some embodiments, a library is capable of being screened against a population of antigen-specific cells (e.g., B cells or T cells). In some embodiments, a library comprises at least $10^2$, at least $10^3$, at least $10^4$, at least $10^5$, at least $10^6$, at least $10^7$, at least $10^8$, at least $10^9$, or at least $10^{10}$ unique retroviruses. In some embodiments, a library comprising unique retroviruses comprises extracellular targeting domains that are at least 5, at least 10, at least 15, at least 20, or at least 50 amino acids in length. In some embodiments, each different and unique extracellular targeting domain is generated through site-directed mutagenesis.

Retroviral or cell libraries can vary in size from hundreds to hundreds of thousands, millions, or more unique retroviruses or unique cells. In some embodiments, the libraries of the disclosure comprise at least 500,000 unique retroviruses or unique cells. The libraries of the invention include retroviral libraries and cellular libraries. A library is a synthetic (i.e., isolated, synthetically produced, free from components that are naturally found together in a cell, purified before being put into the library) collection of members having a common element and at least one distinct element. The library comprises a thousand or more (e.g., at least: 1,000; 2,000; 3,000; 4,000; 5,000; 10,000; 50,000; 100,000; 500,000; 600,000; 700,000; 800,000; 900,000; 1,000,000; 2,000,000; 3,000,000; 4,000,000; or more) members. The upper limit of the library size is defined by the combinatorics of domains or modules providing distinctness or diversity among the members. For instance, an upper limit may be 4,000,000 members. Thus, in some embodiments, the library is highly diverse, and includes at least 500,000 distinct members. The highly diverse library may have a diversity of $10^6$ or greater. In some embodiments, a library of retroviruses is generated using site-directed mutagenesis of a nucleic acid described herein. In some embodiments, the site-directed mutagenesis involves the use of primers and a low-fidelity RNA polymerase to allow for randomized mutagenesis of a common nucleic acid as described herein.

Methods of Delivering Nucleic Acid to a Cell

Described herein are methods of delivering a nucleic acid to a cell, comprising (i) providing a retrovirus, as described herein, comprising the nucleic acid, a viral envelope protein comprising at least one mutation that diminishes its native function, and a non-viral membrane-bound protein comprising an extracellular targeting domain that is capable of binding to a cognate ligand of the cell; and (ii) contacting the retrovirus with the cell such that the retrovirus enters or infects the cell. In some embodiments, the nucleic acid encodes an mRNA molecule, optionally wherein the mRNA is a gene of interest. In some embodiments, the nucleic acid encodes a double-stranded RNA, an antisense RNA, a microRNA, or any other RNA molecule. In some embodiments, the gene of interest encodes a protein. In some embodiments, the gene of interest encodes a therapeutic protein (e.g., a protein to compensate for a diseased condition in a subject).

In some embodiments, the nucleic acid is delivered to the cell when the retrovirus enters or infects the cell during step (ii). In some embodiments, the methods of delivering a nucleic acid described herein do not require a transfection agent (e.g., a lipophilic transfection agent such as Lipofectin).

Methods of Detection

Described herein are methods of detecting an interaction between a retrovirus and a cell, comprising: (i) contacting a sample comprising the retrovirus and an cell with an antibody, wherein the retrovirus comprises a viral envelope protein comprising at least one mutation that diminishes its native function, a non-viral membrane-bound protein comprising an extracellular targeting domain, and wherein the antibody binds to the extracellular targeting domain of the retrovirus; (ii) optionally removing unbound antibody from the sample; and (iii) imaging the sample to detect whether the antibody-retrovirus complex is bound to the cell.

In some embodiments, the antibody further comprises at least one fluorescent label. In some embodiments, a fluorescent label is a xanthene derivative (e.g., fluorescein, rhodamine, Oregon green, eosin and Texas red), cyanine derivative (e.g., cyanine, indocarbocyanine, oxacarbocyanine, thiacarbocyanine and merocyanine), naphthalene derivative (e.g., dansyl and prodan derivatives), coumarin derivative, oxadiazole derivative (e.g., pyridyloxazole, nitrobenzoxadiazole and benzoxadiazole), pyrene derivative (e.g., cascade blue), oxazine derivative (e.g., Nile red, Nile blue, cresyl violet and oxazine 170), acridine derivative (e.g., proflavin, acridine orange and acridine yellow), arylmethine derivative (e.g., auramine, crystal violet and malachite green), or tetrapyrrole derivative (e.g., porphin, phthalocyanine and bilirubin). The fluorescent label may be non-covalently associated with the antibody or covalently linked to the antibody.

In some embodiments, the sample is imaged in step (iii) using confocal or fluorescence microscopy. In some embodiments, methods of detection can be accomplished using standard microscopy setups (e.g., confocal or fluorescence microscopes). In some embodiments, a sample is detected in an ultra-multiplexed format while imaging using standard confocal or epi-fluorescence microscope.

Nucleic Acids

As used herein, the term "nucleic acids" generally refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). Nucleic acids include DNA such as D-form DNA and L-form DNA and RNA, as well as various modifications thereof. Modifications include base modifications, sugar modifications, and backbone modifications.

It is to be understood that the nucleic acids used in retroviruses and methods of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The modification may render the nucleic acid more stable and/or less susceptible to degradation under certain conditions. For example, in some instances, the nucleic acids are nuclease-resistant. Methods for synthesizing nucleic acids, including automated nucleic acid synthesis, are also known in the art.

The nucleic acids may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7 deazaguanine, 7 deaza 7 substituted guanine (such as 7 deaza 7 (C2 C6)alkynylguanine), 7 deaza 8 substituted guanine, hypoxanthine, N2-substituted guanines (e.g. N2-methyl-guanine), 5-amino-3-methyl-3H,6H-thiazolo[4,5-d]pyrimidine-2,7-dione, 2,6 diaminopurine, 2 aminopurine, purine, indole, adenine, substituted adenines (e.g. N6-methyl-adenine, 8-oxo-adenine) 8 substituted guanine (e.g. 8 hydroxyguanine and 8 bromoguanine), and 6 thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

Amino Acid Substitutions

In some embodiments, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

EXAMPLES

Example 1. Generation of Retrovirus that Targets Antigen-Specific T Cells

Figure 2:
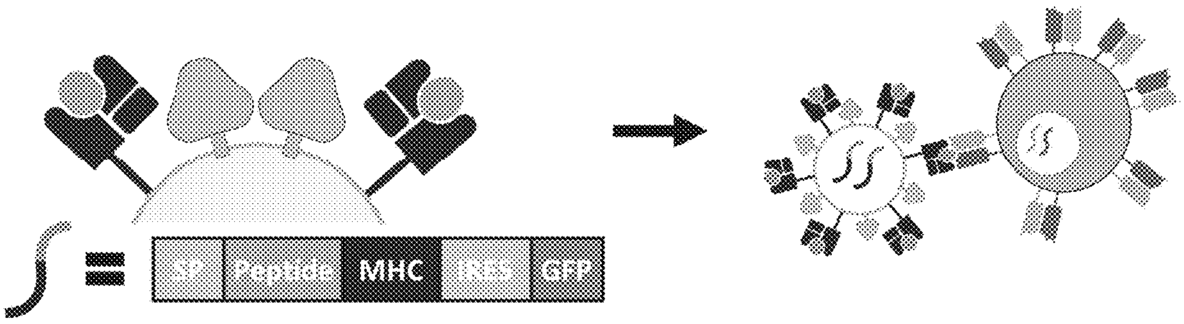
FIG. 2 depicts an exemplary schematic of a protein comprising a signal sequence (SP), an extracellular targeting domain (peptide), a membrane-bound domain (MHC), an internal ribosome entry site (IRES), and a reporter (GFP); and the ability of a retrovirus comprising said protein to interact with a target cell.

Targeted lentiviruses were generated by polyethylenimine (PEI) transfection of HEK293T cells with the following plasmids: an envelope plasmid encoding a mutated VSV-G envelope protein comprising K47Q and R354A mutations, at least one helper plasmid (pRRE, pRev, or psPAX2.1), and a transfer plasmid (FIG. 1). The transfer plasmids used encoded a nucleic acid comprising a structure: S-ETD-MBD-IRES-R, wherein S encoded a B2M signal sequence (as provided by SEQ ID NO: 2), ETD encoded a variable extracellular targeting domain (e.g., the cancer-testis antigen NYESO-1); MBD encoded a membrane bound domain (e.g., MHC HLA-A2 domain), IRES encoded an internal ribosome entry site derived from encephalomyocarditis virus (EMCV), and R encoded a green fluorescent protein GFP reporter (FIG. 2).

The resulting viruses were harvested and purified by standard centrifugation techniques, prior to mixing (using pipette mixing) with T cell lines (e.g. Jurkat T cells) expressing T cell receptors (TCRs) specific to known pMHCs in the presence of hexadimethrine bromide.

Figure 3A:
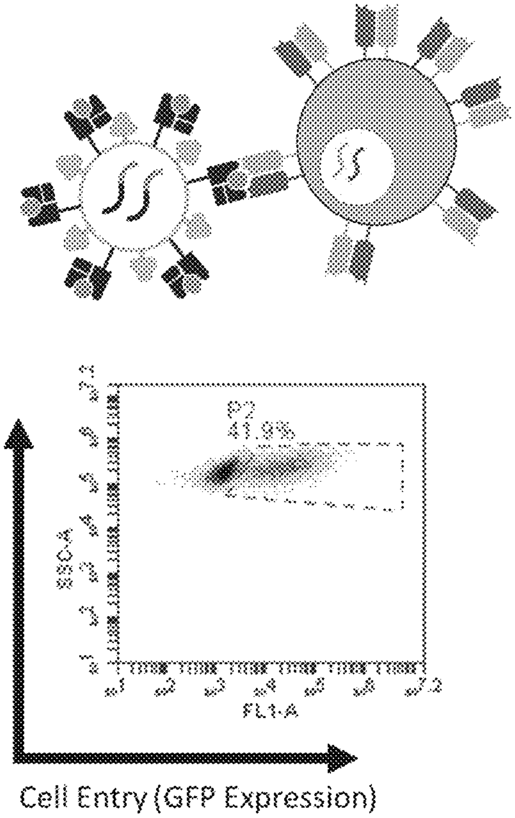
FIGS. 3A-3B depict graphs showing retroviral entry into a target cell.
Figure 3B:
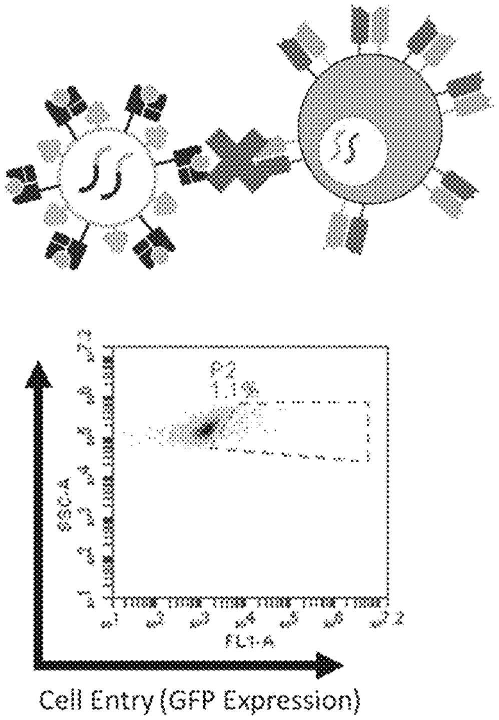

Mixing HLA-A2-NYESO-1 pMHC-displaying viruses with Jurkat T cells expressing an IG4 T cell receptor (TCR) variant (SEQ ID NO: 27) that recognizes the displayed NYESO-1 with a binding affinity of ~26 pM, efficient infection was observed, with 41.9% of T cells expressing the GFP reporter after mixing (FIG. 3A). This result indicated that 41.9% of T cells in this cell population were infected by the virus. Conversely, mixing HLA-A2-NYESO-1 pMHC-displaying viruses were mixed with cells that did not express an IG4 TCR, minimal infection was observed, with only 1.1% of T cells expressing the GFP reporter after mixing (FIG. 3B).

Figure 4:
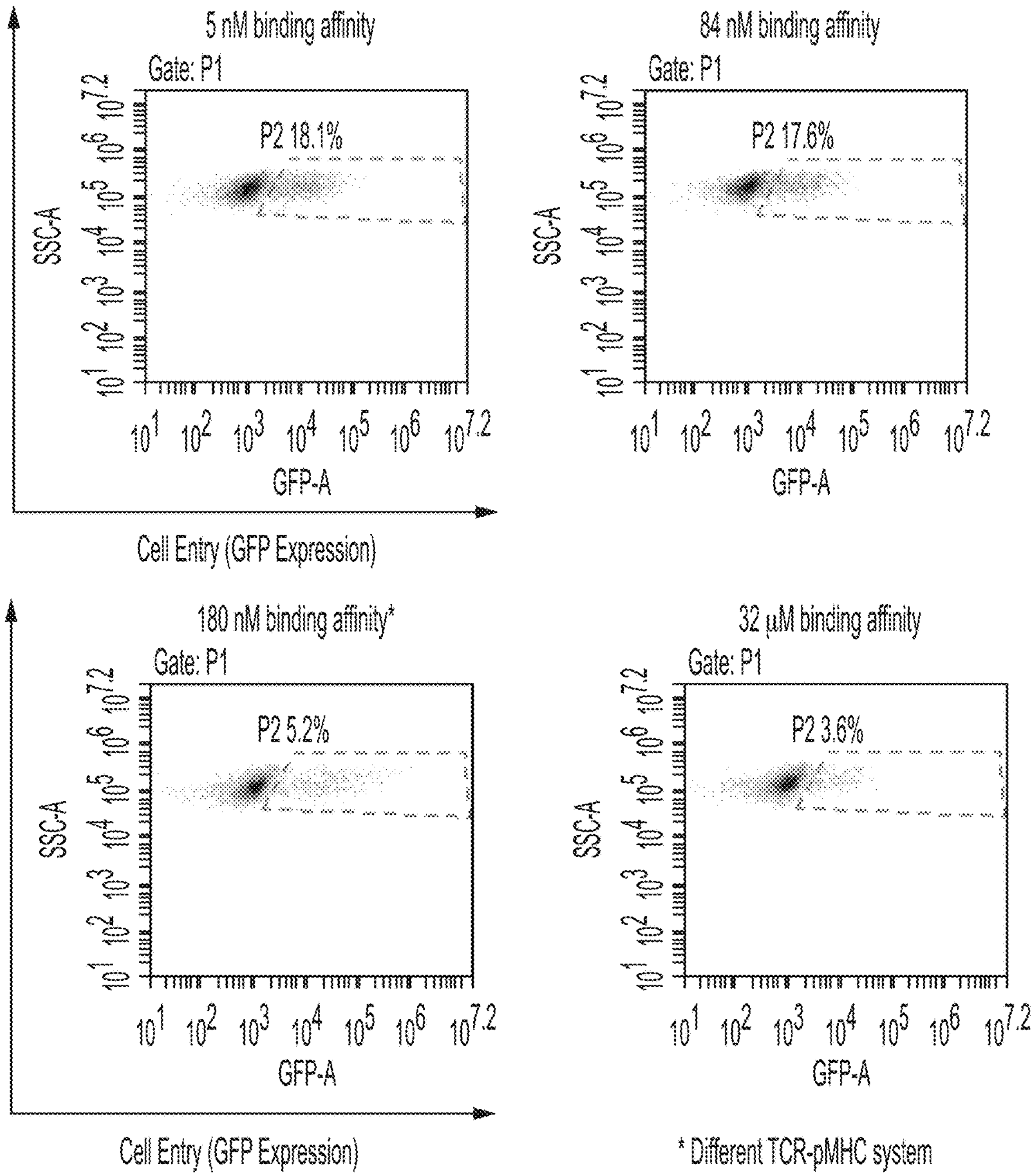
FIG. 4 depicts graphs showing the ability of retroviral entry into target cells at variable affinities between an extracellular targeting domain and its cognate ligand.

Mixing HLA-A2-NYESO-1 pMHC-displaying viruses with T cells expressing different versions of the IG4 TCR (wherein the different versions of the IG4 TCR exhibit reduced binding to the NYESO-1 antigen, compared to IG4 TCR variant comprising SEQ ID NO: 27) demonstrated that the viruses were able to infect T cells even when the binding affinity between the NYESO-1 antigen and IG4 TCR was down to 32 μM (FIG. 4). A 32 μM binding affinity between NYESO-1 antigen and an IG4 TCR variant (SEQ ID NO: 24) provided 3.6% transduction; a 84 nM binding affinity between NYESO-1 antigen and a IG4 TCR variant (SEQ ID NO: 25) provided 17.6% transduction; and a 5 nM binding affinity between NYESO-1 antigen and a IG4 TCR variant (SEQ ID NO: 26) provided 18.1% transduction; when measuring for GFP expression.

Figure 5A:
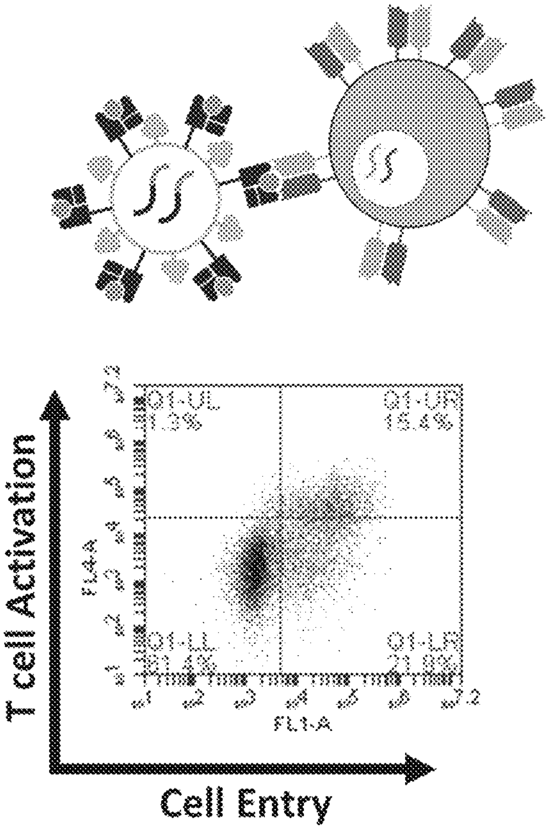
FIGS. 5A-5B depict graphs showing that T cell signaling is active during retroviral entry or infection.
Figure 5B:
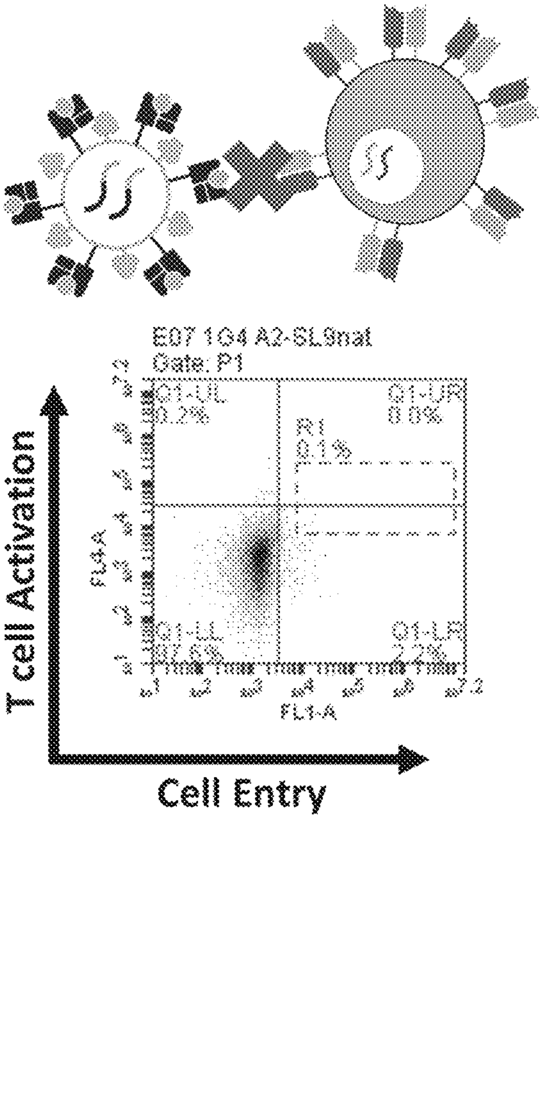
Figure 6:
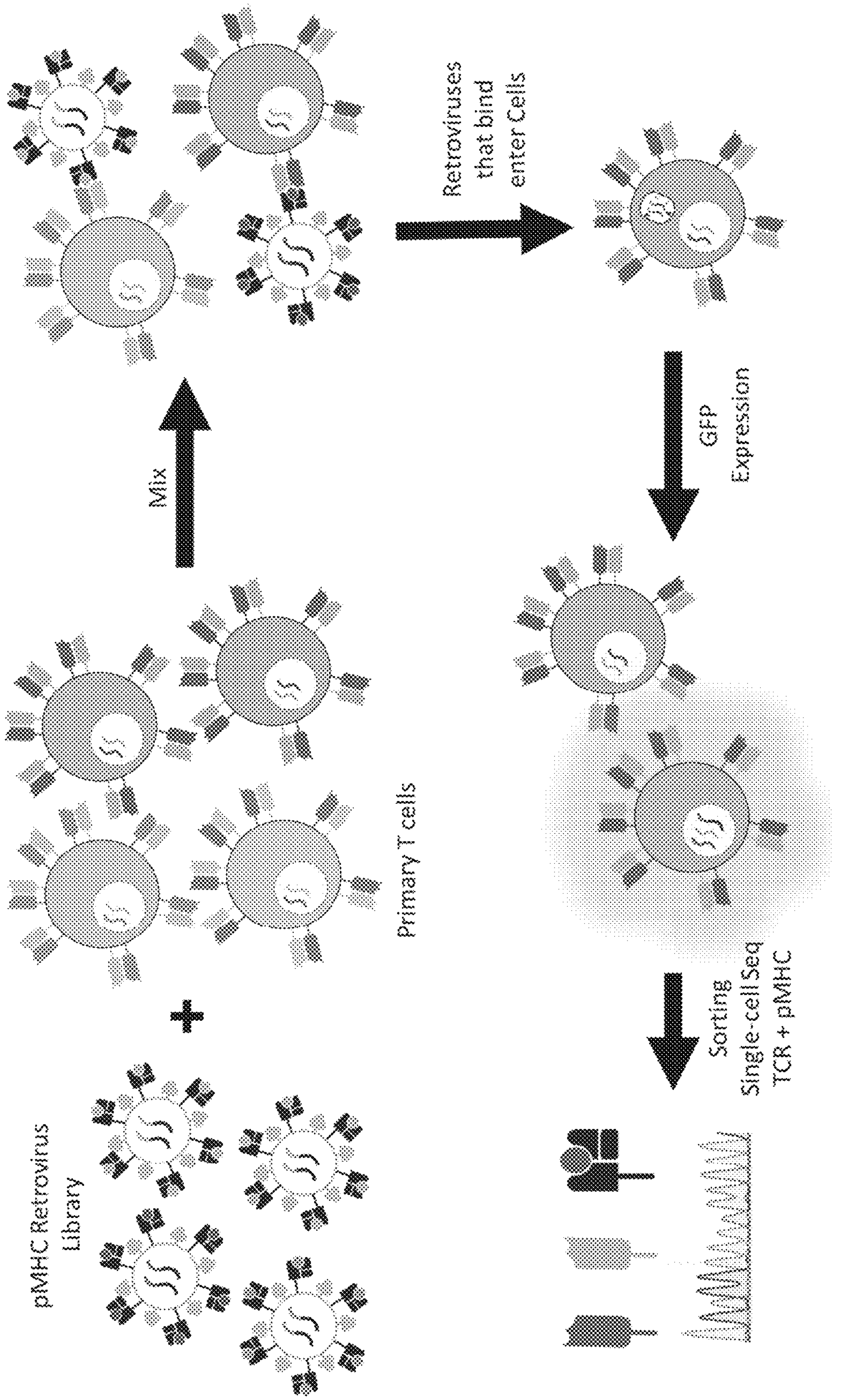
FIG. 6 depicts an exemplary schematic of a pMHC retroviral library screening methodology.

1G4-expressing T cells exhibited T cell activation when transduced/infected with HLA-A2-NYESO-1-displaying viruses, as evidenced by upregulation of CD69 (FIG. 5A). Conversely, HLA-A2-SL9-displaying viruses did not transduce/infect nor activate 1G4-expressing T cells (FIG. 5B).

Example 2. Generation of Retroviruses that Target IL-13 Receptor

Figure 7A:
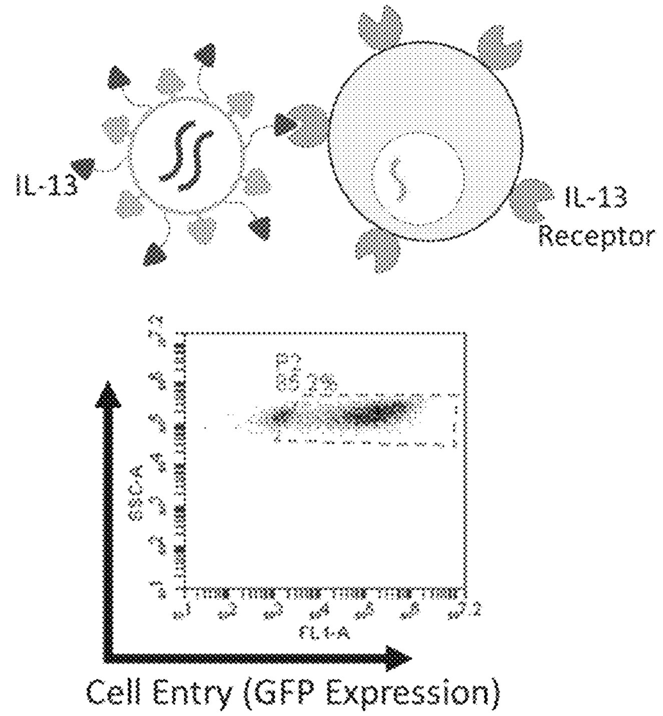
FIGS. 7A-7B depict graphs showing retroviral entry into a target cell.
Figure 7B:
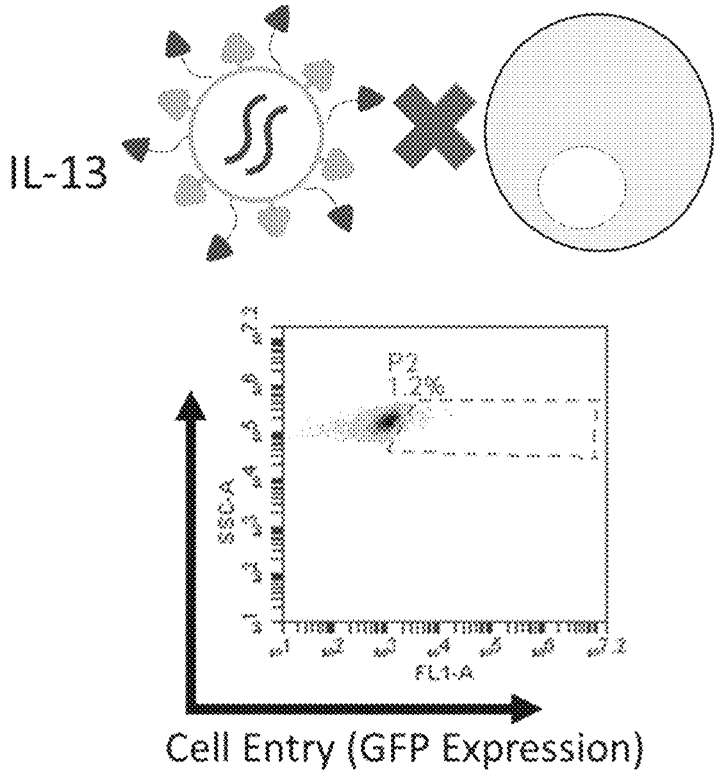
Figure 8:
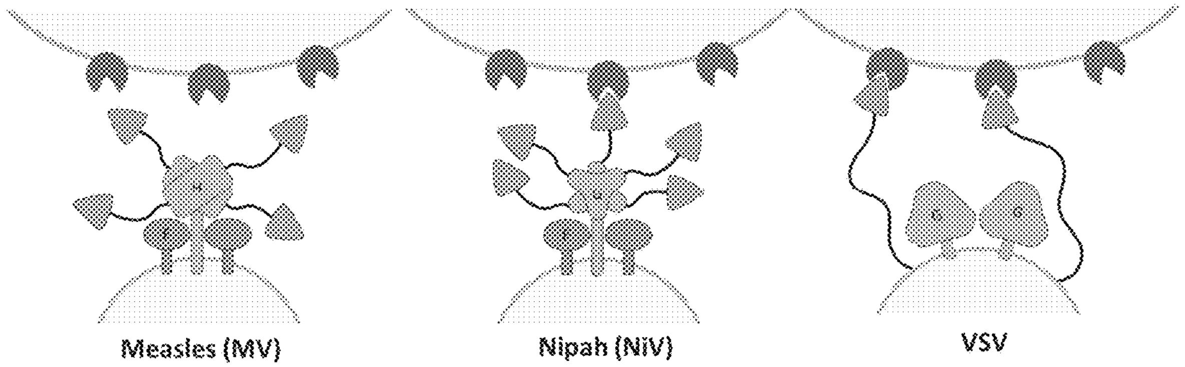
FIG. 8 depicts three exemplary retroviruses, each comprising a different viral envelope protein.

A lentivirus comprising an interleukin-13 (IL-13) extracellular targeting domain was generated, as described in Example 1. The IL-13 extracellular targeting domain consisted of full-length IL-13 protein connected to an IgG4 hinge linker protein linker and a PDGFR transmembrane domain comprising a truncated cytoplasmic tail (PDGFR transmembrane domain: VVVISAILALVVLTIISLIILIMLWQKKPR (SEQ ID NO: 28)). When the resultant viruses were mixed with Jurkat cells expressing the IL-13Rα1 receptor, efficient transduction was observed, with 85.2% of the cells expressing the GFP reporter after mixing (FIG. 7A). When the same viruses were mixed with cells not expressing any IL-13 receptors, minimal infection was observed (FIG. 7B).

Figure 12:
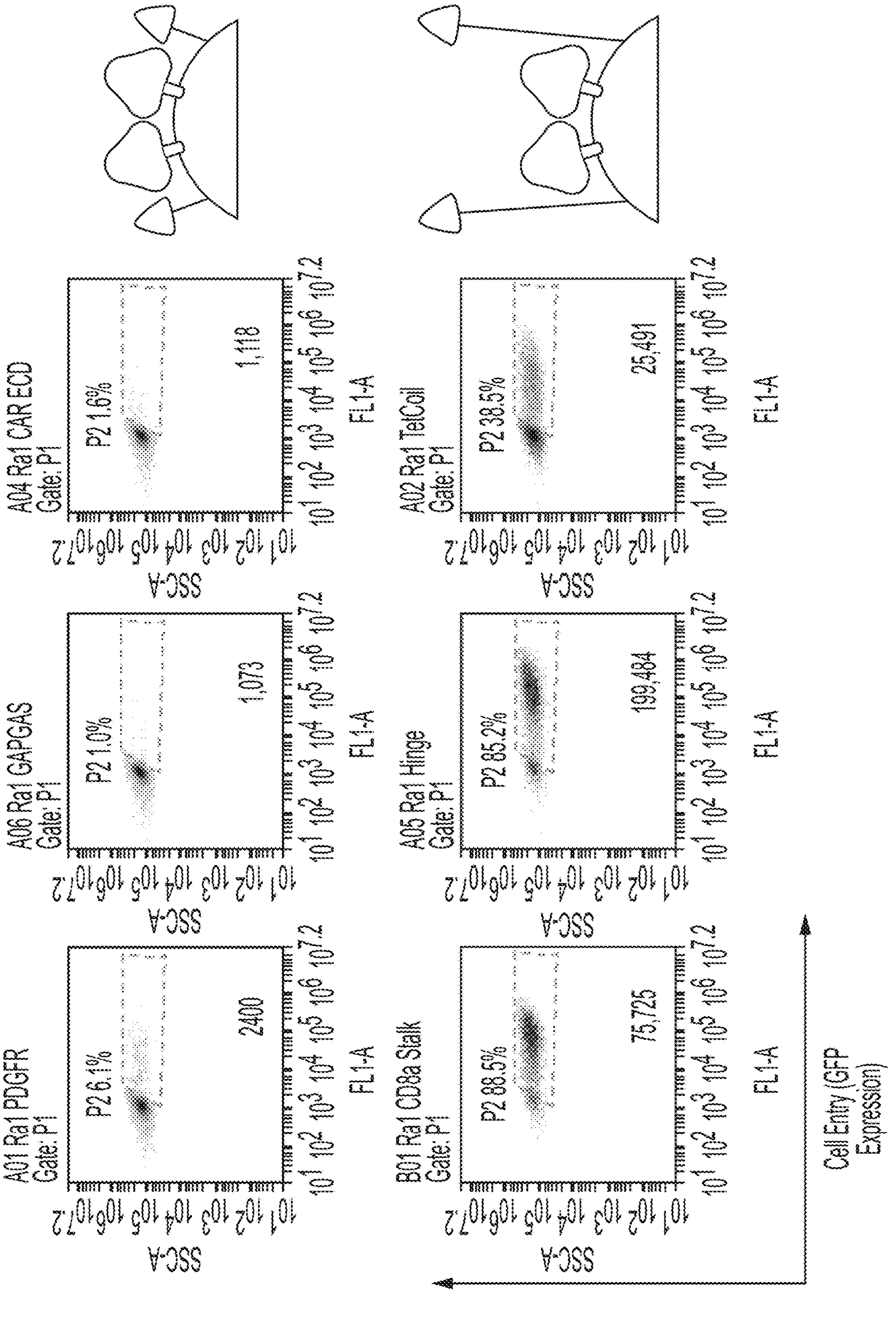
FIG. 12 depicts graphs showing the effect of short protein linkers (PDGFR; GAPGAS (SEQ ID NO: 5); CAR ECD; top, left to right) and long protein linkers (CD8a; Hinge domain; tetrameric coiled coil; bottom, left to right) on retroviral entry.

Additional IL-13 expressing lentiviruses were generated with alternative protein linkers to connect the IL-13 extracellular targeting domain to the PDGFR transmembrane domain. Equivalent volumes of all lentiviruses tested were mixed with Jurkat cells bearing the IL13Rα1 receptor and transduction rates were assessed by GFP reporter (FIG. 12).

Short and long protein linkers were tested for their abilities to allow for cell-to-cell interactions between the extracllular targeting domain (IL-13) and the cognate ligand (IL13Rα1 receptor. Lentiviruses comprising short linkers were marginally able to infect Jurkat cells, with PDGFR linker (AVGQDTQEVIVVPHSLPFK (SEQ ID NO: 3)) enabling infection of 6.1% of cells; GAPGAS linker (GAPGAS (SEQ ID NO: 5)) enabling infection of 1.0% of cells; and a CAR ECD linker (ASESKYGPPCPPCP (SEQ ID NO: 10)) enabling infection of 1.6% of cells. Lentiviruses comprising long linkers were highly successful at infecting Jurkat cells, with CD8α stalk linker (ASAKPTTTPAPRPPTPAPTIASQPLSLRPEAARPAAGGAVHTRGLDFAK (SEQ ID NO: 4)) enabling infection of 88.5% of cells; IgG4 hinge linker (ASESKYGPPCPPCPAVGQDTQEVIVVPHSLPFK (SEQ ID NO: 8)) enabling infection of 85.2% of cells; and an oligomerized linker comprising an amino acid sequence that can form a tetrameric coiled coil (e.g., ASGGGGSGELAAIKQELAAIKKELAAIKWELAAIKQGAG (SEQ ID NO: 9)) enabling infection of 38.5% of cells.

Example 3. Generation of Retroviruses that Target CD19

Figure 9:
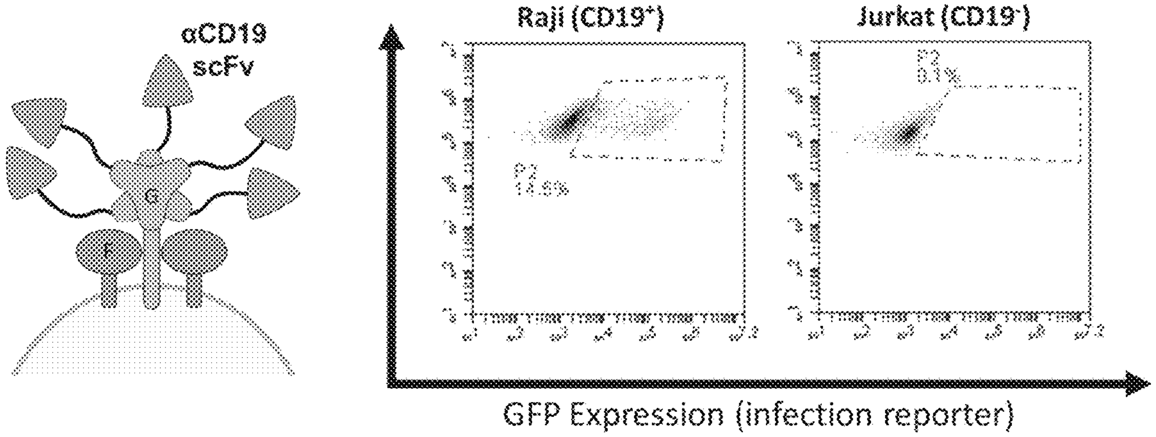
FIG. 9 depicts the ability of a retrovirus comprising a Nipah viral envelope protein and an anti-CD19 scFv antibody to infect and enter $CD19^+$ Raji cells.

A lentivirus pseudotyped with a Nipah virus F protein and a Nipah virus G protein fused to an anti-CD19 scFv was able to transduce $CD19^+$ Raji B cells (cells that express CD19), with 14.5% of cells expressing the GFP reporter after mixing (FIG. 9).

Figure 10A:
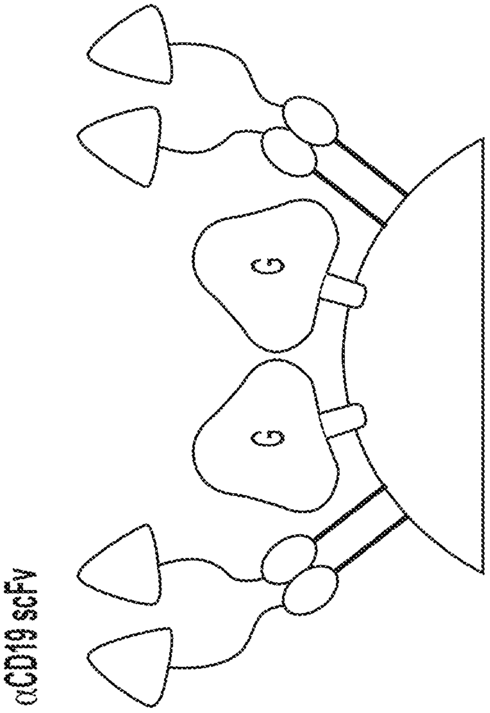
FIGS. 10A-10B depict the ability of a retrovirus comprising a mutated VSV-G viral envelope protein and an anti-CD19 scFv antibody to infect and enter $CD19^+$ Raji cells, while not infecting $CD19^-$ Jurkat cells. A retrovirus comprising a wild-type VSV-G viral envelope protein and an anti-CD19 scFv antibody infects both $CD19^+$ Raji cells and $CD19^-$ Jurkat cells.
Figure 10B:
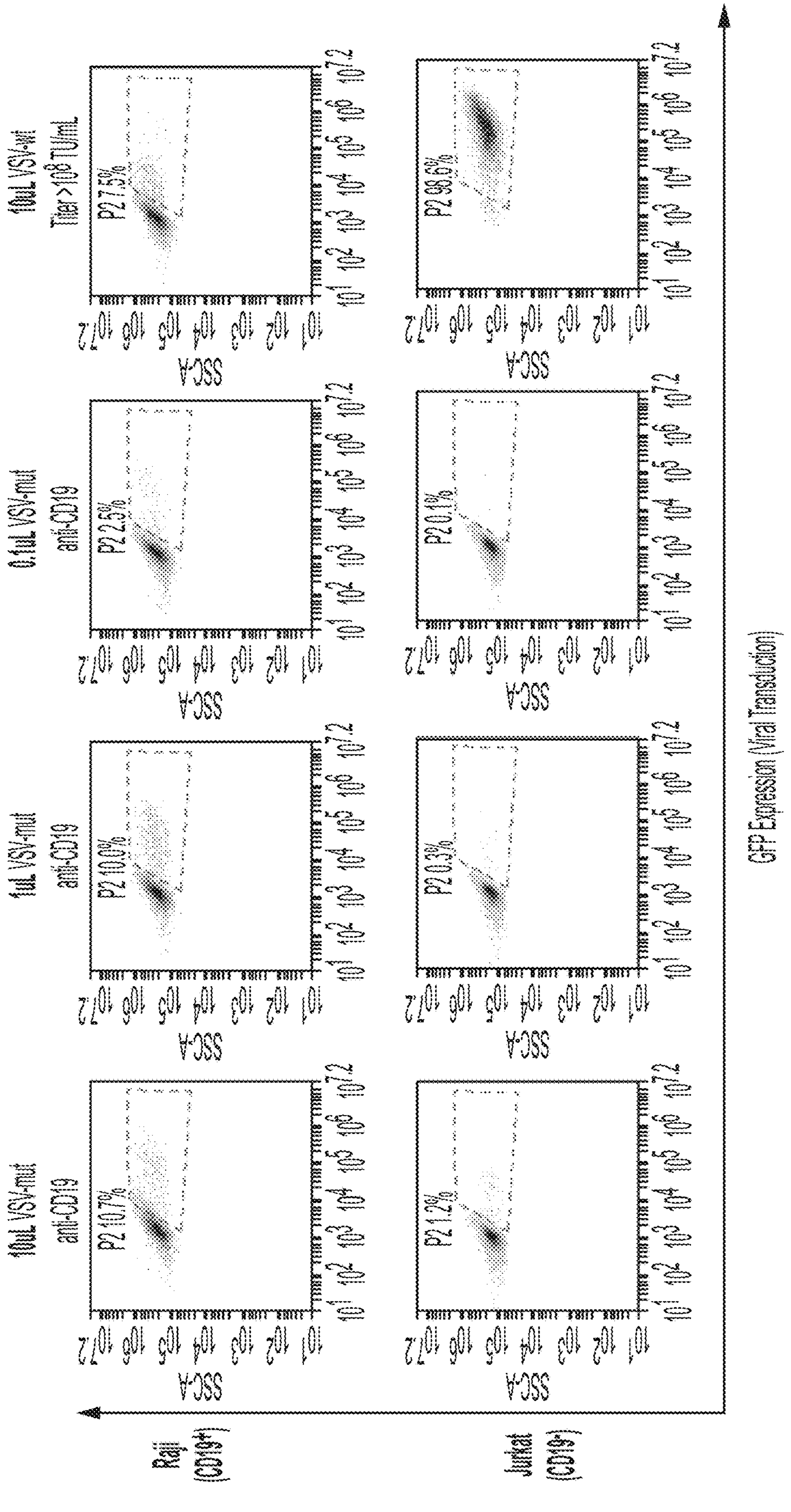
Figure 11:
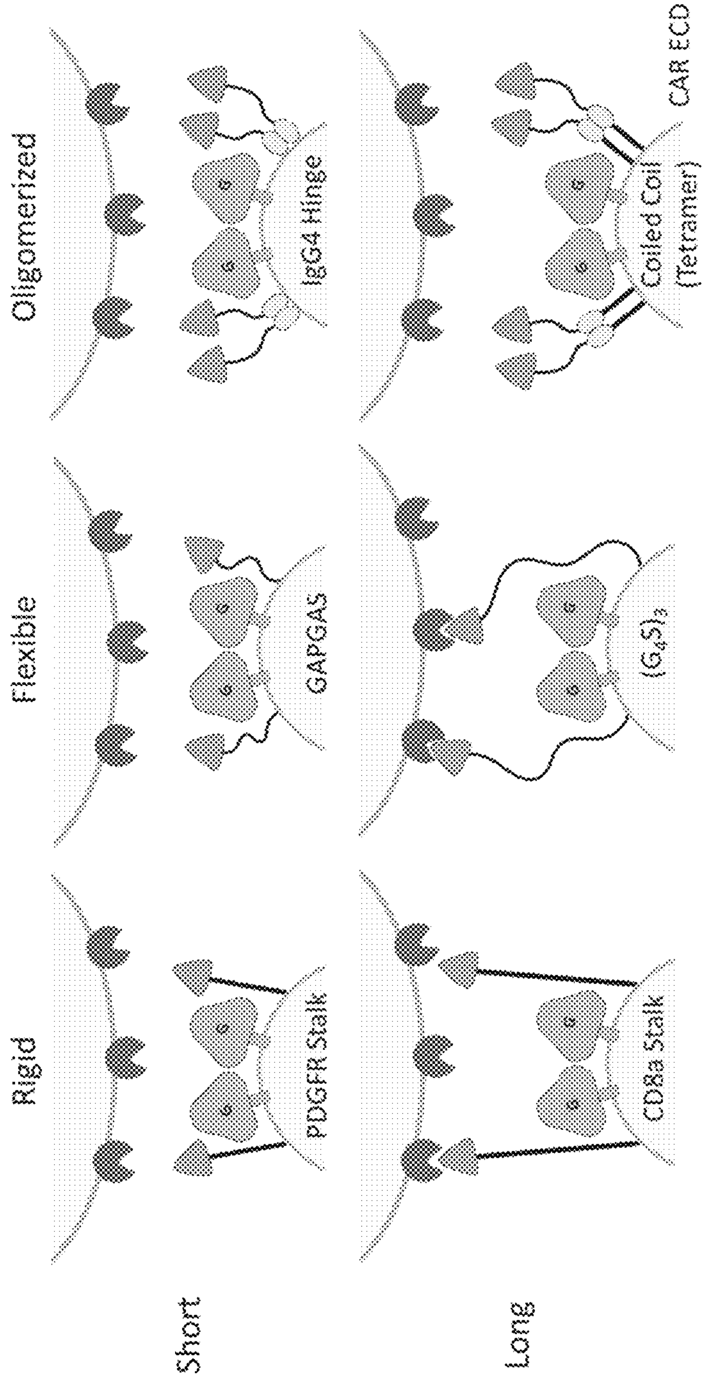
FIG. 11 depicts exemplary linkers for use in nucleic acids and proteins comprising membrane-bound and extracellular targeting domains.

A lentivirus pseudotyped with VSV-mut (mutated VSV-G) and an anti-CD19 scFv fused to an IgG hinge domain, a truncated PDGFR stalk, and PDGFR transmembrane domain was able to transduce $CD19^+$ Raji B cells. Application of 1 μL of VSV-mut lentivirus (200× concentrated) to the $CD19^+$ Raji B cells provided 10.0% infected cells (based on expression of GFP reporter); 10 μL VSV-mut provided 10.7% infected cells. (FIG. 10). The same VSV-mut lentivirus construct did not transduce/infect $CD19^-$ Jurkat cells (cells that do not express CD19), demonstrating that the lentivirus is specific for cells expressing the cognate ligand of its extracellular targeting domain (anti-CD19 scFv).

A lentivirus pseudotyped with VSV-wt (wild-type VSV-G) and an anti-CD19 scFv fused to an IgG hinge domain, a truncated PDGFR stalk, and PDGFR transmembrane domain was able to transduce $CD19^+$ Raji B cells and $CD19^-$ Jurkat cells. This comparative result demonstrates the lentivirus comprising a mutated VSV-G (wherein the mutations diminish the native function of VSV-G protein) is selective for transducing/infecting cells that express a cognate ligand targeted by the extracellular targeting domain of the lentivirus.

Example 4. Ability of Targeted Lentiviruses to Induce T Cell Signaling

Figure 13:
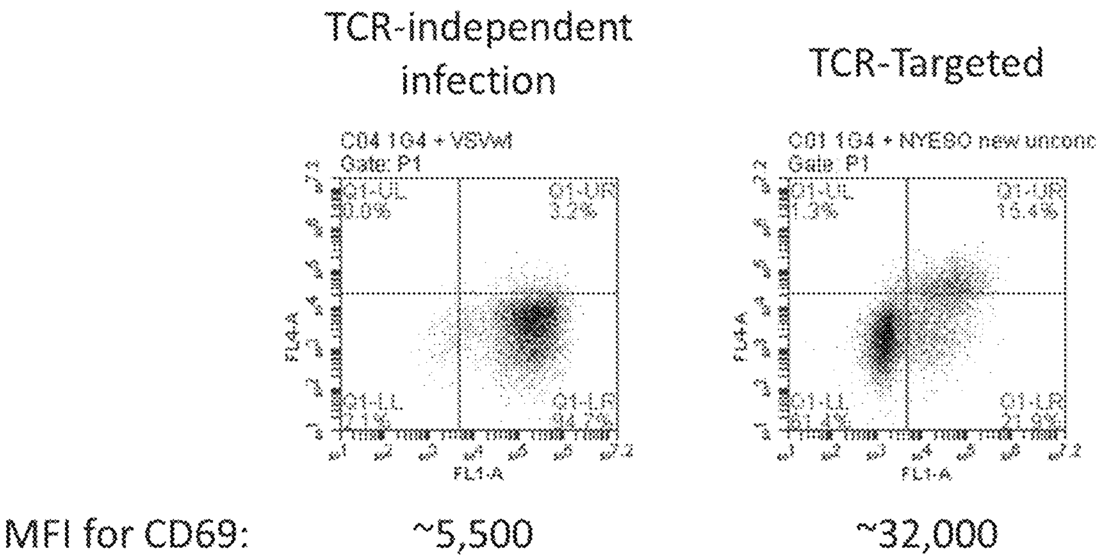
FIG. 13 depicts graphs showing that retroviruses comprising mutated VSV-G viral envelope proteins activate T cell signaling (right panel) and that retroviruses comprising wild-type VSV-G viral envelope proteins do not activate T cell signaling (left panel), as determined by expression of CD69.
Figure 14:
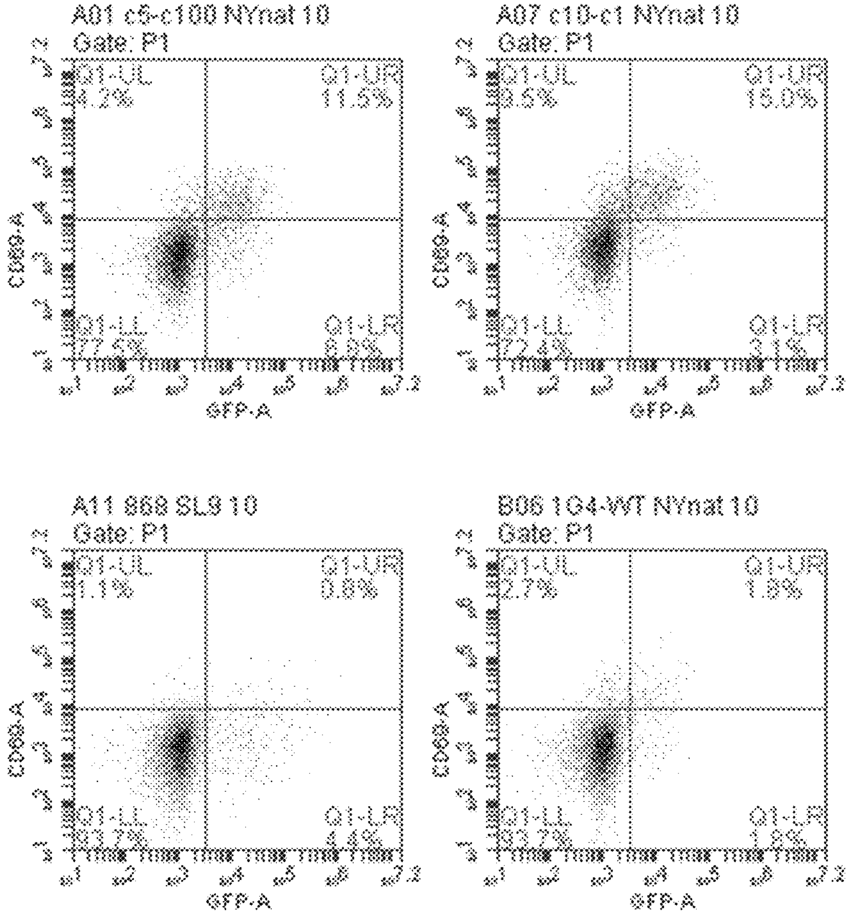
FIG. 14 depicts graphs showing that retroviruses having variable affinities between their extracellular targeting domains and a T cell cognate ligand are able to activate T cell signaling.

Viruses were assessed to determine whether infection via TCR targeting resulted in evidence of TCR signaling. While non-targeted VSV-wt viruses efficiently infected T cells, they did not activate T cells, as assessed by CD69 expression levels, compared to controls (FIG. 13, left panel). However, when HLA-A2-NYESO-1 displaying viruses were used to target Jurkat T cells expressing the high-affinity wild-type 1G4 TCR, upregulation of CD69 was observed in transduced cells, indicating TCR signaling occurred during infection (FIG. 13, right panel). These results were replicated when mixing HLA-A2-NYESO-1 displaying viruses with T cells expressing the lower-affinity mutant 1G4 TCR constructs described in Example 1 (FIG. 14)

Figure 15:
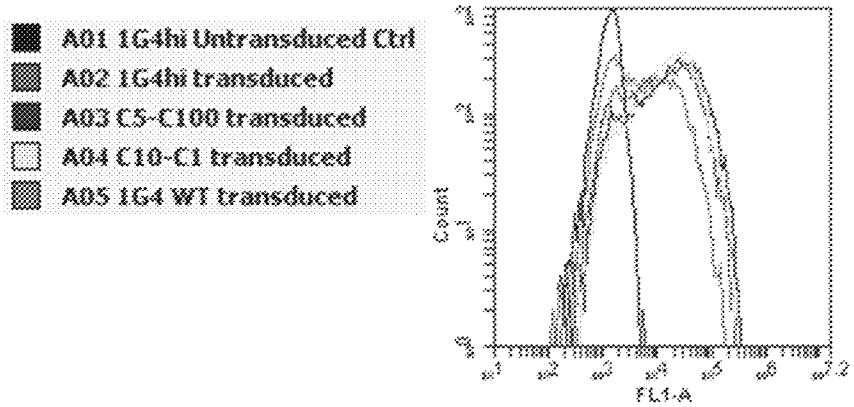
FIG. 15 depicts graphs showing the ability of retroviral entry into target cells at variable affinities, from picomolar to micromolar binding affinities, between an extracellular targeting domain and its cognate ligand.
Figure 15:
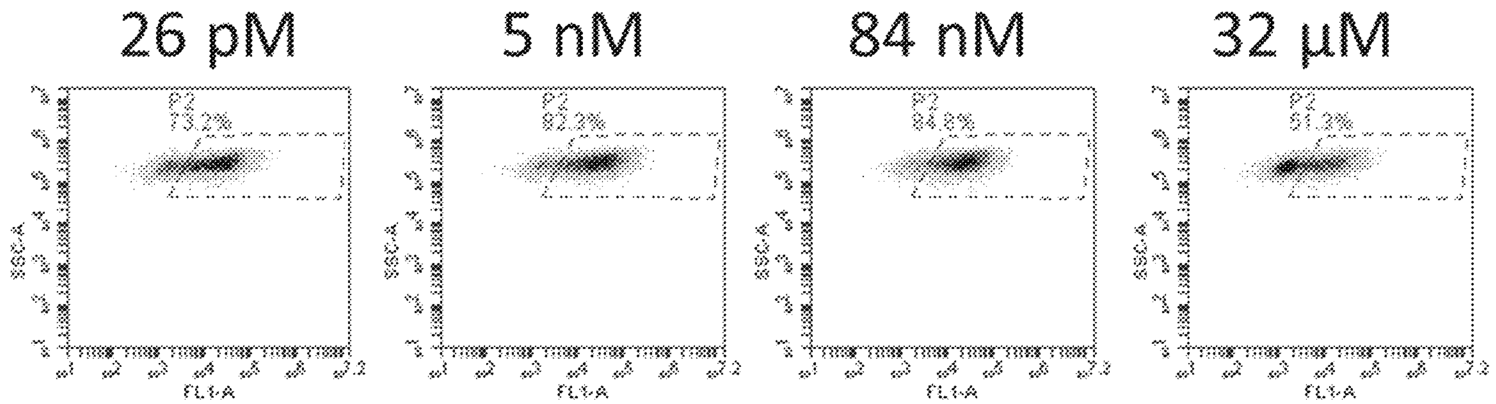

Example 5. Lentiviral Transduction Through the TCR at Physiological Affinities A population of Jurkat T cells was purified on the basis of expression of IG4 TCR before being contacted with HLA-A2-NYESO-1 displaying viruses. The viruses efficiently transduced the purified populations of Jurkat T cells expressing each of the affinity variants of the 1G4 TCR, based on expression of the GFP reporter (FIG. 15). A 32 μM binding affinity between NYESO-1 antigen and an IG4 TCR variant provided 51.3% transduction; a 84 nM binding affinity between NYESO-1 antigen and an IG4 TCR variant provided 84.8% transduction; a 5 nM binding affinity between NYESO-1 antigen and an IG4 TCR variant provided 82.3% transduction; and a 26 nM binding affinity between NYESO-1 antigen and an IG4 TCR variant provided 73.2% transduction.

Figure 16A:
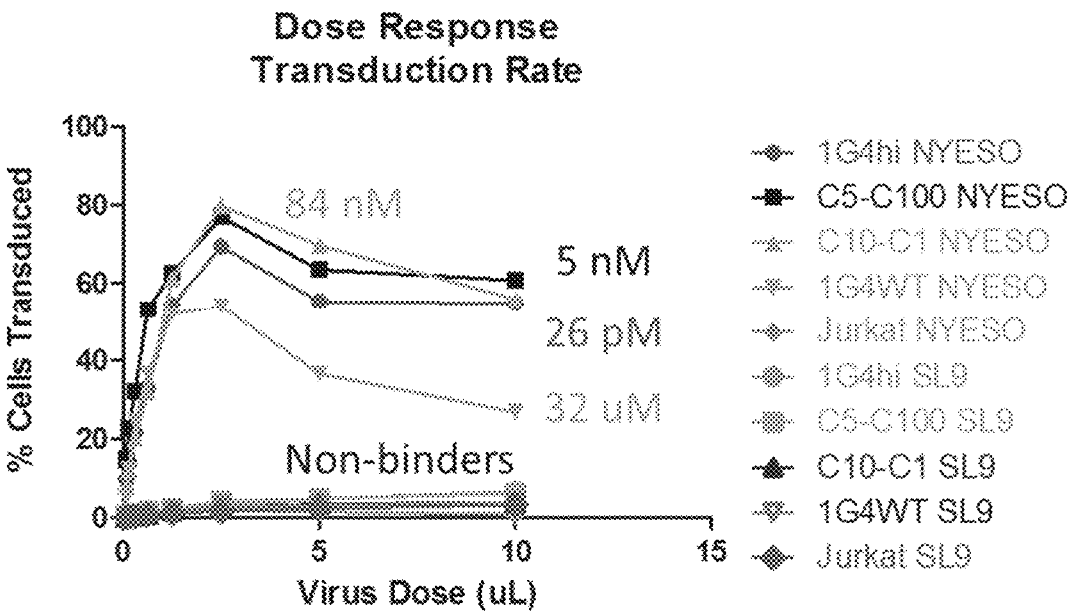
FIGS. 16A-16B depict graphs demonstrating the ability of retroviral entry into target cells at varying concentrations of virus.
Figure 16B:
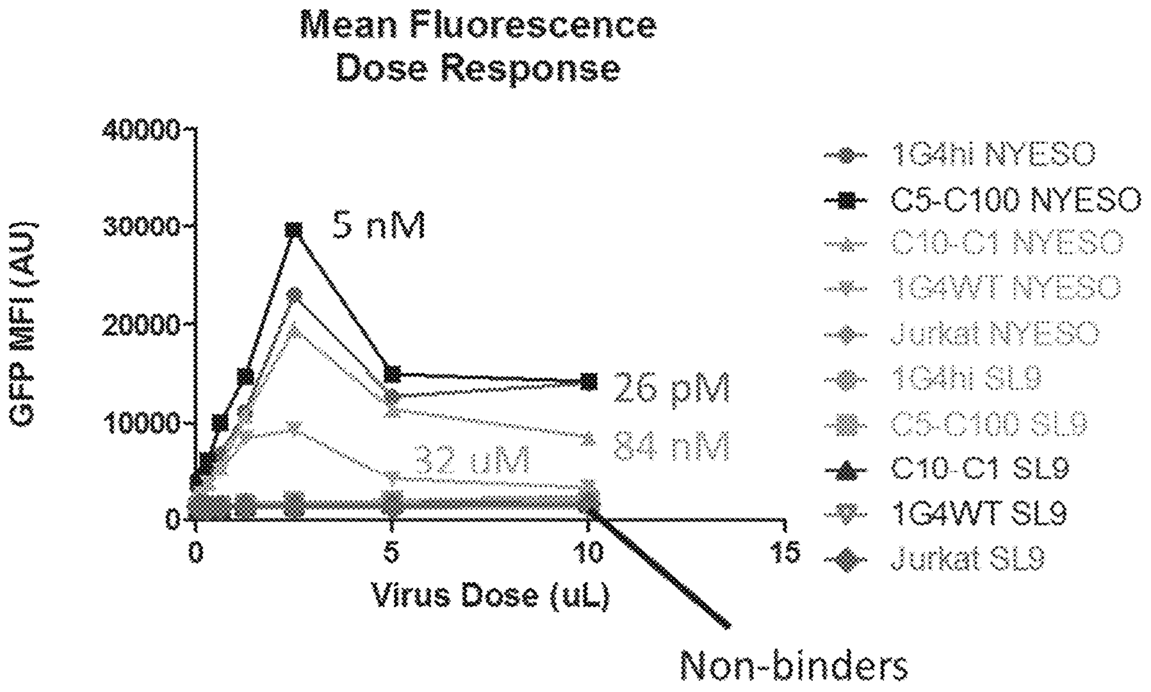

The differences among different IG4 TCR affinity variants were further investigated by performing a dose response to incubate varying amounts (0.5-10 μL of virus) of the HLA-A2-NYESO-1 displaying viruses with cells. NYESO-1 displaying lentiviruses transduce IG4-expressing T cells, even at high viral load (FIG. 16A). Conversely, SL-1 displaying lentiviruses (negative controls) do not transduce IG4-expressing T cells (SL-1 and IG4 TCR are not cognate binding partners).

Figure 17:
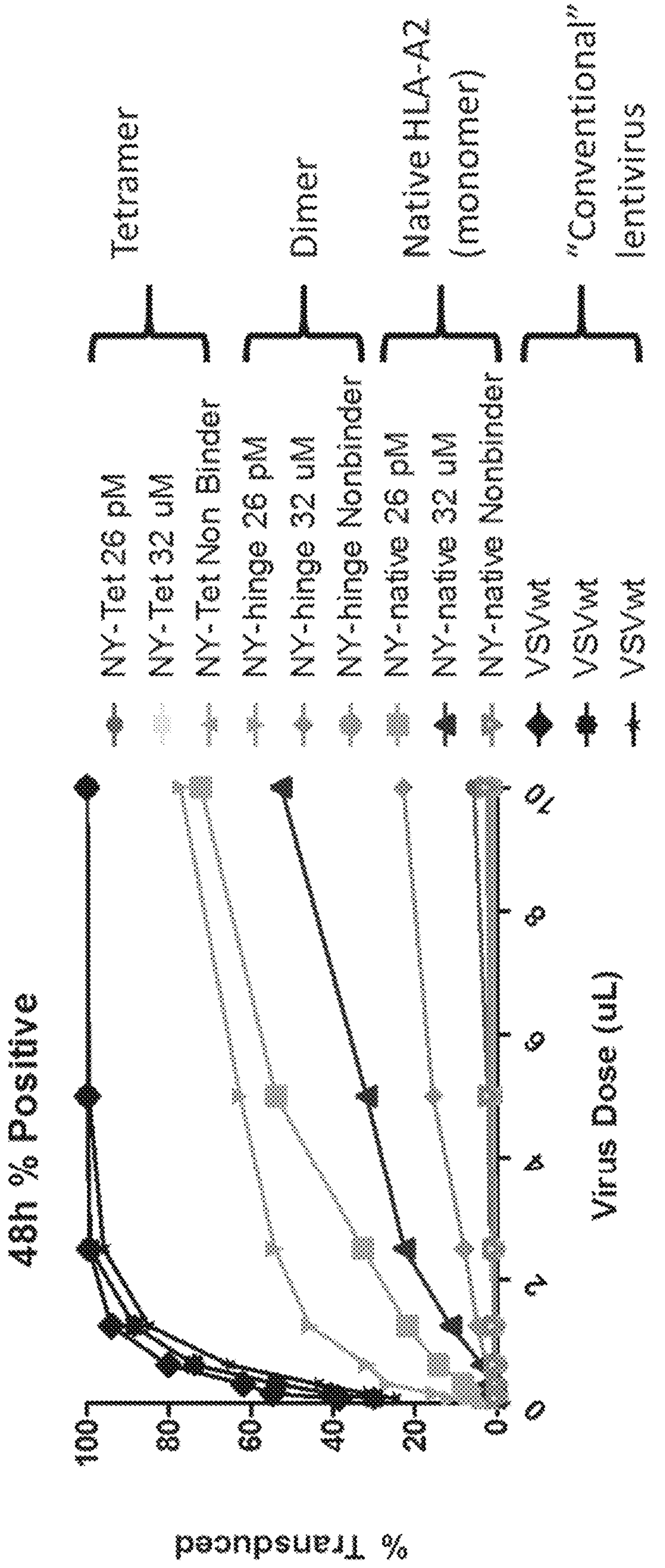
FIG. 17 depicts a graph that demonstrates the impact of protein linker oligomerization on retroviral transduction.

The protein architecture of the membrane-bound NYESO-1 targeting protein was altered to test the ability of oligomerized NYESO-1 displaying constructs to transduce T cells. NYESO-1 displaying expressing lentiviruses were generated with alternative protein linkers to connect the NYESO-1 extracellular targeting domain to transmembrane domain were generated (a protein linker comprising the IgG4 hinge (dimer); and an oligomerized linker comprising an amino acid sequence that can form a tetrameric coiled coil (tetramer)). As demonstrated in FIG. 17, lentiviruses expressing these alternative architectures were able transduce T cells expressing the 26 pM and 32 μM IG4 TCR variants.

Example 6. Virus Binding Assay

Figure 18A:
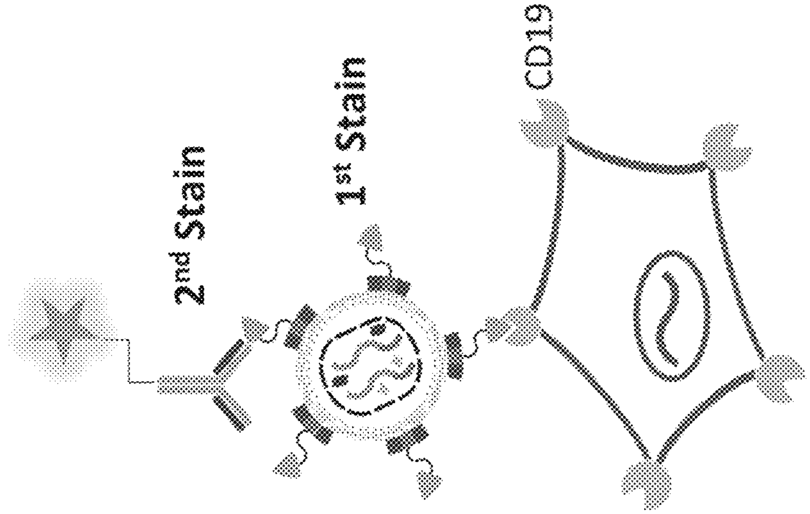
FIGS. 18A-18B depict the ability to detect a binding interaction between a retrovirus comprising an anti-CD19 scFv antibody and a target cell comprising CD19 using a fluorescently labeled antibody that binds to the retrovirus.
Figure 18B:
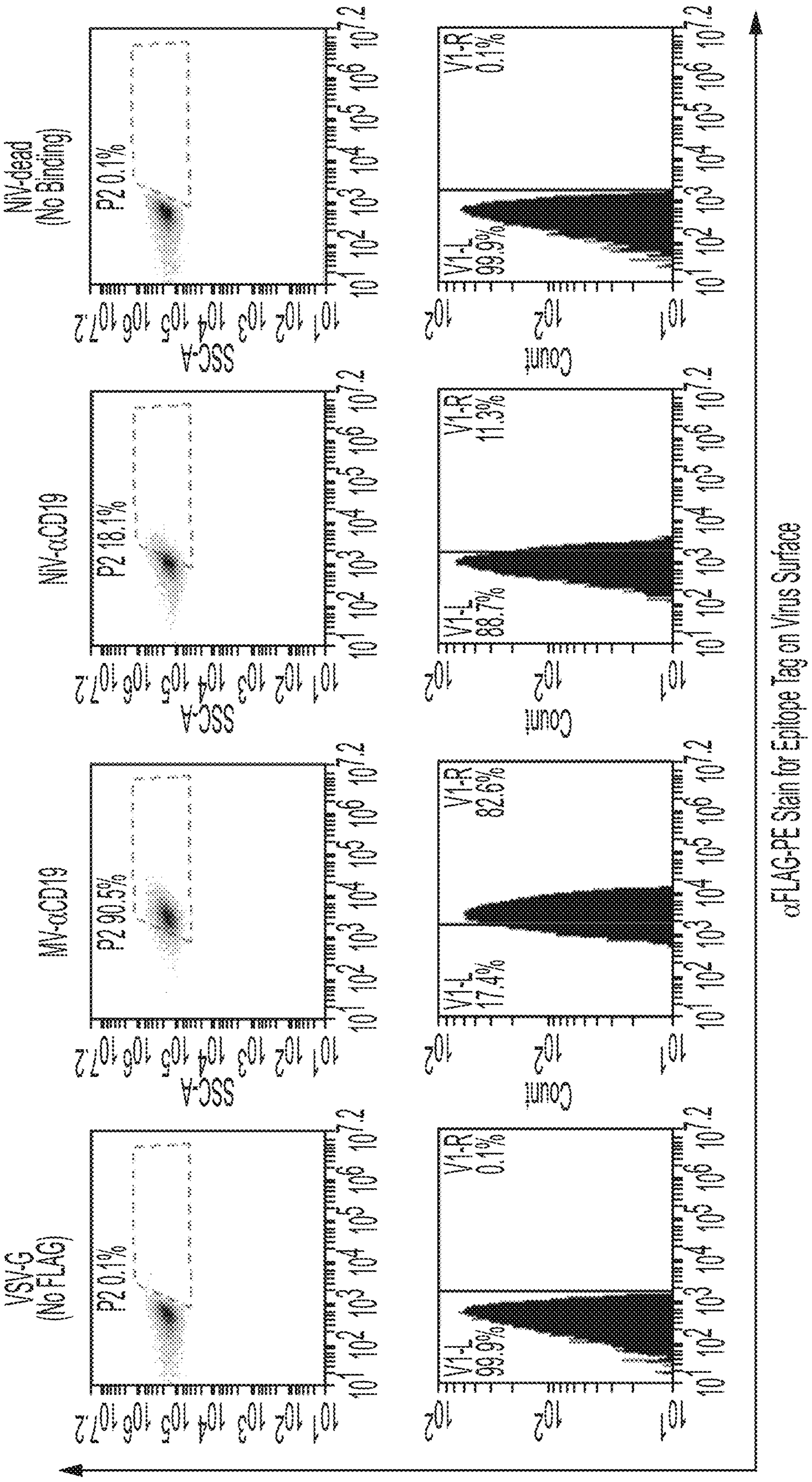

Viruses were pseudotyped with either (1) wild-type VSV-G (VSV-G); (2) measles virus F protein and receptor-blinded H protein fused to an anti-CD19 scFv and a FLAG tag (MV-αCD19); (3) Nipah virus F protein and receptor-blinded G protein fused to an anti-CD19 scFv and a FLAG tag (NiV-αCD19); or (4) Nipah virus F and receptor-blinded G protein with a FLAG tag but no scFv (NiV-dead). Each of these viruses was mixed with $CD19^+$ Raji B cells and subsequently exposed to a fluorescently-labeled antibody against the FLAG tag. As demonstrated in FIGS. 18A-18B, the viruses that expressed an anti-CD19 scFv (MV-αCD19 and NiV-αCD19) bound to the Raji B cells. The viruses that did not express an anti-CD19 scFv (VSV-G and NiV-dead) did not bind to the Raji B cells.

Example 7. Screening a Library of Retroviruses Against Population of T Cells

A library of retroviruses ($10^7$-$10^{10}$ unique retroviruses) comprising a mutated VSV-G envelope protein, a non-viral membrane-bound protein comprising a MHC membrane-bound domain, a variable IL-13 extracellular targeting domain, and a GFP reporter.

First, a library of nucleic acids encoding unique non-viral membrane-bound proteins comprising a MHC membrane-bound domain and a variable IL-13 extracellular targeting domain, is prepared using PCR primers that include degenerate codons at positions known to interact with IL-13 receptors and and induce random mutagenesis in the IL-13 extracellular targeting domain. The resulting nucleic acid constructs are assembled into viral transfer plasmids with fluorescent reporters by standard molecular cloning techniques. These plasmids ("transfer plasmids"), along with helper plasmids and an envelope plasmid encoding mutated VSV-G envelope protein (or an equivalent pseudotype) are transfected into retroviruses to generate the library of retroviruses. The viruses are purified and mixed with populations of cells (e.g. T cell lines, HEK293 cell lines) that express an IL-13 receptor of interest. The viruses are incubated with the populations of cells at an appropriate temperature (e.g., 37° C.) for an appropriate period of time (e.g., 1-48 hours). Mixing is performed in standard cell culture media with hexadimethrine bromide. After 24-48 hours, the cells are sorted based on the expression of the GFP reporter. High-expressing cells are retained and the sorting process is repeated as needed. After these rounds of selection by sorting, the retained cells are lysed and the cellular RNA and DNA are isolated for analysis using next-generation sequencing methods to determine which IL-13 variants were able to mediate viral entry.

Example 8. Generation of Additional Retroviruses that Targets Antigen-Specific T Cells Additional targeted lentiviruses were generated using the protocols described in Example 1.

Figure 19:
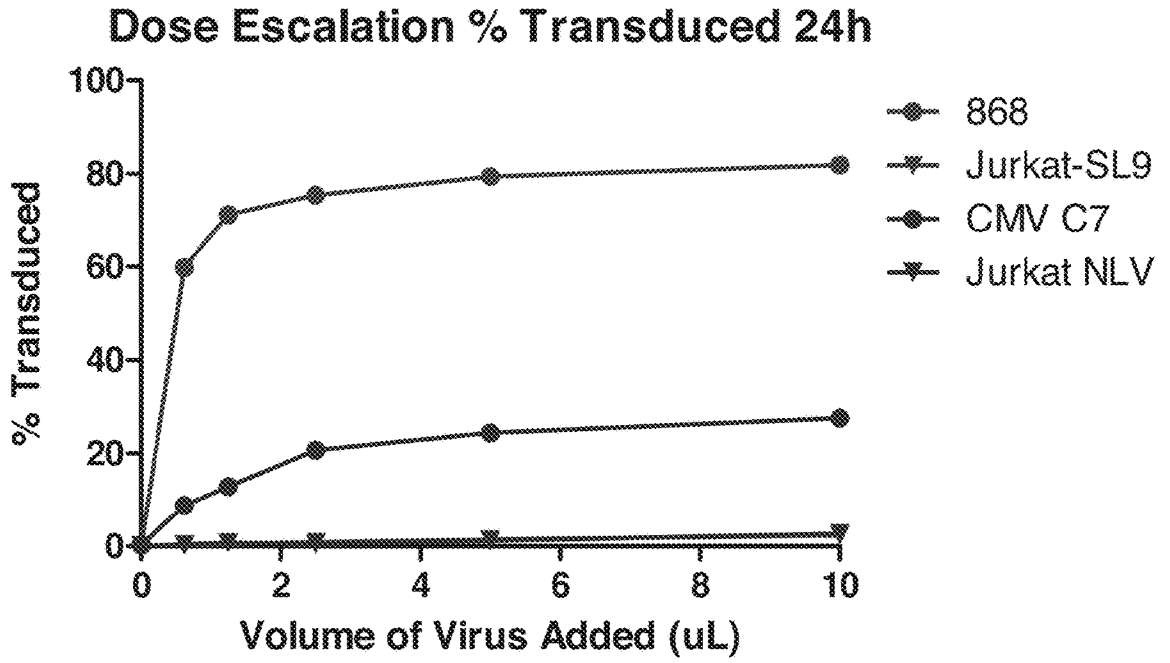
FIG. 19 depicts the ability of SL9 peptide displaying lentiviruses to transduce 868 TCR-expressing T cells ('868') and the ability of CMV NLV peptide displaying lentiviruses to transduce C7 TCR-expressing T cells ('CMV C7').
Figure 20:
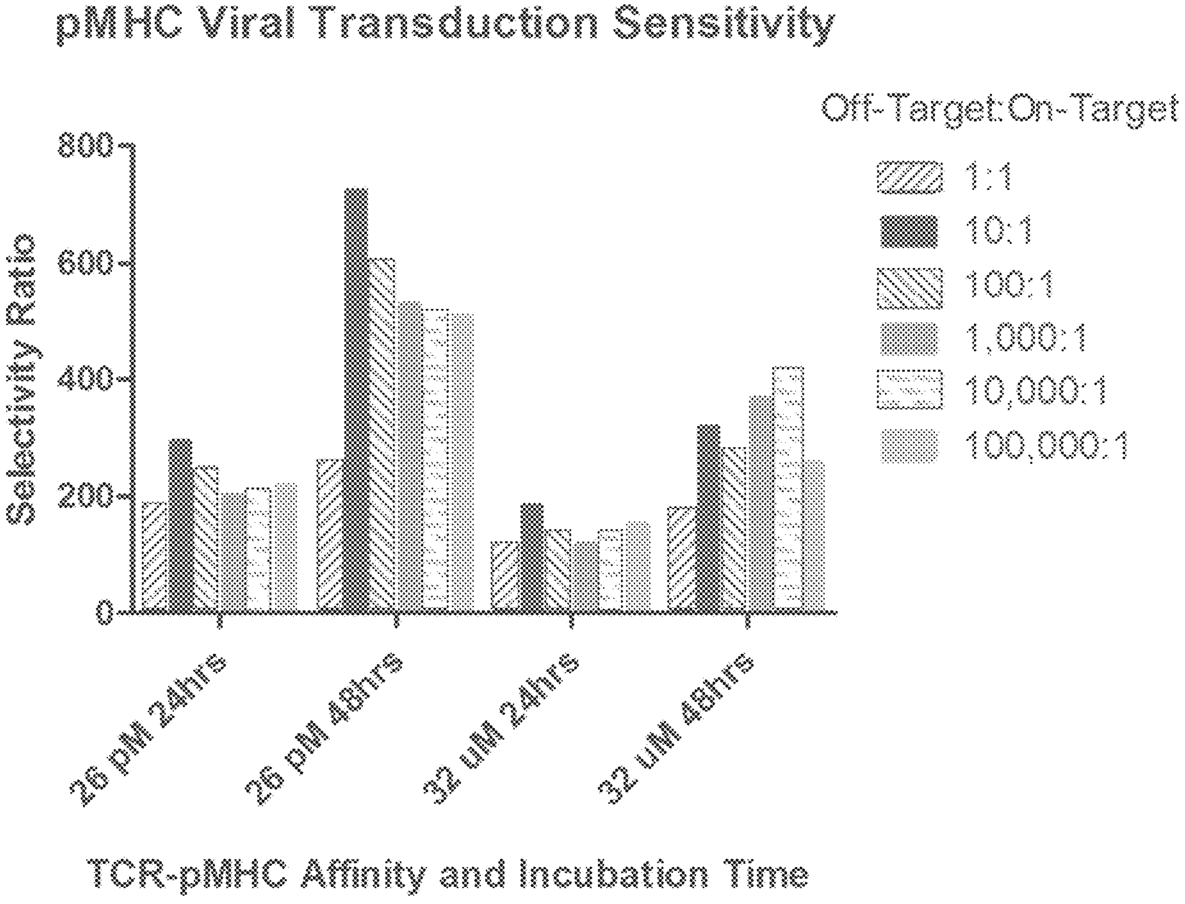
FIG. 20 depicts the ability of NYESO-1 displaying lentiviruses to selectively transduce T cells (target cells) expressing an IG4 T cell receptor (TCR) variant (binding affinities of ~26 pM or ~32 μM for NYESO-1) relative to cells not expressing an IG4 TCR (off-target) at ratios of off-target cells to target cells as high as 100,000:1.

As shown in FIG. 19, mixing (i) lentivirus comprising a mutated VSV-G envelope protein and pMHC displaying a SL9 peptide and (ii) 868 TCR-expressing T cells demonstrated that the viruses were able to transduce and infect T cells even at low amounts of added virus (~70% transduction at 1 μL of virus). Conversely, mixing of these viruses with off-target Jurkat cells led to low levels of transduction (less than 5% up to 10 μL of virus added). A similar experiment As also shown in FIG. 19, mixing (i) lentivirus comprising a mutated VSV-G envelope protein and pMHC displaying a cytomegalovirus (CMV) NLV peptide and (ii) C7 TCR-expressing T cells demonstrated that the viruses were able to transduce and infect T cells (~25% transduction at 10 μL of virus). Conversely, mixing of these viruses with off-target Jurkat cells led to low levels of transduction (less than 5% up to 10 μL of virus added).

Example 9. Generation of Retroviruses Comprising Targeted pMHCs Stabilized by Disulfides Additional targeted lentiviruses were generated using the protocols described in Example 1. These additional lentiviruses further comprised a disulfide situated within the pMHC in order to stabilize the structure of the pMHC.

Figure 21:
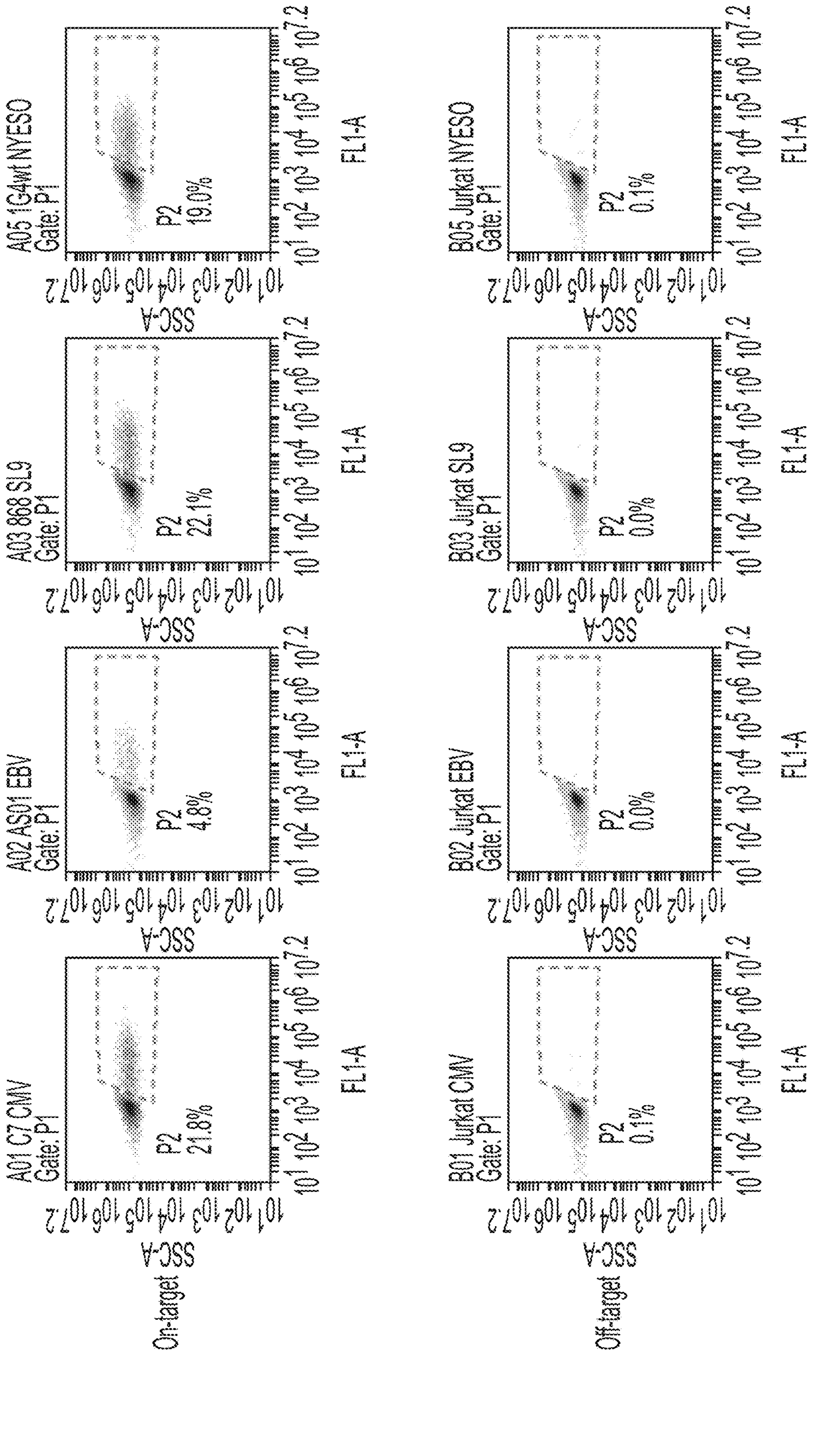
FIG. 21 depicts the ability of lentiviruses displaying varying targeting peptides (CMV NLV; EBV; SL9; GL9; NYESO-1) to selectively transduce T cells that express targeting peptide-specific TCRs (on-target) relative to T cells that do not express the targeting peptide-specific TCRs (off-target).

As shown in FIG. 21, mixing (i) lentivirus comprising a mutated VSV-G envelope protein and a disulfide-stabilized pMHC displaying a targeting peptide and (ii) target cells expressing a cognate receptor demonstrated that the targeted viruses were able to transduce and infect target cells. Conversely, mixing of these targeted viruses with off-target cells caused no, or very limited (0.1%) transduction.

Specifically, a lentivirus comprising a disulfide-stabilized CMV NLV pMHC tranduced on-target C7 TCR-expressing T cells at a 21.8% transduction rate; a lentivirus comprising a disulfide-stabilized EBV pMHC tranduced on-target AS01 cells at a 4.8% transduction rate; a lentivirus comprising a disulfide-stabilized SL9 pMHC tranduced on-target 868 TCR-expressing T cells at a 22.1% transduction rate; and a lentivirus comprising a disulfide-stabilized NYESO-1 pMHC tranduced on-target IG4 TCR-expressing T cells at a 19.0% transduction rate.

Example 10. Targeted Viruses Transduce Primary Cells

Figure 22A:
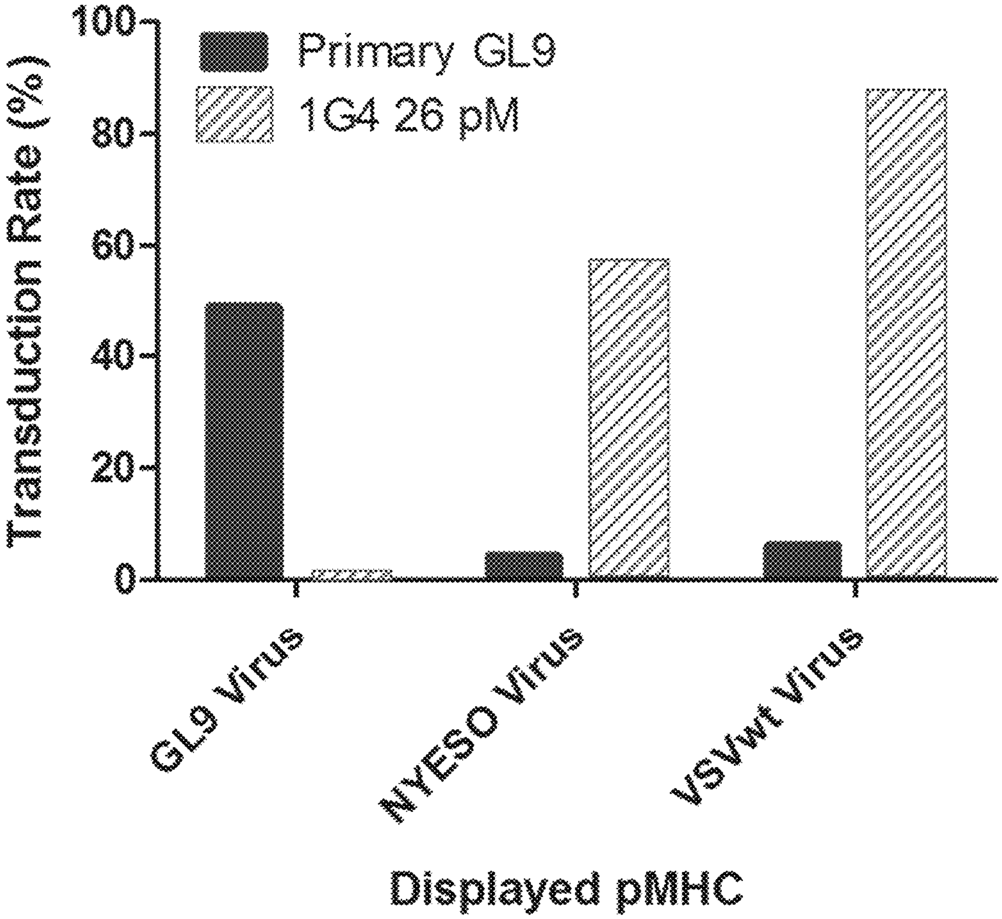
FIGS. 22A-22B depict the ability of varying lentiviruses (GL9 peptide targeting; NYESO-1 peptide targeting; wild-type VSV) to transduce primary T cells that express GL9-specific TCRs and T cells that express an IG4 TCR variant.
Figure 22B:
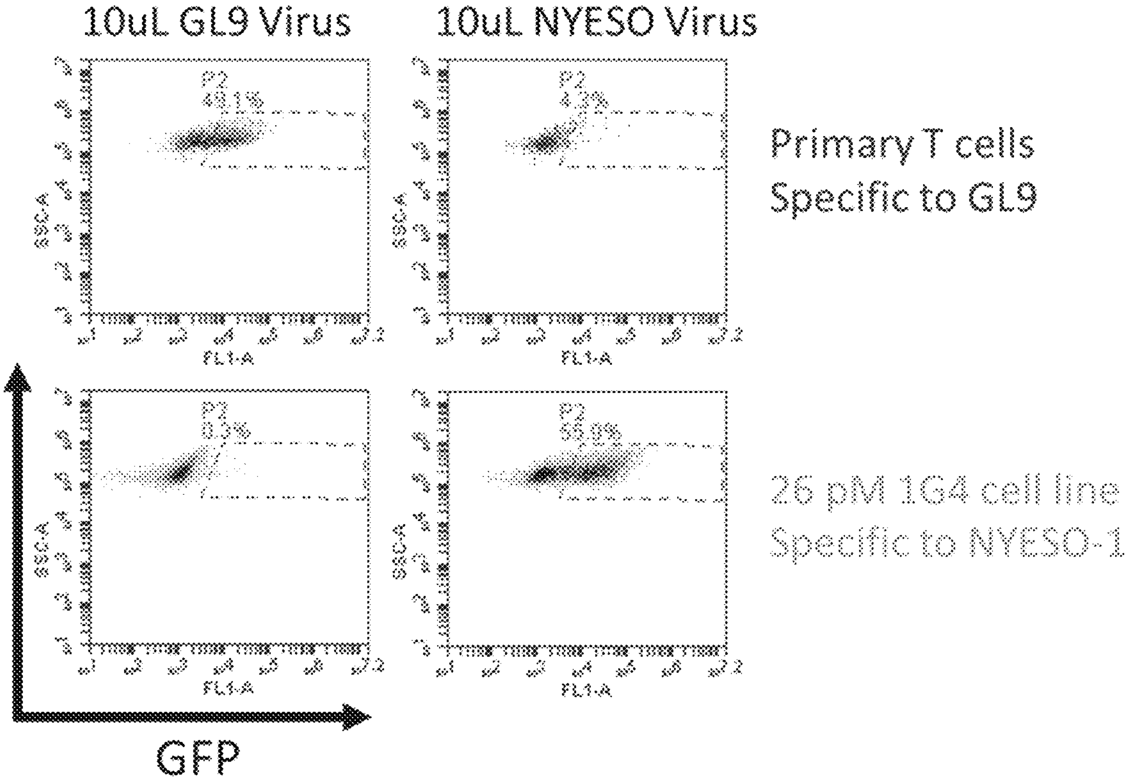

A primary T cell line specific for GL9 (presented by HLA-A2) was specifically and efficiently transduced by viruses having a mutated VSV-G envelope protein and displaying GL9 (FIGS. 22A-22B). About 50% of primary T cells were transduced by these GL9-targeting viruses. Conversely, these GL9-targeting viruses only transduced 0.3% of IG4 TCR-expressing T cells. The IG4 TCR-expressing T cells were specifically and efficiently transduced by viruses having a mutated VSV-G envelope protein and displaying NYESO-1 (55.9% transduction). Furthermore, the targeted virus infects the primary cells more efficiently than a wild-type VSV-G virus. These results indicate that the targeted viruses can even infect unstimulated primary cells.

Figure 23:
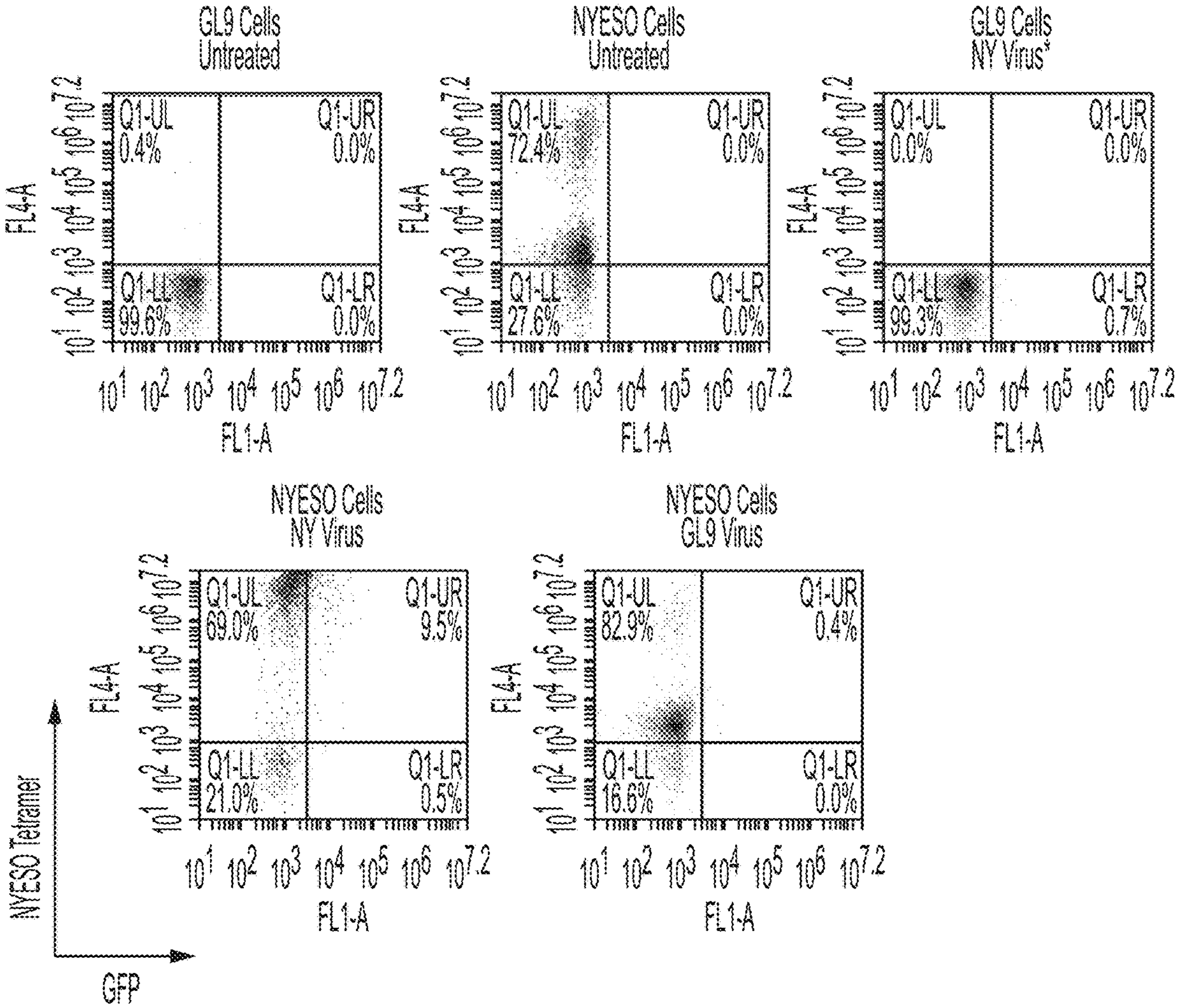
FIG. 23 depicts graphs showing that primary NYESO-1-reactive cells are specifically infected.
Figure 24:
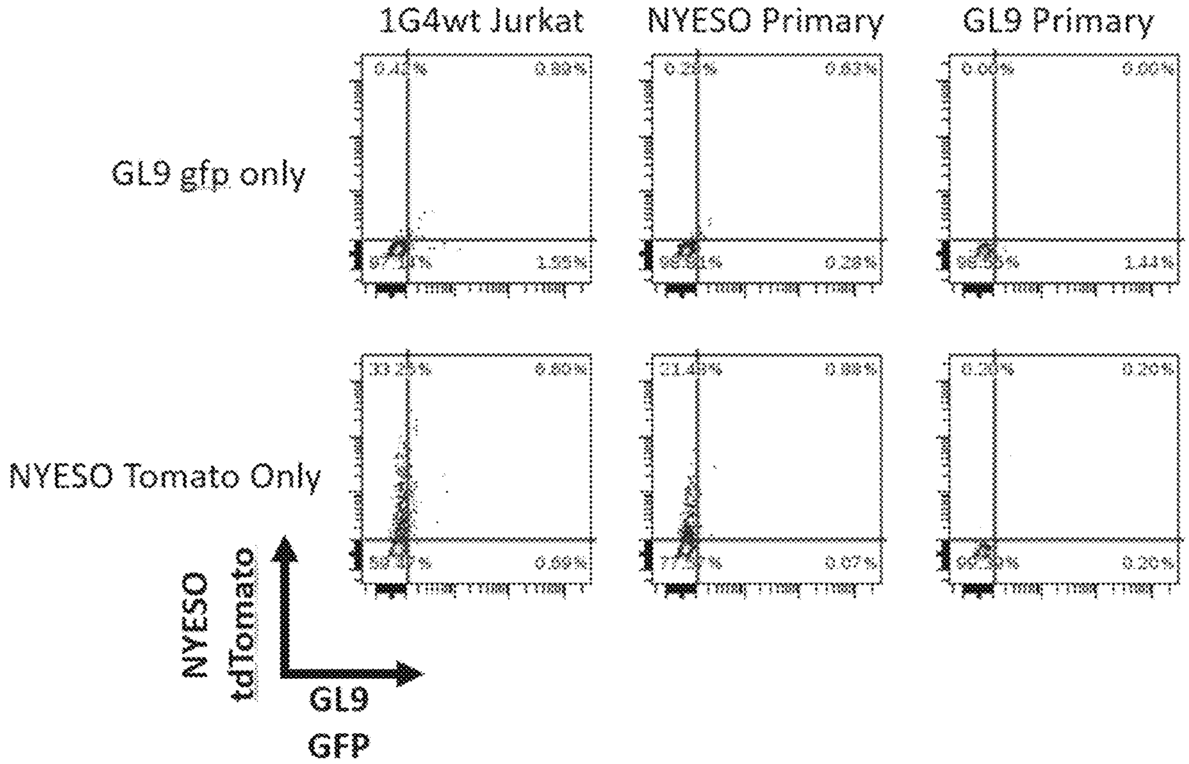
FIG. 24 depicts graphs showing that NYESO-1 targeted virus specifically infects expanded primary cells.

Similarly, a primary T cell line specific for NYESO (presented by HLA-A2) was specifically and efficiently transduced by viruses having a mutated VSV-G envelope protein and displaying NYESO-1 (FIGS. 23-24). Conversely, GL9-targeting viruses were unable to efficiently transduce the primary T cell line specific for NYESO. Collectively, these data demonstrate that primary NYESO-1-reactive cells, including expanded primary cells, can be specifically infected by NYESO-targeted viruses.

Example 11. Generation of Retroviruses Comprising CD80 Domain

Figure 25:
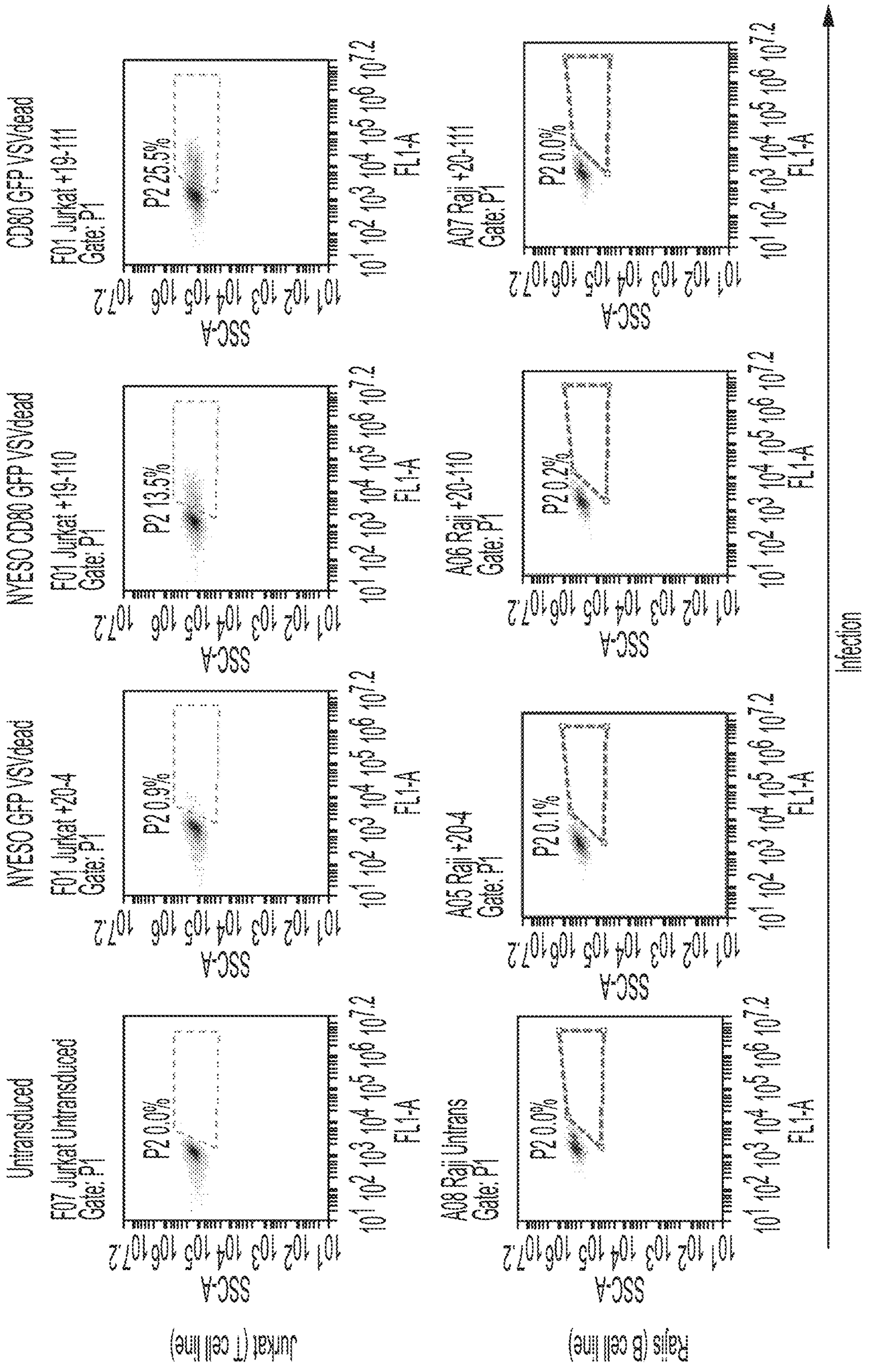
FIG. 25 depicts graphs showing the ability of a retrovirus comprising a mutated VSV-G viral envelope protein and a CD80 domain to specifically infect Jurkat T cells, relative to a B cell line.
Figure 26:
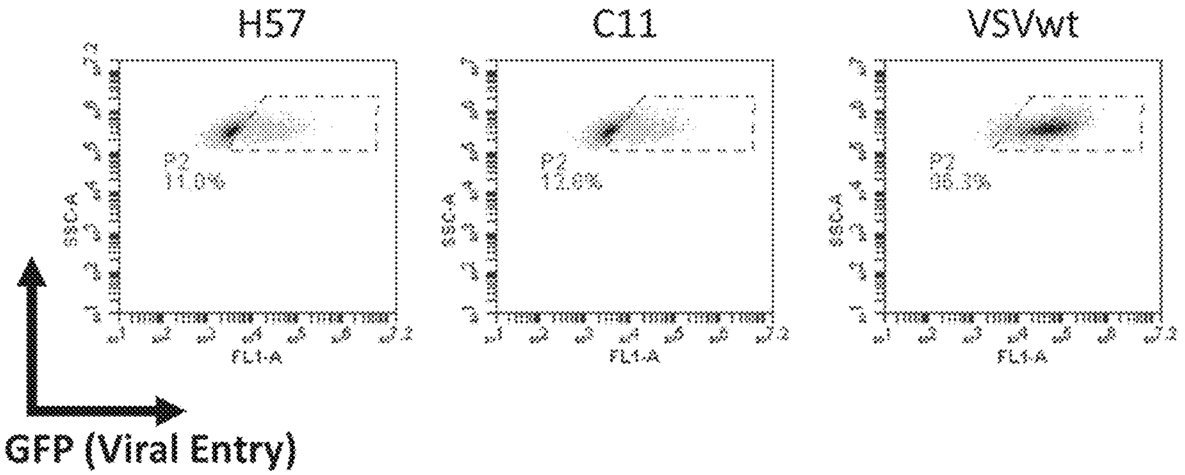
FIG. 26 depicts the ability of retroviruses comprising a mutated VSV-G viral envelope protein and either an anti-TCR-alpha beta antibody (H57) or an anti-CD3 antibody (C11) to infect of TCR-transduced 58−/− mouse cell lines.

A virus pseudotyped with a mutated VSV-G envelope protein and comprising a CD80 extracellular domain was generated using the protocol described in Example 1. This virus was able to specifically and efficiently infect Jurkat T cells (25.5% transduction), relative to B cells (0.0% transduction) (FIG. 25).

Similarly, a virus pseudotyped with a mutated VSV-G envelope protein and comprising a NYESO-1 pMHC and a CD80 extracellular domain was generated using the protocol described in Example 1. This virus was able to specifically and efficiently infect Jurkat T cells (13.5% transduction), relative to B cells (0.2% transduction) (FIG. 25). The presence of the CD80 domain enabled the transduction of this virus into the Jurkat T cells, as demonstrated by the inability of a virus a virus pseudotyped with a mutated VSV-G envelope protein and only comprising the NYESO-1 pMHC to infect these Jurkat T cells (0.9% transduction).

Collectively, these data show that the presence of CD80 on the virus surface mediates specific infection of T cells and demonstrates that CD80 could be used to generally target viruses to T cells.

Example 12. Murine Anti-CD3 Antibody Mediates Infection of TCR-Transduced 58−/− Cells Display of antibodies that are specific to the murine TCR constant region (H57 antibody) or the murine CD3 (2C11 antibody) on the surface of a virus enabled the virsues to infect mouse T cell lines. A virus comprising a mutated VSV-G viral envelope protein and the anti-TCR antibody provided 11.0% transduction of 58$\alpha^-\beta^-$ mouse T hybridoma cells; and a virus comprising a mutated VSV-G viral envelope protein and the anti-CD3 antibody provided 12.8% transduction of $58\alpha^-\beta^-$ mouse T hybridoma cells.

Example 13. Generation of Viruses Comprising Dead Cocal Virus G Protein

A lentivirus was pseudotyped with a cocal virus G protein (Cocal-dead; amino acid comprising SEQ ID NO: 53) comprising mutations to reduce its infectivity. These mutations, at K64Q and R371A of the cocal virus G protein, were analogous to those mutations used in the VSV-dead variant described in Example 1. The cocal-dead virus further comprised a displayed anti-CD19 scFv antibody.

Figure 27:
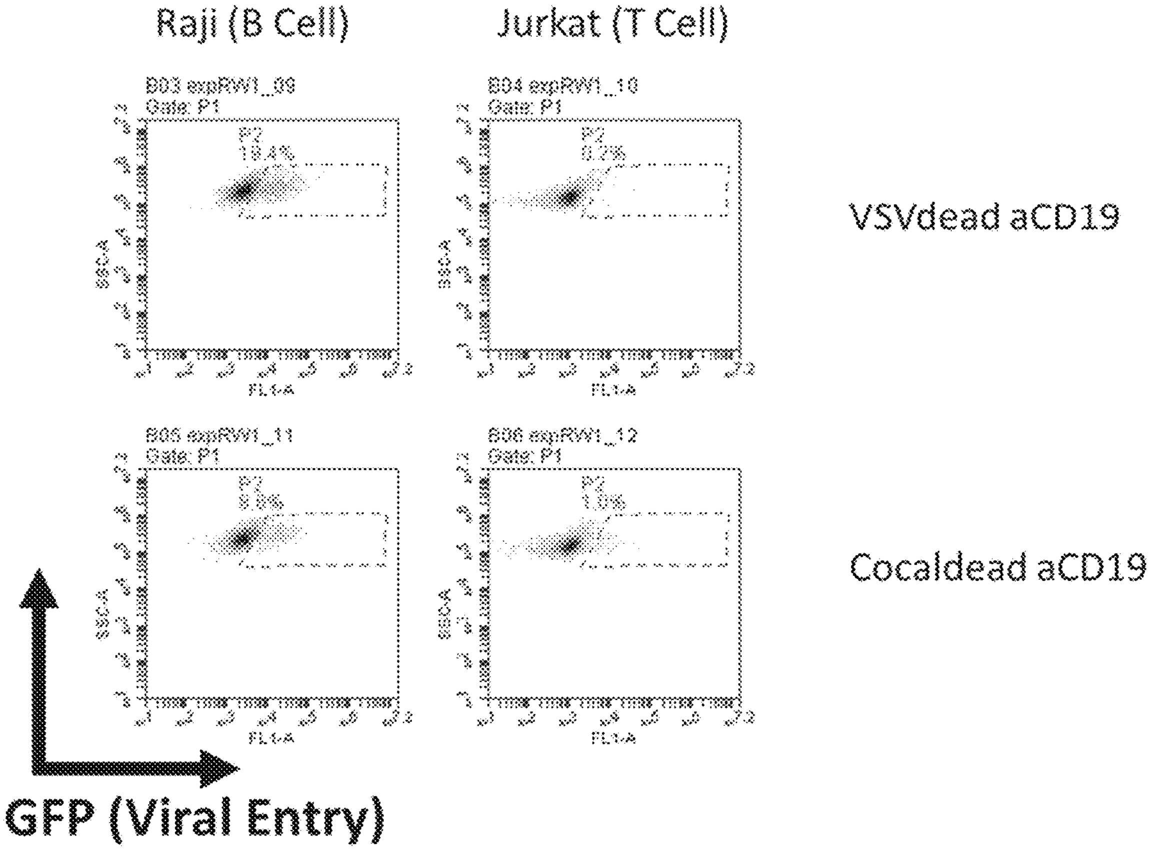
FIG. 27 depicts the ability of a retrovirus comprising either a mutated VSV-G viral envelope protein or a mutated cocal viral envelope protein; and an anti-CD19 scFv antibody to infect and enter $CD19^+$ Raji cells, while not infecting $CD19^-$ Jurkat cells. A retrovirus comprising a wild-type VSV-G viral envelope protein and an anti-CD19 scFv antibody infects both $CD19^+$ Raji cells and $CD19^-$ Jurkat cells.

This cocal-dead virus was able to transduce $CD19^+$ Raji B cells (8.6% transduction), as shown in FIG. 27, in a similar manner as a lentivirus comprising VSV-dead protein and displayed anti-CD19 scFv antibody.

These data demonstrates that the viral targeting strategy is highly robust and that any viral envelope protein (e.g., mutated VSV-G, mutated Nipah envelope, mutated Measles envelope, mutated cocal viral envelope) that can be mutated to reduce its infectivity can be effectively used.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

SEQUENCES

>Kappa leader sequence, amino acid (SEQ ID NO: 1):
METDTLLLWVLLLWVPGSTG

>B2M signal peptide sequence, amino acid (SEQ ID NO: 2):
MSRSVALAVLALLSLSGLEA

>PDGFR short stalk, amino acid (SEQ ID NO: 3):
AVGQDTQEVIVVPHSLPFK

>PDGFR long stalk, amino acid (SEQ ID NO: 4):
ASAKPTTTPAPRPPTPAPTIASQPLSLRPEAARPAAGGAVHTRGLDFAK >Short flexible linker, amino acid (SEQ ID NO: 5):
GAPGAS >Long flexible linker, amino acid (SEQ ID NO: 6):
GAPGSGGGGSGGGGSAS >Short flexible linker, amino acid (SEQ ID NO: 7):
GGGGS >IgG4 hinge domain, amino acid (SEQ ID NO: 8):
ASESKYGPPCPPCPAVGQDTQEVIVVPHSLPFK >Tetrameric coiled coil, amino acid (SEQ ID NO: 9):
ASGGGGSGELAAIKQELAAIKKELAAIKWELAAIKQGAG >Dimeric coiled coil, amino acid (SEQ ID NO: 10):
ASESKYGPPCPPCP >Wild-type VSV-G envelope protein (with leader sequence), DNA sequence (SEQ ID NO: 11):

atgaagtgccttttgtacttagcctttttattcattggggtgaattgcaagttcaccatagttt ttccacacaaccaaaaaggaaactggaaaaatgttccttctaattaccattattgcccgtcaag ctcagatttaaattggcataatgacttaataggcacagccatacaagtcaaaatgcccaagagt cacaaggctattcaagcagacggttggatgtgtcatgcttccaaatgggtcactacttgtgatt tccgctggtatggaccgaagtatataacacagtccatccgatccttcactccatctgtagaaca atgcaaggaaagcattgaacaaacgaaacaaggaacttggctgaatccaggcttccctcctcaa agttgtggatatgcaactgtgacggatgccgaagcagtgattgtccaggtgactcctcaccatg tgctggttgatgaatacacaggagaatgggttgattcacagttcatcaacggaaaatgcagcaa ttacatatgccccactgtccataactctacaacctggcattctgactataaggtcaaagggcta tgtgattctaacctcatttccatggacatcaccttcttctcagaggacggagagctatcatccc tgggaaaggagggcacagggttcagaagtaactactttgcttatgaaactggaggcaaggcctg caaaatgcaatactgcaagcattggggagtcagactcccatcaggtgtctggttcgagatggct gataaggatctctttgctgcagccagattccctgaatgcccagaagggtcaagtatctctgctc catctcagacctcagtggatgtaagtctaattcaggacgttgagaggatcttggattattccct ctgccaagaaacctggagcaaaatcagagcgggtcttccaatctctccagtggatctcagctat cttgctcctaaaaacccaggaaccggtcctgctttcaccataatcaatggtaccctaaaatact ttgagaccagatacatcagagtcgatattgctgctccaatcctctcaagaatggtcggaatgat cagtggaactaccacagaaagggaactgtgggatgactgggcaccatatgaagacgtggaaatt ggacccaatggagttctgaggaccagttcaggatataagtttcctttatacatgattggacatg gtatgttggactccgatcttcatcttagctcaaaggctcaggtgttcgaacatcctcacattca agacgctgcttcgcaacttcctgatgatgagagtttatttttggtgatactgggctatccaaa -continued aatccaatcgagcttgtagaaggttggttcagtagttggaaaagctctattgcctcttttttct ttatcatagggttaatcattggactattcttggttctccgagttggtatccatctttgcattaa attaaagcacaccaagaaaagacagatttatacagacatagagatgaaccgacttggaaagtaa >Wild-type VSV-G envelope protein (with leader sequence), amino acid sequence (SEQ ID NO: 12):
MKCLLYLAFLFIGVNCKFTIVFPHNQKGNWKNVPSNYHYCPSSSDLNWHNDLIGTAIQVKMPKS

HKAIQADGWMCHASKWVTTCDFRWYGPKYITQSIRSFTPSVEQCKESIEQTKQGTWLNPGFPPQ

SCGYATVTDAEAVIVQVTPHHVLVDEYTGEWVDSQFINGKCSNYICPTVHNSTTWHSDYKVKGL

CDSNLISMDITFFSEDGELSSLGKEGTGFRSNYFAYETGGKACKMQYCKHWGVRLPSGVWFEMA

DKDLFAAARFPECPEGSSISAPSQTSVDVSLIQDVERILDYSLCQETWSKIRAGLPISPVDLSY

LAPKNPGTGPAFTIINGTLKYFETRYIRVDIAAPILSRMVGMISGTTTERELWDDWAPYEDVEI

GPNGVLRTSSGYKFPLYMIGHGMLDSDLHLSSKAQVFEHPHIQDAASQLPDDESLFFGDTGLSK

NPIELVEGWFSSWKSSIASFFFIIGLIIGLFLVLRVGIHLCIKLKHTKKRQIYTDIEMNRLGK

>Wild-type VSV-G envelope protein, amino acid sequence (SEQ ID NO: 13):
KFTIVFPHNQKGNWKNVPSNYHYCPSSSDLNWHNDLIGTAIQVKMPKSHKAIQADGWMCHASKW

VTTCDFRWYGPKYITQSIRSFTPSVEQCKESIEQTKQGTWLNPGFPPQSCGYATVTDAEAVIVQ

VTPHHVLVDEYTGEWVDSQFINGKCSNYICPTVHNSTTWHSDYKVKGLCDSNLISMDITFFSED

GELSSLGKEGTGFRSNYFAYETGGKACKMQYCKHWGVRLPSGVWFEMADKDLFAAARFPECPEG

SSISAPSQTSVDVSLIQDVERILDYSLCQETWSKIRAGLPISPVDLSYLAPKNPGTGPAFTIIN

GTLKYFETRYIRVDIAAPILSRMVGMISGTTTERELWDDWAPYEDVEIGPNGVLRTSSGYKFPL

YMIGHGMLDSDLHLSSKAQVFEHPHIQDAASQLPDDESLFFGDTGLSKNPIELVEGWFSSWKSS

IASFFFIIGLIIGLFLVLRVGIHLCIKLKHTKKRQIYTDIEMNRLGK

>VSV-G envelope protein (with leader sequence), DNA sequence (SEQ ID NO: 14):
atgaagtgccttttgtacttagcctttttattcattggggtgaattgcaagttcaccatagttt ttccacacaaccaaaaaggaaactggaaaaatgttccttctaattaccattattgcccgtcaag ctcagatttaaattggcataatgacttaataggcacagccttacaagtcaaaatgccccagagt cacaaggctattcaagcagacggttggatgtgtcatgcttccaaatgggtcactacttgtgatt tccgctggtatggaccgaagtatataacacagtccatccgatccttcactccatctgtagaaca atgcaaggaaagcattgaacaaacgaaacaaggaacttggctgaatccaggcttccctcctcaa agttgtggatatgcaactgtgacggatgccgaagcagtgattgtccaggtgactcctcaccatg tgctggttgatgaatacacaggagaatgggttgattcacagttcatcaacggaaaatgcagcaa ttacatatgccccactgtccataactctacaacctggcattctgactataaggtcaaagggcta tgtgattctaacctcatttccatggacatcaccttcttctcagaggacggagagctatcatccc tgggaaaggagggcacagggttcagaagtaactactttgcttatgaaactggaggcaaggcctg caaaatgcaatactgcaagcattggggagtcagactcccatcaggtgtctggttcgagatggct gataaggatctctttgctgcagccagattccctgaatgcccagaagggtcaagtatctctgctc catctcagacctcagtggatgtaagtctaattcaggacgttgagaggatcttggattattccct ctgccaagaaacctggagcaaaatcagagcgggtcttccaatctctccagtggatctcagctat cttgctcctaaaaacccaggaaccggtcctgctttcaccataatcaatggtaccctaaaatact ttgagaccagatacatcagagtcgatattgctgctccaatcctctcaagaatggtcggaatgat cagtggaactaccacagaagccgaactgtgggatgactgggcaccatatgaagacgtggaaatt -continued ggacccaatggagttctgaggaccagttcaggatataagtttcctttatacatgattggacatg gtatgttggactccgatcttcatcttagctcaaaggctcaggtgttcgaacatcctcacattca agacgctgcttcgcaacttcctgatgatgagagtttattttttggtgatactgggctatccaaa aatccaatcgagcttgtagaaggttggttcagtagttggaaaagctctattgcctctttttct ttatcatagggttaatcattggactattcttggttctccgagttggtatccatctttgcattaa attaaagcacaccaagaaaagacagatttatacagacatagagatgaaccgacttggaaagtaa >VSV-G envelope protein (with leader sequence), amino acid sequence (SEQ ID NO: 15):

MKCLLYLAFLFIGVNCKFTIVFPHNQKGNWKNVPSNYHYCPSSSDLNWHNDLIGTALQVKMPQS

HKAIQADGWMCHASKWVTTCDFRWYGPKYITQSIRSFTPSVEQCKESIEQTKQGTWLNPGFPPQ

SCGYATVTDAEAVIVQVTPHHVLVDEYTGEWVDSQFINGKCSNYICPTVHNSTTWHSDYKVKGL

CDSNLISMDITFFSEDGELSSLGKEGTGFRSNYFAYETGGKACKMQYCKHWGVRLPSGVWFEMA

DKDLFAAARFPECPEGSSISAPSQTSVDVSLIQDVERILDYSLCQETWSKIRAGLPISPVDLSY

LAPKNPGTGPAFTIINGTLKYFETRYIRVDIAAPILSRMVGMISGTTTEAELWDDWAPYEDVEI

GPNGVLRTSSGYKFPLYMIGHGMLDSDLHLSSKAQVFEHPHIQDAASQLPDDESLFFGDTGLSK

NPIELVEGWFSSWKSSIASFFFIIGLIIGLFLVLRVGIHLCIKLKHTKKRQIYTDIEMNRLGK

>I41L/K47Q/R354A VSV-G envelope protein, amino acid sequence (SEQ ID NO: 16):

KFTIVFPHNQKGNWKNVPSNYHYCPSSSDLNWHNDLIGTALQVKMPQSHKAIQADGWMCHASKW

VTTCDFRWYGPKYITQSIRSFTPSVEQCKESIEQTKQGTWLNPGFPPQSCGYATVTDAEAVIVQ

VTPHHVLVDEYTGEWVDSQFINGKCSNYICPTVHNSTTWHSDYKVKGLCDSNLISMDITFFSED

GELSSLGKEGTGFRSNYFAYETGGKACKMQYCKHWGVRLPSGVWFEMADKDLFAAARFPECPEG

SSISAPSQTSVDVSLIQDVERILDYSLCQETWSKIRAGLPISPVDLSYLAPKNPGTGPAFTIIN

GTLKYFETRYIRVDIAAPILSRMVGMISGTTTEAELWDDWAPYEDVEIGPNGVLRTSSGYKFPL

YMIGHGMLDSDLHLSSKAQVFEHPHIQDAASQLPDDESLFFGDTGLSKNPIELVEGWFSSWKSS

IASFFFIIGLIIGLFLVLRVGIHLCIKLKHTKKRQIYTDIEMNRLGK

>K47Q/R354A VSV-G envelope protein, amino acid sequence (SEQ ID NO: 17):

KFTIVFPHNQKGNWKNVPSNYHYCPSSSDLNWHNDLIGTAIQVKMPQSHKAIQADGWMCHASKW

VTTCDFRWYGPKYITQSIRSFTPSVEQCKESIEQTKQGTWLNPGFPPQSCGYATVTDAEAVIVQ

VTPHHVLVDEYTGEWVDSQFINGKCSNYICPTVHNSTTWHSDYKVKGLCDSNLISMDITFFSED

GELSSLGKEGTGFRSNYFAYETGGKACKMQYCKHWGVRLPSGVWFEMADKDLFAAARFPECPEG

SSISAPSQTSVDVSLIQDVERILDYSLCQETWSKIRAGLPISPVDLSYLAPKNPGTGPAFTIIN

GTLKYFETRYIRVDIAAPILSRMVGMISGTTTEAELWDDWAPYEDVEIGPNGVLRTSSGYKFPL

YMIGHGMLDSDLHLSSKAQVFEHPHIQDAASQLPDDESLFFGDTGLSKNPIELVEGWFSSWKSS

IASFFFIIGLIIGLFLVLRVGIHLCIKLKHTKKRQIYTDIEMNRLGK

>Exemplary wild-type measles envelope protein (with leader sequence), DNA sequence (SEQ ID NO: 18):

ATGGGCAGCCGGATCGTGATCAACCGGGAGCACCTGATGATCGACCGGCCCTACGTGCTGCTGG

CCGTGCTGTTCGTGATGTTCCTGAGCCTGATCGGCTTGCTAGCCATTGCTGGAATCCGGCTGCA

CAGAGCCGCCATCTACACCGCCGAGATCCACAAGAGCCTGAGCACCAACCTGGACGTGACCAAC

AGCATCGAGCATCAGGTCAAGGACGTGCTGACCCCCCTGTTTAAGATCATCGGCGACGAAGTGG

GCCTGCGGACCCCCCAGAGATTCACCGACCTGGTCAAGTTCATCAGCGACAAGATCAAGTTCCT

GAACCCCGACCGGGAGTACGACTTCCGGGACCTGACCTGGTGCATCAACCCCCCCGAGCGGATC

AAGCTGGACTACGACCAGTACTGCGCCGATGTGGCCGCCGAGGAACTGATGAATGCATTGGTGA

-continued

ACTCAACTCTACTGGAGACCAGAACAACCAATCAGTTCCTAGCTGTCTCAAAGGGAAACTGCTC

AGGGCCCACTACAATCAGAGGTCAATTCTCAAACATGTCGCTGTCCCTGTTAGACTTGTATTTA

GGTCGAGGTTACAATGTGTCATCTATAGTCACTATGACATCCCAGGGAATGTATGGGGGAACTT

ACCTAGTGGAAAAGCCTAATCTGAGCAGCAAAAGGTCAGAGTTGTCACAACTGAGCATGTACCG

AGTGTTTGAAGTAGGTGTTATCAGAAATCCGGGTTTGGGGGCTCCGGTGTTCCATATGACAAAC

TATCTTGAGCAACCAGTCAGTAATGATCTCAGCAACTGTATGGTGGCTTTGGGGGAGCTCAAAC

TCGCAGCCCTTTGTCACGGGGAAGATTCTATCACAATTCCCTATCAGGGATCAGGGAAAGGTGT

CAGCTTCCAGCTCGTCAAGCTAGGTGTCTGGAAATCCCCAACCGACATGCAATCCTGGGTCCCC

TTATCAACGGATGATCCAGTGATAGACAGGCTTTACCTCTCATCTCACAGAGGTGTTATCGCTG

ACAACCAAGCAAAATGGGCTGTCCCGACAACACGAACAGATGACAAGTTGCGAATGGAGACATG

CTTCCAACAGGCGTGTAAGGGTAAAATCCAAGCACTCTGCGAGAATCCCGAGTGGGCACCATTG

AAGGATAACAGGATTCCTTCATACGGGGTCTTGTCTGTTGATCTGAGTCTGACAGTTGAGCTTA

AAATCAAAATTGCTTCGGGATTCGGGCCATTGATCACACACGGTTCAGGGATGGACCTATACAA

ATCCAACCACAACAATGTGTATTGGCTGACTATCCCGCCAATGAAGAACCTAGCCTTAGGTGTA

ATCAACACATTGGAGTGGATACCGAGATTCAAGGTTAGTCCCtatCTCTTCAcaGTCCCAATTA

AGGAAGCAGGCGGAGACTGCCATGCCCCAACATACCTACCTGCGGAGGTGGATGGTGATGTCAA

ACTCAGTTCCAATCTGGTGATTCTACCTGGTCAAGATCTCCAATATGTTTTGGCAACCTACGAT

ACTTCCcgGGTTGAACATGCTGTGGTTTATTACGTTTACAGCCCAAGCCGCTCATTTTCTTACT

TTTATCCTTTTAGGTTGCCTATAAAGGGGGTCCCCATCGAATTACAAGTGGAATGCTTCACATG

GGACCAAAAACTCTGGTGCCGTCACTTCTGTGTGCTTGCGGACTCAGAATCTGGTGGACATATC

ACTCACTCTGGGATGGTGGGCATGGGAGTCAGCTGCACAGTCACCCGGGAAGATGGAACCAATG

ACTACAAAGACGATGACGACAAGTGA

>Exemplary wild-type measles envelope protein,
amino acid sequence (SEQ ID NO: 19):
MGSRIVINREHLMIDRPYVLLAVLFVMFLSLIGLLAIAGIRLHRAAIYTAEIHKSLSTNLDVTN

SIEHQVKDVLTPLFKIIGDEVGLRTPQRFTDLVKFISDKIKFLNPDREYDFRDLTWCINPPERI

KLDYDQYCADVAAEELMNALVNSTLLETRTTNQFLAVSKGNCSGPTTIRGQFSNMSLSLLDLYL

GRGYNVSSIVTMTSQGMYGGTYLVEKPNLSSKRSELSQLSMYRVFEVGVIRNPGLGAPVFHMTN

YLEQPVSNDLSNCMVALGELKLAALCHGEDSITIPYQGSGKGVSFQLVKLGVWKSPTDMQSWVP

LSTDDPVIDRLYLSSHRGVIADNQAKWAVPTTRTDDKLRMETCFQQACKGKIQALCENPEWAPL

KDNRIPSYGVLSVDLSLTVELKIKIASGFGPLITHGSGMDLYKSNHNNVYWLTIPPMKNLALGV

INTLEWIPRFKVSPYLFTVPIKEAGGDCHAPTYLPAEVDGDVKLSSNLVILPGQDLQYVLATYD

TSRVEHAVVYYVYSPSRSFSYFYPFRLPIKGVPIELQVECFTWDQKLWCRHFCVLADSESGGHI

THSGMVGMGVSCTVTREDGTNDYKDDDDK

>Exemplary mutant measles envelope protein,
DNA sequence (SEQ ID NO: 20):
ATGGGCAGCCGGATCGTGATCAACCGGGAGCACCTGATGATCGACCGGCCCTACGTGCTGCTGG

CCGTGCTGTTCGTGATGTTCCTGAGCCTGATCGGCTTGCTAGCCATTGCTGGAATCCGGCTGCA

CAGAGCCGCCATCTACACCGCCGAGATCCACAAGAGCCTGAGCACCAACCTGGACGTGACCAAC

AGCATCGAGCATCAGGTCAAGGACGTGCTGACCCCCCTGTTTAAGATCATCGGCGACGAAGTGG

GCCTGCGGACCCCCCAGAGATTCACCGACCTGGTCAAGTTCATCAGCGACAAGATCAAGTTCCT

GAACCCCGACCGGGAGTACGACTTCCGGGACCTGACCTGGTGCATCAACCCCCCCGAGCGGATC

-continued

AAGCTGGACTACGACCAGTACTGCGCCGATGTGGCCGCCGAGGAACTGATGAATGCATTGGTGA

ACTCAACTCTACTGGAGACCAGAACAACCAATCAGTTCCTAGCTGTCTCAAAGGGAAACTGCTC

AGGGCCCACTACAATCAGAGGTCAATTCTCAAACATGTCGCTGTCCCTGTTAGACTTGTATTTA

GGTCGAGGTTACAATGTGTCATCTATAGTCACTATGACATCCCAGGGAATGTATGGGGGAACTT

ACCTAGTGGAAAAGCCTAATCTGAGCAGCAAAAGGTCAGAGTTGTCACAACTGAGCATGTACCG

AGTGTTTGAAGTAGGTGTTATCAGAAATCCGGGTTTGGGGGCTCCGGTGTTCCATATGACAAAC

TATCTTGAGCAACCAGTCAGTAATGATCTCAGCAACTGTATGGTGGCTTTGGGGGAGCTCAAAC

TCGCAGCCCTTTGTCACGGGGAAGATTCTATCACAATTCCCTATCAGGGATCAGGGAAAGGTGT

CAGCTTCCAGCTCGTCAAGCTAGGTGTCTGGAAATCCCCAACCGACATGCAATCCTGGGTCCCC

TTATCAACGGATGATCCAGTGATAGACAGGCTTTACCTCTCATCTCACAGAGGTGTTATCGCTG

ACAACCAAGCAAAATGGGCTGTCCCGACAACACGAACAGATGACAAGTTGCGAATGGAGACATG

CTTCCAACAGGCGTGTAAGGGTAAAATCCAAGCACTCTGCGAGAATCCCGAGTGGGCACCATTG

AAGGATAACAGGATTCCTTCATACGGGGTCTTGTCTGTTGATCTGAGTCTGACAGTTGAGCTTA

AAATCAAAATTGCTTCGGGATTCGGGCCATTGATCACACACGGTTCAGGGATGGACCTATACAA

ATCCAACCACAACAATGTGTATTGGCTGACTATCCCGCCAATGAAGAACCTAGCCTTAGGTGTA

ATCAACACATTGGAGTGGATACCGAGATTCAAGGTTAGTCCCGCGCTCTTCAATGTCCCAATTA

AGGAAGCAGGCGGAGACTGCCATGCCCCAACATACCTACCTGCGGAGGTGGATGGTGATGTCAA

ACTCAGTTCCAATCTGGTGATTCTACCTGGTCAAGATCTCCAATATGTTTTGGCAACCTACGAT

ACTTCCGCGGTTGAACATGCTGTGGTTTATTACGTTTACAGCCCAAGCCGCTCATTTTCTTACT

TTTATCCTTTTAGGTTGCCTATAAAGGGGGTCCCCATCGAATTACAAGTGGAATGCTTCACATG

GGACCAAAAACTCTGGTGCCGTCACTTCTGTGTGCTTGCGGACTCAGAATCTGGTGGACATATC

ACTCACTCTGGGATGGTGGGCATGGGAGTCAGCTGCACAGTCACCCGGGAAGATGGAACCAATG

ACTACAAAGACGATGACGACAAGTGA

>Exemplary mutant measles envelope protein,
amino acid sequence (SEQ ID NO: 21):

MGSRIVINREHLMIDRPYVLLAVLFVMFLSLIGLLAIAGIRLHRAAIYTAEIHKSLSTNLDVTN

HSIEQVKDVLTPLFKIIGDEVGLRTPQRFTDLVKFISDKIKFLNPDREYDFRDLTWCINPPERI

KLDYDQYCADVAAEELMNALVNSTLLETRTTNQFLAVSKGNCSGPTTIRGQFSNMSLSLLDLYL

GRGYNVSSIVTMTSQGMYGGTYLVEKPNLSSKRSELSQLSMYRVFEVGVIRNPGLGAPVFHMTN

YLEQPVSNDLSNCMVALGELKLAALCHGEDSITIPYQGSGKGVSFQLVKLGVWKSPTDMQSWVP

LSTDDPVIDRLYLSSHRGVIADNQAKWAVPTTRTDDKLRMETCFQQACKGKIQALCENPEWAPL

KDNRIPSYGVLSVDLSLTVELKIKIASGFGPLITHGSGMDLYKSNHNNVYWLTIPPMKNLALGV

INTLEWIPRFKVSPALFNVPIKEAGGDCHAPTYLPAEVDGDVKLSSNLVILPGQDLQYVLATYD

TSAVEHAVVYYVYSPSRSFSYFYPFRLPIKGVPIELQVECFTWDQKLWCRHFCVLADSESGGHI

THSGMVGMGVSCTVTREDGTNDYKDDDDK

>Exemplary mutant Nipah envelope protein,
DNA sequence (SEQ ID NO: 22):

ATGAAGAAGATCAACGAGGGCCTGCTGGACAGCAAGATCCTGAGCGCCTTCAACACCGTGATTG

CCCTGCTGGGCTCTATCGTGATCATCGTGATGAACATCATGATCATCCAGAACTACACCCGGTC

CACCGACAACCAGGCCGTGATTAAGGATGCTCTGCAGGGAATCCAGCAGCAGATCAAAGGCCTG

GCCGACAAGATCGGCACAGAGATCGGCCCTAAGGTGTCCCTGATCGACACCAGCAGCACCATCA

CAATCCCCGCCAATATCGGACTGCTGGGAAGCAAGATCAGCCAGAGCACCGCCAGCATCAACGA

GAACGTGAACGAGAAGTGCAAGTTCACCCTGCCTCCACTGAAGATCCACGAGTGCAACATCAGC

-continued

TGCCCCAATCCTCTGCCATTCAGAGAGTACAGACCCCAGACAGAGGGCGTGTCCAATCTCGTGG

GCCTGCCTAACAACATCTGCCTGCAGAAAACCAGCAACCAGATCCTGAAGCCTAAGCTGATCTC

CTACACACTGCCCGTCGTGGGCCAGAGCGGCACCTGTATTACAGATCCTCTGCTGGCCATGGAC

GAGGGCTACTTTGCCTACAGCCACCTGGAAAGAATCGGCAGCTGTAGCCGGGGAGTGTCCAAGC

AGAGAATCATCGGCGTGGGCGAAGTGCTGGATAGAGGCGACGAAGTGCCCAGCCTGTTCATGAC

CAATGTGTGGACCCCTCCTAATCCTAACACCGTGTACCACTGCAGCGCCGTGTACAACAACGAG

TTCTACTACGTGCTGTGCGCCGTGTCCACAGTGGGCGACCCTATCCTGAACAGCACCTATTGGA

GCGGCAGCCTGATGATGACCAGACTGGCCGTGAAGCCCAAGAGCAATGGCGGCGGATACAACCA

GCATCAGCTGGCCCTGCGGTCCATCGAGAAGGGCAGATACGACAAAGTGATGCCTTACGGCCCC

AGCGGCATCAAGCAAGGCGATACCCTGTACTTTCCCGCCGTGGGATTTCTCGTGCGGACCGAGT

TCAAGTACAACGACAGCAACTGCCCCATCACCAAGTGCCAGTACAGCAAGCCCGAGAACTGCAG

ACTGAGCATGGGCATCAGACCCAACAGCCACTACATCCTGAGAAGCGGCCTGCTGAAGTACAAC

CTGAGCGACGGCGAGAACCCCAAGGTGGTGTTCATCGAGATCAGCGACCAGCGGCTGTCTATCG

GCAGCCCCTCCAAGATCTACGACTCTCTGGGCCAGCCAGTGTTCTACCAGGCCAGCTTTAGCTG

GGACACCATGATCAAGTTCGGCGACGTGCTGACCGTGAATCCCCTGGTGGTCAACTGGCGGAAC

AATACCGTGATCAGCCGGCCTGGCCAGTCTCAGTGCCCCAGATTCAATACCTGTCCTGCCATTT

GCGCCGAAGGCGTGTACAATGACGCCTTCCTGATCGATCGGATCAACTGGATCTCTGCCGGCGT

GTTCCTGGACTCTAATGCCACAGCCGCCAATCCTGTGTTCACCGTGTTCAAGGACAATGAGATC

CTGTATCGGGCCCAGCTGGCCTCCGAGGACACAAATGCCCAGAAAACAATCACCAACTGCTTTC

TGCTCAAGAACAAGATCTGGTGCATCAGCCTGGTGGAAATCTACGACACCGGCGACAACGTGAT

CAGGCCCAAGCTGTTCGCCGTGAAGATCCCTGAGCAGTGTACAGGCGGCGGAGGATCTGGCGGA

GGTGGAAGCGGAGGCGGTGGATCTGCTAGCGATTACAAGGATGACGACGATAAGTGA

>Exemplary mutant Nipah envelope protein,
amino acid sequence (SEQ ID NO: 23):
MKKINEGLLDSKILSAFNTVIALLGSIVIIVMNIMIIQNYTRSTDNQAVIKDALQGIQQQIKGL

ADKIGTEIGPKVSLIDTSSTITIPANIGLLGSKISQSTASINENVNEKCKFTLPPLKIHECNIS

CPNPLPFREYRPQTEGVSNLVGLPNNICLQKTSNQILKPKLISYTLPVVGQSGTCITDPLLAMD

EGYFAYSHLERIGSCSRGVSKQRIIGVGEVLDRGDEVPSLFMTNVWTPPNPNTVYHCSAVYNNE

FYYVLCAVSTVGDPILNSTYWSGSLMMTRLAVKPKSNGGGYNQHQLALRSIEKGRYDKVMPYGP

SGIKQGDTLYFPAVGFLVRTEFKYNDSNCPITKCQYSKPENCRLSMGIRPNSHYILRSGLLKYN

LSDGENPKVVFIEISDQRLSIGSPSKIYDSLGQPVFYQASFSWDTMIKFGDVLTVNPLVVNWRN

NTVISRPGQSQCPRFNTCPAICAEGVYNDAFLIDRINWISAGVFLDSNATAANPVFTVFKDNEI

LYRAQLASEDTNAQKTITNCFLLKNKIWCISLVEIYDTGDNVIRPKLFAVKIPEQCTGGGGSGG

GGSGGGGSASDYKDDDDK

>IG4 TCR (Variant that binds to NYESO-1 antigen with
32 tiM binding affinity), amino acid sequence
(SEQ ID NO: 24):
MSIGLLCCAALSLLWAGPVNAGVTQTPKFQVLKTGQSMTLQCAQDMNHEYMSWYRQDPGMGLRL

IHYSVGAGITDQGEVPNGYNVSRSTTEDFPLRLLSAAPSQTSVYFCASSYVGNTGELFFGEGSR

LTVLEDLKNVFPPEVAVFEPSEAEISHTQKATLVCLATGFYPDHVELSWWVNGKEVHSGVSTDP

QPLKEQPALNDSRYCLSSRLRVSATFWQNPRNHFRCQVQFYGLSENDEWTQDRAKPVTQIVSAE

AWGRADCGFTSESYQQGVLSATILYEILLGKATLYAVLVSALVLMAMVKRKDSRGGSATNFSLL

KQAGDVEENPGPMETLLGLLILWLQLQWVSSKQEVTQIPAALSVPEGENLVLNCSFTDSAIYNL

-continued

QWFRQDPGKGLTSLLLIQSSQREQTSGRLNASLDKSSGSSTLYIAASQPGDSATYLCAVRPTSG

GSYIPTFGRGTSLIVHPYIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>IG4 TCR (Variant that binds to NYESO-1 antigen with 84 nM binding affinity), amino acid sequence (SEQ ID NO: 25):

MSIGLLCCAALSLLWAGPVNAGVTQTPKFQVLKTGQSMTLQCAQDMNHEYMSWYRQDPGMGLRL

IHYSVGAQTTDQGEVPNGYNVSRSTIEDFPLRLLSAAPSQTSVYFCASSYLGNTGELFFGEGSR

LTVLEDLKNVFPPEVAVFEPSEAEISHTQKATLVCLATGFYPDHVELSWWVNGKEVHSGVSTDP

QPLKEQPALNDSRYCLSSRLRVSATFWQNPRNHFRCQVQFYGLSENDEWTQDRAKPVTQIVSAE

AWGRADCGFTSESYQQGVLSATILYEILLGKATLYAVLVSALVLMAMVKRKDSRGGSATNFSLL

KQAGDVEENPGPMETLLGLLILWLQLQWVSSKQEVTQIPAALSVPEGENLVLNCSFTDSAIYNL

QWFRQDPGKGLTSLLLIQSSQREQTSGRLNASLDKSSGSSTLYIAASQPGDSATYLCAVRPMIG

GTYIPTFGRGTSLIVHPYIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>IG4 TCR (Variant that binds to NYESO-1 antigen with 5 nM binding affinity), amino acid sequence (SEQ ID NO: 26):

MSIGLLCCAALSLLWAGPVNAGVTQTPKFQVLKTGQSMTLQCAQDMNHEYMSWYRQDPGMGLRL

IHYSVGAGTTDRGEVPNGYNVSRSTIEDFPLRLLSAAPSQTSVYFCASSYVGDTGELFFGEGSR

LTVLEDLKNVFPPEVAVFEPSEAEISHTQKATLVCLATGFYPDHVELSWWVNGKEVHSGVSTDP

QPLKEQPALNDSRYCLSSRLRVSATFWQNPRNHFRCQVQFYGLSENDEWTQDRAKPVTQIVSAE

AWGRADCGFTSESYQQGVLSATILYEILLGKATLYAVLVSALVLMAMVKRKDSRGGSATNFSLL

KQAGDVEENPGPMETLLGLLILWLQLQWVSSKQEVTQIPAALSVPEGENLVLNCSFTDSAIYNL

QWFRQDPGKGLTSLLLIQSSQREQTSGRLNASLDKSSGSSTLYIAASQPGDSATYLCAVRPLLD

GTYIPTFGRGTSLIVHPYIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>IG4 TCR (Variant that binds to NYESO-1 antigen with 26 pM binding affinity), amino acid sequence (SEQ ID NO: 27):

MSIGLLCCAALSLLWAGPVNAGVTQTPKFQVLKTGQSMTLQCAQDMNHEYMSWYRQDPGMGLRL

IHYSVAIQTTDQGEVPNGYNVSRSTIEDFPLRLLSAAPSQTSVYFCASSYLGNTGELFFGEGSR

LTVLEDLKNVFPPEVAVFEPSEAEISHTQKATLVCLATGFYPDHVELSWWVNGKEVHSGVSTDP

QPLKEQPALNDSRYCLSSRLRVSATFWQNPRNHFRCQVQFYGLSENDEWTQDRAKPVTQIVSAE

AWGRADCGFTSESYQQGVLSATILYEILLGKATLYAVLVSALVLMAMVKRKDSRGGSATNFSLL

KQAGDVEENPGPMETLLGLLILWLQLQWVSSKQEVTQIPAALSVPEGENLVLNCSFTDSAIYNL

QWFRQDPGKGLTSLLLITPWQREQTSGRLNASLDKSSGSSTLYIAASQPGDSATYLCAVRPLLD

GTYIPTFGRGTSLIVHPYIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

-continued

>868 TCR (Beta Chain-P2A-Alpha Chain), amino acid sequence (SEQ ID NO: 31):
MSIGLLCCAALSLLWAGPVNADAGVTQSPTHLIKTRGQQVTLRCSPKQGHDTVSWYQQALGQGP

QFIFQYYEEEERQRGNFPDRFSGHQFPNYSSELNVNALLLGDSALYLCASSDTVSYEQYFGPGT

RLTVTEDLKNVFPPEVAVFEPSEAEISHTQKATLVCLATGFYPDHVELSWWVNGKEVHSGVSTD

PQPLKEQPALNDSRYCLSSRLRVSATFWQDPRNHFRCQVQFYGLSENDEWTQDRAKPVTQIVSA

EAWGRADCGFTSESYQQGVLSATILYEILLGKATLYAVLVSALVLMAMVKRKDSRGGSATNFSL

LKQAGDVEENPGPMETLLGLLILWLQLQWVSSKEVEQNSGPLSVPEGAIASLNCTYSDRGSQSF

FWYRQYSGKSPELIMFIYSNGDKEDGRFTAQLNKASQYISLLIRDSKLSDSATYLCAVRTNSGY

ALNFGKGTSLLVTPHIQKPDPAVYQLRDSKSSDKSVCLFTDFDSQTNVSQSKDSDVYITDKTVL

DMRSMDFKSNSAVAWSNKSDFACANAFNNSIIPEDTFFPSPESSCDVKLVEKSFETDTNLNFQN

LSVIGFRILLLKVAGFNLLMTLRLWSS

>CMV C7 TCR, amino acid sequence (SEQ ID NO: 33):
MGTRLLFWVAFCLLGADHTGAGVSQSPSNKVTEKGKDVELRCDPISGHTALYWYRQRLGQGLEF

LIYFQGNSAPDKSGLPSDRFSAERTGESVSTLTIQRTQQEDSAVYLCASSQTQLWETQYFGPGT

RLLVLEDLKNVFPPEVAVFEPSEAEISHTQKATLVCLATGFYPDHVELSWWVNGKEVHSGVSTD

PQPLKEQPALNDSRYCLSSRLRVSATFWQNPRNHFRCQVQFYGLSENDEWTQDRAKPVTQIVSA

EAWGRADCGFTSESYQQGVLSATILYEILLGKATLYAVLVSALVLMAMVKRKDSRGGSATNFSL

LKQAGDVEENPGPMEKNPLAAPLLILWFHLDCVSSILNVEQSPQSLHVQEGDSTNFTCSFPSSN

FYALHWYRWETAKSPEALFVMTLNGDEKKKGRISATLNTKEGYSYLYIKGSQPEDSATYLCAFI

TGNQFYFGTGTSLTVIPNIQNPDPAVYQLRDSKSSDKSVCLFTDFDSQTNVSQSKDSDVYITDK

TVLDMRSMDFKSNSAVAWSNKSDFACANAFNNSIIPEDTFFPSPESSCDVKLVEKSFETDTNLN

FQNLSVIGFRILLLKVAGFNLLMTLRLWSSAAA

>SL9 pMHC (5L9 peptide portion bolded), amino acid sequence (SEQ ID NO: 35):
MSRSVALAVLALLSLSGLEASLYNTVATLGGGASGGGGSGGGGSIQRTPKIQVYSRHPAENGKS

NFLNCYVSGFHPSDIEVDLLKNGERIEKVEHSDLSFSKDWSFYLLYYTEFTPTEKDEYACRVNH

VTLSQPKIVKWDRDMGGGGSGGGGSGGGGSGGGGSHSMRYFFTSVSRPGRGEPRFIAVGYVDDT

QFVRFDSDAASQRMEPRAPWIEQEGPEYWDGETRKVKAHSQTHRVDLGTLRGAYNQSEAGSHTV

QRMYGCDVGSDWRFLRGYHQYAYDGKDYIALKEDLRSWTAADMAAQTTKHKWEAAHVAEQLRAY

LEGTCVEWLRRYLENGKETLQRTDAPKTHMTHHAVSDHEATLRCWALSFYPAEITLTWQRDGED

QTQDTELVETRPAGDGTFQKWAAVVVPSGQEQRYTCHVQHEGLPKPLTLRWEPSSQPTIPIVGI

IAGLVLFGAVITGAVVAAVMWRRKSS

>CMV pMHC (CMV NLV peptide portion bolded), amino acid sequence (SEQ ID NO: 37):
MSRSVALAVLALLSLSGLEANLVPMVATVGASGGSGGGSGGGGSIQRTPKIQVYSRHPAENGKS

NFLNCYVSGFHPSDIEVDLLKNGERIEKVEHSDLSFSKDWSFYLLYYTEFTPTEKDEYACRVNH

VTLSQPKIVKWDRDMGGGGSGGGGSGGGGSGGGGSHSMRYFFTSVSRPGRGEPRFIAVGYVDDT

QFVRFDSDAASQRMEPRAPWIEQEGPEYWDGETRKVKAHSQTHRVDLGTLRGAYNQSEAGSHTV

QRMYGCDVGSDWRFLRGYHQYAYDGKDYIALKEDLRSWTAADMAAQTTKHKWEAAHVAEQLRAY

LEGTCVEWLRRYLENGKETLQRTDAPKTHMTHHAVSDHEATLRCWALSFYPAEITLTWQRDGED

QTQDTELVETRPAGDGTFQKWAAVVVPSGQEQRYTCHVQHEGLPKPLTLRWEPSSQPTIPIVGI

IAGLVLFGAVITGAVVAAVMWRRKSS

-continued

>disulfide trap MHC comprising Y84C mutation(bolded) and position 2 of the linker being a C (bolded); shown with the HGH Signal Peptide (underlined) and the GL9 peptide (italicized), amino acid sequence (SEQ ID NO: 39):

MATGSRTSLLLAFGLLCLPWLQEGSAGILGFVFTLGCSGGSGGGSGGGGSIQRTPKIQVYSRHP

AENGKSNFLNCYVSGFHPSDIEVDLLKNGERIEKVEHSDLSFSKDWSFYLLYYTEFTPTEKDEY

ACRVNHVTLSQPKIVKWDRDMGGGGSGGSGSGGSGSGGGSGGSHSMRYFFTSVSRPGRGEPRFI

AVGYVDDTQFVRFDSDAASQRMEPRAPWIEQEGPEYWDGETRKVKAHSQTHRVDLGTLRGCYNQ

SEAGSHTVQRMYGCDVGSDWRFLRGYHQYAYDGKDYIALKEDLRSWTAADMAAQTTKHKWEAAH

VAEQLRAYLEGTCVEWLRRYLENGKETLQRTDAPKTHMTHHAVSDHEATLRCWALSFYPAEITL

TWQRDGEDQTQDTELVETRPAGDGTFQKWAAVVVPSGQEQRYTCHVQHEGLPKPLTLRWEPSSQ

PTIPIVGIIAGLVLFGAVITGAVVAAVMWRRKSS

>GL9 pMHC (GL9 peptide portion bolded), amino acid sequence (SEQ ID NO: 41):

MSRSVALAVLALLSLSGLEAGILGFVFTLGGGASGGGGSGGGGSIQRTPKIQVYSRHPAENGKS

NFLNCYVSGFHPSDIEVDLLKNGERIEKVEHSDLSFSKDWSFYLLYYTEFTPTEKDEYACRVNH

VTLSQPKIVKWDRDMGGGGSGGGGSGGGGSGGGGSHSMRYFFTSVSRPGRGEPRFIAVGYVDDT

QFVRFDSDAASQRMEPRAPWIEQEGPEYWDGETRKVKAHSQTHRVDLGTLRGAYNQSEAGSHTV

QRMYGCDVGSDWRFLRGYHQYAYDGKDYIALKEDLRSWTAADMAAQTTKHKWEAAHVAEQLRAY

LEGTCVEWLRRYLENGKETLQRTDAPKTHMTHHAVSDHEATLRCWALSFYPAEITLTWQRDGED

QTQDTELVETRPAGDGTFQKWAAVVVPSGQEQRYTCHVQHEGLPKPLTLRWEPSSQPTIPIVGI

IAGLVLFGAVITGAVVAAVMWRRKSS

>CD80, amino acid sequence (SEQ ID NO: 43):

MGHTRRQGTSPSKCPYLNFFQLLVLAGLSHFCSGVIHVTKEVKEVATLSCGHNVSVEELAQTRI

YWQKEKKMVLTMMSGDMNIWPEYKNRTIFDITNNLSIVILALRPSDEGTYECVVLKYEKDAFKR

EHLAEVTLSVKADFPTPSISDFEIPTSNIRRIICSTSGGFPEPHLSWLENGEELNAINTTVSQD

PETELYAVSSKLDFNMTTNHSFMCLIKYGHLRVNQTFNWNTTKQEHFPDNLLPSWAITLISVNG

IFVICCLTYCFAPRCRE

>CD86, amino acid sequence (SEQ ID NO: 45):

MDPQCTMGLSNILFVMAFLLSGAAPLKIQAYFNETADLPCQFANSQNQSLSELVVFWQDQENLV

LNEVYLGKEKFDSVHSKYMGRTSFDSDSWTLRLHNLQIKDKGLYQCIIHHKKPTGMIRIHQMNS

ELSVLANFSQPEIVPISNITENVYINLTCSSIHGYPEPKKMSVLLRTKNSTIEYDGVMQKSQDN

VTELYDVSISLSVSFPDVTSNMTIFCILETDKTRLLSSPFSIELEDPQPPPDHIPWITAVLPTV

IICVMVFCLILWKWKKKKR

>mouse anti-TCR Beta Clone H57-597 Fab antibody (light chain-P2A-heavy chain, PDGFR transmembrane domain), amino acid sequence: (SEQ ID NO: 47):

METDTLLLWVLLLWVPGSTGADYKDDDDKDIQMTQSPSSLPASLGDRVTINCQASQDISNYLNW

YQQKPGKAPKLLIYYTNKLADGVPSRFSGSGSGRDSSFTISSLESEDIGSYYCQQYYNYPWTFG

PGTKLEIKRADAKPTVSIFPPSSEQLGTGSATLVCFVNNFYPKDINVKWKVDGSEKRDGVLQSV

TDQDSKDSTYSLSSTLSLTKADYERHNLYTCEVTHKTSTAAIVKTLNRNECGSGATNFSLLKQA

GDVEENPGPMVPCTLLLLLAAALAPTQTRAEVQLVESGGGLVQPGKSLKLSCEASGFTFSGYGM

HWVRQAPGRGLESVAYITSSSINIKYADAVKGRFTVSRDNAKNLLFLQMNILKSEDTAMYYCAR

-continued

FDWDKNYWGQGTMVTVSSAKTTAPSVYPLAPACDSTTSTTNTVTLGCLVKGYFPEPVTVIWNSG

ALTSGVHTFPSVLHSGLYSLSSSVTVPSSTWPSQTVTCNVAHPASSTTVDLKIEAVGQDTQEVI

VVPHSLPFKVVVISAILALVVLTIISLIILIMLWQKKPR

>mouse anti-CD3 Epsilon Clone 145-2C11 Fab antibody
(light chain-P2A-heavy chain, PDGFR transmembrane domain),
amino acid sequence (SEQ ID NO: 49):
METDTLLLWVLLLWVPGSTGADYKDDDDKYELIQPSSASVTVGETVKITCSGDQLPKNFAYWFQ

QKSDKNILLLIYMDNKRPSGIPERFSGSTSGTTATLTISGAQPEDEAAYYCLSSYGDNNDLVFG

SGTQLTVLRGPKSSPKVTVFPPSPEELRTNKATLVCLVNDFYPGSATVTWKANGATINDGVKTT

KPSKQGQNYMTSSYLSLTADQWKSHNRVSCQVTHEGETVEKSLSPAECLGSGATNFSLLKQAGD

VEENPGPMVPCTLLLLLAAALAPTQTRAEVYLVESGGDLVQPGSSLKVSCAASGFTFSDFWMYW

VRQAPGKGLEWVGRIKNIPNNYATEYADSVRGRFTISRDDSRNSIYLQMNRLRVDDTAIYYCTR

AGRFDHFDYWGQGTMVTVSSATTTAPSVYPLAPACDSTTSTTDTVTLGCLVKGYFPEPVTVSWN

SGALTSGVHTFPSVLHSGLYSLSSSVTVPSSTWPKQPITCNVAHPASSTKVDKKIEPRAVGQDT

QEVIVVPHSLPFKVVVISAILALVVLTIISLIILIMLWQKKPR*

>Cocal Virus Glycoprotein, amino acid sequence:
(SEQ ID NO: 51):
MNFLLLTFIVLPLCSHAKFSIVFPQSQKGNWKNVPSSYHYCPSSSDQNWHNDLLGITMKVKMPK

THKAIQADGWMCHAAKWITTCDFRWYGPKYITHSIHSIQPTSEQCKESIKQTKQGTWMSPGFPP

QNCGYATVTDSVAVVVQATPHHVLVDEYTGEWIDSQFPNGKCETEECETVHNSTVWYSDYKVTG

LCDATLVDTEITFFSEDGKKESIGKPNTGYRSNYFAYEKGDKVCKMNYCKHAGVRLPSGVWFEF

VDQDVYAAAKLPECPVGATISAPTQTSVDVSLILDVERILDYSLCQETWSKIRSKQPVSPVDLS

YLAPKNPGTGPAFTIINGTLKYFETRYIRIDIDNPIISKMVGKISGSQTERELWTEWFPYEGVE

IGPNGILKTPTGYKFPLFMIGHGMLDSDLHKTSQAEVFEHPHLAEAPKQLPEEETLFFGDTGIS

KNPVELIEGWFSSWKSTVVTFFFAIGVFILLYVVARIVIAVRYRYQGSNNKRIYNDIEMSRFRK*

>Cocal Virus Glycoprotein, DNA sequence: (SEQ ID NO: 52):
ATGAACTTTCTGCTGCTCACGTTTATCGTACTCCCGTTGTGCTCTCATGCGAAATTTTCAATAG

TCTTTCCTCAGTCCCAGAAAGGGAATTGGAAAAATGTTCCCTCCAGTTACCACTATTGTCCCTC

CTCCTCTGACCAAAACTGGCACAATGACTTGCTCGGGATTACAATGAAAGTAAAGATGCCGAAA

ACCCATAAAGCCATACAGGCGGATGGGTGGATGTGTCACGCTGCGAAGTGGATCACTACATGCG

ATTTCCGGTGGTATGGCCCTAAGTACATTACACACTCTATCCATAGCATACAGCCGACATCAGA

GCAATGCAAAGAGAGTATTAAACAGACCAAACAAGGGACATGGATGAGCCCTGGCTTTCCACCT

CAGAATTGTGGGTACGCGACCGTCACGGATAGTGTCGCTGTTGTGGTGCAGGCCACGCCACATC

ACGTACTCGTAGATGAATATACTGGTGAATGGATCGACTCCCAATTCCCGAATGGGAAATGTGA

GACGGAAGAGTGCGAAACAGTGCATAACTCAACCGTTTGGTATTCCGATTACAAGGTTACTGGT

CTTTGCGACGCCACCCTCGTGGATACCGAGATCACGTTTTTTAGTGAGGATGGCAAGAAAGAGT

CAATAGGCAAACCTAATACTGGCTACCGGAGTAACTATTTCGCTTACGAGAAGGGTGACAAGGT

ATGTAAAATGAACTATTGCAAGCATGCGGGAGTGCGACTCCCCAGTGGGGTATGGTTCGAATTT

GTTGACCAAGACGTATACGCCGCTGCGAAGTTGCCAGAATGCCCCGTAGGCGCGACCATTTCAG

CACCTACCCAAACGTCCGTTGACGTCTCCTTGATACTGGATGTAGAGCGAATCCTGGACTACAG

TCTCTGCCAGGAAACGTGGTCAAAAATAAGAAGTAAGCAGCCAGTTTCACCCGTGGATCTGTCT

TATCTGGCGCCAAAAAACCCGGGCACGGGCCCTGCTTTTACCATAATTAACGGAACGCTTAAAT

ACTTCGAAACCCGCTACATTAGAATCGATATAGACAATCCTATTATCAGCAAGATGGTAGGGAA

-continued

GATATCTGGGTCTCAAACGGAGCGAGAATTGTGGACGGAGTGGTTCCCTTATGAGGGAGTGGAA

ATTGGGCCCAACGGGATCCTCAAGACCCCAACGGGTTACAAGTTCCCTCTGTTTATGATCGGCC

ATGGCATGTTGGACAGTGACTTGCACAAAACATCTCAGGCAGAGGTTTTCGAACATCCACATTT

GGCGGAGGCGCCCAAGCAACTTCCAGAAGAAGAAACTCTCTTCTTTGGAGATACAGGCATTTCA

AAAAATCCTGTAGAACTGATAGAAGGGTGGTTCTCTTCCTGGAAATCAACGGTTGTCACGTTTT

TCTTTGCAATAGGCGTATTTATACTCCTGTACGTCGTAGCCCGCATTGTGATCGCAGTACGATA

CAGATACCAGGGCAGTAACAATAAACGCATATATAATGACATCGAAATGTCAAGGTTCCGAAAG tga

>Cocal-dead (mutations to ablate native tropism bolded in protein sequence; these are K64Q and R371A, counting from the start codon), amino acid sequence: (SEQ ID NO: 53):

MNFLLLTFIVLPLCSHAKFSIVFPQSQKGNWKNVPSSYHYCPSSSDQNWHNDLLGITMKVKMPQ

THKAIQADGWMCHAAKWITTCDFRWYGPKYITHSIHSIQPTSEQCKESIKQTKQGTWMSPGFPP

QNCGYATVTDSVAVVVQATPHHVLVDEYTGEWIDSQFPNGKCETEECETVHNSTVWYSDYKVTG

LCDATLVDTEITFFSEDGKKESIGKPNTGYRSNYFAYEKGDKVCKMNYCKHAGVRLPSGVWFEF

VDQDVYAAAKLPECPVGATISAPTQTSVDVSLILDVERILDYSLCQETWSKIRSKQPVSPVDLS

YLAPKNPGTGPAFTIINGTLKYFETRYIRIDIDNPIISKMVGKISGSQTEAELWTEWFPYEGVE

IGPNGILKTPTGYKFPLFMIGHGMLDSDLHKTSQAEVFEHPHLAEAPKQLPEEETLFFGDTGIS

KNPVELIEGWFSSWKSTVVTFFFAIGVFILLYVVARIVIAVRYRYQGSNNKRIYNDIEMSRFRK

>Cocal-dead (mutations to ablate native tropism), DNA sequence: (SEQ ID NO: 54):

ATGAACTTTCTGCTGCTCACGTTTATCGTACTCCCGTTGTGCTCTCATGCGAAATTTTCAATAG

TCTTTCCTCAGTCCCAGAAAGGGAATTGGAAAAATGTTCCCTCCAGTTACCACTATTGTCCCTC

CTCCTCTGACCAAAACTGGCACAATGACTTGCTCGGGATTACAATGAAAGTAAAGATGCCGcag

ACCCATAAAGCCATACAGGCGGATGGGTGGATGTGTCACGCTGCGAAGTGGATCACTACATGCG

ATTTCCGGTGGTATGGCCCTAAGTACATTACACACTCTATCCATAGCATACAGCCGACATCAGA

GCAATGCAAAGAGAGTATTAAACAGACCAAACAAGGGACATGGATGAGCCCTGGCTTTCCACCT

CAGAATTGTGGGTACGCGACCGTCACGGATAGTGTCGCTGTTGTGGTGCAGGCCACGCCACATC

ACGTACTCGTAGATGAATATACTGGTGAATGGATCGACTCCCAATTCCCGAATGGGAAATGTGA

GACGGAAGAGTGCGAAACAGTGCATAACTCAACCGTTTGGTATTCCGATTACAAGGTTACTGGT

CTTTGCGACGCCACCCTCGTGGATACCGAGATCACGTTTTTTAGTGAGGATGGCAAGAAAGAGT

CAATAGGCAAACCTAATACTGGCTACCGGAGTAACTATTTCGCTTACGAGAAGGGTGACAAGGT

ATGTAAAATGAACTATTGCAAGCATGCGGGAGTGCGACTCCCCAGTGGGGTATGGTTCGAATTT

GTTGACCAAGACGTATACGCCGCTGCGAAGTTGCCAGAATGCCCCGTAGGCGCGACCATTTCAG

CACCTACCCAAACGTCCGTTGACGTCTCCTTGATACTGGATGTAGAGCGAATCCTGGACTACAG

TCTCTGCCAGGAAACGTGGTCAAAAATAAGAAGTAAGCAGCCAGTTTCACCCGTGGATCTGTCT

TATCTGGCGCCAAAAAACCCGGGCACGGGCCCTGCTTTTACCATAATTAACGGAACGCTTAAAT

ACTTCGAAACCCGCTACATTAGAATCGATATAGACAATCCTATTATCAGCAAGATGGTAGGGAA

GATATCTGGGTCTCAAACGGAGgccGAATTGTGGACGGAGTGGTTCCCTTATGAGGGAGTGGAA

ATTGGGCCCAACGGGATCCTCAAGACCCCAACGGGTTACAAGTTCCCTCTGTTTATGATCGGCC

ATGGCATGTTGGACAGTGACTTGCACAAAACATCTCAGGCAGAGGTTTTCGAACATCCACATTT

GGCGGAGGCGCCCAAGCAACTTCCAGAAGAAGAAACTCTCTTCTTTGGAGATACAGGCATTTCA

AAAAATCCTGTAGAACTGATAGAAGGGTGGTTCTCTTCCTGGAAATCAACGGTTGTCACGTTTT

-continued

TCTTTGCAATAGGCGTATTTATACTCCTGTACGTCGTAGCCCGCATTGTGATCGCAGTACGATA

CAGATACCAGGGCAGTAACAATAAACGCATATATAATGACATCGAAATGTCAAGGTTCCGAAAG tga

What is claimed is:

1. A method of delivering a nucleic acid to a cell, the method comprising:

(i) providing a retrovirus comprising (a) the nucleic acid and (b) a viral envelope that comprises at least two different proteins:

1) a viral envelope protein comprising at least one mutation that diminishes the native viral tropism of the mutated viral envelope protein compared to the non-mutated viral envelope protein, wherein the viral envelope protein is a vesicular stomatitis virus (VSV)-G envelope protein that comprises an amino acid substitution at position K47 and/or an amino acid substitution at position R354, said positions with reference to SEQ ID NO: 13 or a cocal virus G envelope protein that comprises an amino acid substitution at position K64 and/or an amino acid substitution at position R371, said positions with reference to SEQ ID NO: 51; and 2) a non-viral membrane-bound protein comprising a transmembrane domain and an extracellular targeting domain that is capable of binding to a ligand expressed on the surface of the cell; and (ii) contacting the retrovirus with the cell, thereby delivering the nucleic acid to the cell.

2. The method of claim 1, wherein the nucleic acid encodes a gene of interest, optionally wherein the gene of interest encodes a protein.

3. The method of claim 1, wherein the retrovirus is a lentivirus.

4. The method of claim 1, wherein:

(a) the at least one mutation of the VSV-G envelope protein is an amino acid substitution at position K47 to alanine (A) or glutamine (Q) and/or position R354 to alanine (A) or glutamine (Q) of SEQ ID NO: 13; or (b) the at least one mutation of the cocal virus G protein is an amino acid substitution at position K64 to alanine (A) or glutamine (Q) and/or position R371 to alanine (A) or glutamine (Q) of SEQ ID NO: 51.

5. The method of claim 1, wherein the VSV-G envelope protein comprises the amino acid sequence set forth in SEQ ID NO: 17.

6. The method of claim 1, wherein the cocal virus G protein comprises the amino acid sequence set forth in SEQ ID NO: 53.

7. The method of claim 1, wherein the non-viral membrane-bound protein comprises a class I Major Histocompatibility Complex (MHC) protein or class II MHC protein.

8. The method of 7, wherein the non-viral membrane-bound protein further comprises a peptide displayed by the class I MHC protein or the class II MHC protein.

9. The method of claim 8, wherein the peptide is an NLV peptide, an SL9 peptide, a GL9 peptide, an NY-ESO1 peptide, or an EBV peptide.

10. The method of claim 1, wherein the non-viral membrane-bound protein is CD80.

11. The method of claim 1, wherein the extracellular targeting domain is a protein, a peptide, or an antibody.

12. The method of claim 11, wherein the protein is selected from the group consisting of: interleukin-2 (IL-2), IL-6, IL-12, IL-13, chemokine ligand 9 (CXCL9), CXCL10, and CXCL 11.

13. The method of claim 11, wherein the antibody is a full-length antibody, an antibody fragment, a nanobody, or a single chain antibody (scFv).

14. The method of claim 13, wherein the antibody is an anti-CD19 antibody, an anti-TCR antibody, or an anti-CD3 antibody.

15. The method of claim 1, wherein a linker is positioned between the membrane-bound domain and the extracellular targeting domain.

16. The method of claim 15, wherein the linker is a rigid linker, a flexible linker, or an oligomerized linker.

17. The method of claim 16, wherein the linker comprises a PDGFR stalk, a CD8a stalk, an amino acid sequence comprising GAPGAS (SEQ ID NO:5), an amino acid sequence comprising GGGGS (SEQ ID NO:7), an IgG4 hinge, or an amino acid sequence that forms a tetrameric coiled coil.

18. The method of claim 1, wherein the ligand is expressed on a somatic cell, optionally an antigen-specific cell.

19. The method of claim 1, wherein the ligand is expressed on a T cell or a B cell.

20. The method of claim 1, wherein the ligand is:
(a) a T cell receptor (TCR);
(b) a cytokine receptor;
(c) a cytokine;
(d) a cell surface marker of a T cell or a B cell, or
(e) a cell surface marker selected from the group consisting of CD3, CD19, or CD20.

* * * * *

SEQUENCE LISTING

<160> NUMBER OF SEQ ID NOS: 54

<210> SEQ ID NO 1
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 1

Met Glu Thr Asp Thr Leu Leu Leu Trp Val Leu Leu Leu Trp Val Pro
1               5                   10                  15

Gly Ser Thr Gly
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 2

Met Ser Arg Ser Val Ala Leu Ala Val Leu Ala Leu Leu Ser Leu Ser
1               5                   10                  15

Gly Leu Glu Ala
            20

<210> SEQ ID NO 3
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 3

Ala Val Gly Gln Asp Thr Gln Glu Val Ile Val Val Pro His Ser Leu
1               5                   10                  15

Pro Phe Lys

<210> SEQ ID NO 4
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 4

Ala Ser Ala Lys Pro Thr Thr Thr Pro Ala Pro Arg Pro Pro Thr Pro
1               5                   10                  15

Ala Pro Thr Ile Ala Ser Gln Pro Leu Ser Leu Arg Pro Glu Ala Ala
            20                  25                  30

Arg Pro Ala Ala Gly Gly Ala Val His Thr Arg Gly Leu Asp Phe Ala
        35                  40                  45

Lys

<210> SEQ ID NO 5
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 5

Gly Ala Pro Gly Ala Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 6

Gly Ala Pro Gly Ser Gly Gly Gly Gly Ser Gly Gly Gly Gly Ser Ala
1               5                   10                  15

Ser

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Gly Gly Gly Gly Ser
1               5

<210> SEQ ID NO 8
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 8

Ala Ser Glu Ser Lys Tyr Gly Pro Pro Cys Pro Pro Cys Pro Ala Val
1               5                   10                  15

Gly Gln Asp Thr Gln Glu Val Ile Val Val Pro His Ser Leu Pro Phe
            20                  25                  30

Lys

<210> SEQ ID NO 9
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 9

Ala Ser Gly Gly Gly Gly Ser Gly Glu Leu Ala Ala Ile Lys Gln Glu
1               5                   10                  15

Leu Ala Ala Ile Lys Lys Glu Leu Ala Ala Ile Lys Trp Glu Leu Ala
            20                  25                  30

Ala Ile Lys Gln Gly Ala Gly
        35

-continued

<210> SEQ ID NO 10
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 10

Ala Ser Glu Ser Lys Tyr Gly Pro Pro Cys Pro Pro Cys Pro
1               5                   10

<210> SEQ ID NO 11
<211> LENGTH: 1536
<212> TYPE: DNA
<213> ORGANISM: Artificial Sequence
<220> FEATURE:
<223> OTHER INFORMATION: Synthetic Polynucleotide

<400> SEQUENCE: 11
atgaagtgcc ttttgtactt agccttttta ttcattgggg tgaattgcaa gttcaccata 60
gtttttccac acaaccaaaa aggaaactgg aaaaatgttc cttctaatta ccattattgc 120
ccgtcaagct cagatttaaa ttggcataat gacttaatag gcacagccat acaagtcaaa 180
atgcccaaga gtcacaaggc tattcaagca gacggttgga tgtgtcatgc ttccaaatgg 240
gtcactactt gtgatttccg ctggtatgga ccgaagtata taacacagtc catccgatcc 300
ttcactccat ctgtagaaca atgcaaggaa agcattgaac aaacgaaaca aggaacttgg 360
ctgaatccag gcttccctcc tcaaagttgt ggatatgcaa ctgtgacgga tgccgaagca 420
gtgattgtcc aggtgactcc tcaccatgtg ctggttgatg aatacacagg agaatgggtt 480
gattcacagt tcatcaacgg aaaatgcagc aattacatat gccccactgt ccataactct 540
acaacctggc attctgacta taaggtcaaa gggctatgtg attctaacct catttccatg 600
gacatcacct tcttctcaga ggacggagag ctatcatccc tgggaaagga gggcacaggg 660
ttcagaagta actactttgc ttatgaaact ggaggcaagg cctgcaaaat gcaatactgc 720
aagcattggg gagtcagact cccatcaggt gtctggttcg agatggctga taaggatctc 780
tttgctgcag ccagattccc tgaatgccca gaagggtcaa gtatctctgc tccatctcag 840
acctcagtgg atgtaagtct aattcaggac gttgagagga tcttggatta ttccctctgc 900
caagaaacct ggagcaaaat cagagcgggt cttccaatct ctccagtgga tctcagctat 960
cttgctccta aaaacccagg aaccggtcct gctttcacca taatcaatgg taccctaaaa 1020
tactttgaga ccagatacat cagagtcgat attgctgctc caatcctctc aagaatggtc 1080
ggaatgatca gtggaactac cacagaaagg gaactgtggg atgactgggc accatatgaa 1140
gacgtggaaa ttggacccaa tggagttctg aggaccagtt caggatataa gtttccttta 1200
tacatgattg gacatggtat gttggactcc gatcttcatc ttagctcaaa ggctcaggtg 1260
ttcgaacatc ctcacattca agacgctgct tcgcaacttc ctgatgatga gagtttattt 1320
tttggtgata ctgggctatc caaaaatcca atcgagcttg tagaaggttg gttcagtagt 1380
tggaaaagct ctattgcctc ttttttcttt atcatagggt taatcattgg actattcttg 1440
gttctccgag ttggtatcca tctttgcatt aaattaaagc acaccaagaa aagacagatt 1500
tatacagaca tagagatgaa ccgacttgga aagtaa 1536

<210> SEQ ID NO 12
<211> LENGTH: 511
<212> TYPE: PRT
<213> ORGANISM: Artificial Sequence
<220> FEATURE:
<223> OTHER INFORMATION: Synthetic Polypeptide

<400> SEQUENCE: 12

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Ile Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr Gln
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400
```

Tyr Met Ile Gly His Gly Met Leu Asp Ser Asp Leu His Leu Ser Ser
405 410 415

Lys Ala Gln Val Phe Glu His Pro His Ile Gln Asp Ala Ala Ser Gln
420 425 430

Leu Pro Asp Asp Glu Ser Leu Phe Phe Gly Asp Thr Gly Leu Ser Lys
435 440 445

Asn Pro Ile Glu Leu Val Glu Gly Trp Phe Ser Ser Trp Lys Ser Ser
450 455 460

Ile Ala Ser Phe Phe Phe Ile Ile Gly Leu Ile Ile Gly Leu Phe Leu
465 470 475 480

Val Leu Arg Val Gly Ile His Leu Cys Ile Lys Leu Lys His Thr Lys
485 490 495

Lys Arg Gln Ile Tyr Thr Asp Ile Glu Met Asn Arg Leu Gly Lys
500 505 510

<210> SEQ ID NO 13
<211> LENGTH: 495
<212> TYPE: PRT
<213> ORGANISM: Artificial Sequence
<220> FEATURE:
<223> OTHER INFORMATION: Synthetic Polypeptide

<400> SEQUENCE: 13

Lys Phe Thr Ile Val Phe Pro His Asn Gln Lys Gly Asn Trp Lys Asn
1 5 10 15

Val Pro Ser Asn Tyr His Tyr Cys Pro Ser Ser Ser Asp Leu Asn Trp
20 25 30

His Asn Asp Leu Ile Gly Thr Ala Ile Gln Val Lys Met Pro Lys Ser
35 40 45

His Lys Ala Ile Gln Ala Asp Gly Trp Met Cys His Ala Ser Lys Trp
50 55 60

Val Thr Thr Cys Asp Phe Arg Trp Tyr Gly Pro Lys Tyr Ile Thr Gln
65 70 75 80

Ser Ile Arg Ser Phe Thr Pro Ser Val Glu Gln Cys Lys Glu Ser Ile
85 90 95

Glu Gln Thr Lys Gln Gly Thr Trp Leu Asn Pro Gly Phe Pro Pro Gln
100 105 110

Ser Cys Gly Tyr Ala Thr Val Thr Asp Ala Glu Ala Val Ile Val Gln
115 120 125

Val Thr Pro His His Val Leu Val Asp Glu Tyr Thr Gly Glu Trp Val
130 135 140

Asp Ser Gln Phe Ile Asn Gly Lys Cys Ser Asn Tyr Ile Cys Pro Thr
145 150 155 160

Val His Asn Ser Thr Thr Trp His Ser Asp Tyr Lys Val Lys Gly Leu
165 170 175

Cys Asp Ser Asn Leu Ile Ser Met Asp Ile Thr Phe Phe Ser Glu Asp
180 185 190

Gly Glu Leu Ser Ser Leu Gly Lys Glu Gly Thr Gly Phe Arg Ser Asn
195 200 205

Tyr Phe Ala Tyr Glu Thr Gly Gly Lys Ala Cys Lys Met Gln Tyr Cys
210 215 220

Lys His Trp Gly Val Arg Leu Pro Ser Gly Val Trp Phe Glu Met Ala
225 230 235 240

Asp Lys Asp Leu Phe Ala Ala Ala Arg Phe Pro Glu Cys Pro Glu Gly
245 250 255

```
Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Ser Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495
```

```
<210> SEQ ID NO 14
<211> LENGTH: 1536
<212> TYPE: DNA
<213> ORGANISM: Artificial Sequence
<220> FEATURE:
<223> OTHER INFORMATION: Synthetic Polynucleotide

<400> SEQUENCE: 14

atgaagtgcc ttttgtactt agccttttta ttcattgggg tgaattgcaa gttcaccata      60

gtttttccac acaaccaaaa aggaaactgg aaaaatgttc cttctaatta ccattattgc     120

ccgtcaagct cagatttaaa ttggcataat gacttaatag gcacagcctt acaagtcaaa     180

atgccccaga gtcacaaggc tattcaagca gacggttgga tgtgtcatgc ttccaaatgg     240

gtcactactt gtgatttccg ctggtatgga ccgaagtata taacacagtc catccgatcc     300

ttcactccat ctgtagaaca atgcaaggaa agcattgaac aaacgaaaca aggaacttgg     360

ctgaatccag gcttccctcc tcaaagttgt ggatatgcaa ctgtgacgga tgccgaagca     420

gtgattgtcc aggtgactcc tcaccatgtg ctggttgatg aatacacagg agaatgggtt     480

gattcacagt tcatcaacgg aaaatgcagc aattacatat gccccactgt ccataactct     540

acaacctggc attctgacta taaggtcaaa gggctatgtg attctaacct catttccatg     600

gacatcacct tcttctcaga ggacggagag ctatcatccc tgggaaagga gggcacaggg     660

ttcagaagta actactttgc ttatgaaact ggaggcaagg cctgcaaaat gcaatactgc     720
```

```
aagcattggg gagtcagact cccatcaggt gtctggttcg agatggctga taaggatctc    780

tttgctgcag ccagattccc tgaatgccca gaagggtcaa gtatctctgc tccatctcag    840

acctcagtgg atgtaagtct aattcaggac gttgagagga tcttggatta ttccctctgc    900

caagaaacct ggagcaaaat cagagcgggt cttccaatct ctccagtgga tctcagctat    960

cttgctccta aaaacccagg aaccggtcct gctttcacca taatcaatgg taccctaaaa   1020

tactttgaga ccagatacat cagagtcgat attgctgctc caatcctctc aagaatggtc   1080

ggaatgatca gtggaactac cacagaagcc gaactgtggg atgactgggc accatatgaa   1140

gacgtggaaa ttggacccaa tggagttctg aggaccagtt caggatataa gtttccttta   1200

tacatgattg gacatggtat gttggactcc gatcttcatc ttagctcaaa ggctcaggtg   1260

ttcgaacatc ctcacattca agacgctgct tcgcaacttc ctgatgatga gagtttattt   1320

tttggtgata ctgggctatc caaaaatcca atcgagcttg tagaaggttg gttcagtagt   1380

tggaaaagct ctattgcctc tttttcttt atcatagggt taatcattgg actattcttg   1440

gttctccgag ttggtatcca tctttgcatt aaattaaagc acaccaagaa aagacagatt   1500

tatacagaca tagagatgaa ccgacttgga aagtaa                             1536


<210> SEQ ID NO 15
<211> LENGTH: 511
<212> TYPE: PRT
<213> ORGANISM: Artificial Sequence
<220> FEATURE:
<223> OTHER INFORMATION: Synthetic Polypeptide

<400> SEQUENCE: 15

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Gln Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr Gln
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
```

```
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Ala Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys
            500                 505                 510


<210> SEQ ID NO 16
<211> LENGTH: 495
<212> TYPE: PRT
<213> ORGANISM: Artificial Sequence
<220> FEATURE:
<223> OTHER INFORMATION: Synthetic Polypeptide

<400> SEQUENCE: 16

Lys Phe Thr Ile Val Phe Pro His Asn Gln Lys Gly Asn Trp Lys Asn
1               5                   10                  15

Val Pro Ser Asn Tyr His Tyr Cys Pro Ser Ser Ser Asp Leu Asn Trp
            20                  25                  30

His Asn Asp Leu Ile Gly Thr Ala Leu Gln Val Lys Met Pro Gln Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
```

-continued

```
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Ala Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Ser Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495
```

<210> SEQ ID NO 17
<211> LENGTH: 495
<212> TYPE: PRT
<213> ORGANISM: Artificial Sequence
<220> FEATURE:
<223> OTHER INFORMATION: Synthetic Polypeptide

<400> SEQUENCE: 17

Lys Phe Thr Ile Val Phe Pro His Asn Gln Lys Gly Asn Trp Lys Asn
1 5 10 15

Val Pro Ser Asn Tyr His Tyr Cys Pro Ser Ser Ser Asp Leu Asn Trp
20 25 30

His Asn Asp Leu Ile Gly Thr Ala Ile Gln Val Lys Met Pro Gln Ser
35 40 45

His Lys Ala Ile Gln Ala Asp Gly Trp Met Cys His Ala Ser Lys Trp
50 55 60

Val Thr Thr Cys Asp Phe Arg Trp Tyr Gly Pro Lys Tyr Ile Thr Gln
65 70 75 80

Ser Ile Arg Ser Phe Thr Pro Ser Val Glu Gln Cys Lys Glu Ser Ile
85 90 95

Glu Gln Thr Lys Gln Gly Thr Trp Leu Asn Pro Gly Phe Pro Pro Gln
100 105 110

Ser Cys Gly Tyr Ala Thr Val Thr Asp Ala Glu Ala Val Ile Val Gln
115 120 125

Val Thr Pro His His Val Leu Val Asp Glu Tyr Thr Gly Glu Trp Val
130 135 140

Asp Ser Gln Phe Ile Asn Gly Lys Cys Ser Asn Tyr Ile Cys Pro Thr
145 150 155 160

Val His Asn Ser Thr Thr Trp His Ser Asp Tyr Lys Val Lys Gly Leu
165 170 175

Cys Asp Ser Asn Leu Ile Ser Met Asp Ile Thr Phe Phe Ser Glu Asp
180 185 190

Gly Glu Leu Ser Ser Leu Gly Lys Glu Gly Thr Gly Phe Arg Ser Asn
195 200 205

Tyr Phe Ala Tyr Glu Thr Gly Gly Lys Ala Cys Lys Met Gln Tyr Cys
210 215 220

Lys His Trp Gly Val Arg Leu Pro Ser Gly Val Trp Phe Glu Met Ala
225 230 235 240

Asp Lys Asp Leu Phe Ala Ala Ala Arg Phe Pro Glu Cys Pro Glu Gly
245 250 255

Ser Ser Ile Ser Ala Pro Ser Gln Thr Ser Val Asp Val Ser Leu Ile
260 265 270

Gln Asp Val Glu Arg Ile Leu Asp Tyr Ser Leu Cys Gln Glu Thr Trp
275 280 285

Ser Lys Ile Arg Ala Gly Leu Pro Ile Ser Pro Val Asp Leu Ser Tyr
290 295 300

Leu Ala Pro Lys Asn Pro Gly Thr Gly Pro Ala Phe Thr Ile Ile Asn
305 310 315 320

Gly Thr Leu Lys Tyr Phe Glu Thr Arg Tyr Ile Arg Val Asp Ile Ala
325 330 335

Ala Pro Ile Leu Ser Arg Met Val Gly Met Ile Ser Gly Thr Thr Thr
340 345 350

Glu Ala Glu Leu Trp Asp Asp Trp Ala Pro Tyr Glu Asp Val Glu Ile
355 360 365

```
Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Ser Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495


<210> SEQ ID NO 18
<211> LENGTH: 1818
<212> TYPE: PRT
<213> ORGANISM: Artificial Sequence
<220> FEATURE:
<223> OTHER INFORMATION: Synthetic Polypeptide

<400> SEQUENCE: 18

Ala Thr Gly Gly Gly Cys Ala Gly Cys Cys Gly Gly Ala Thr Cys Gly
1               5                   10                  15

Thr Gly Ala Thr Cys Ala Ala Cys Cys Gly Gly Gly Ala Gly Cys Ala
            20                  25                  30

Cys Cys Thr Gly Ala Thr Gly Ala Thr Cys Gly Ala Cys Cys Gly Gly
        35                  40                  45

Cys Cys Cys Thr Ala Cys Gly Thr Gly Cys Thr Gly Cys Thr Gly Gly
    50                  55                  60

Cys Cys Gly Thr Gly Cys Thr Gly Thr Thr Cys Gly Thr Gly Ala Thr
65                  70                  75                  80

Gly Thr Thr Cys Cys Thr Gly Ala Gly Cys Cys Thr Gly Ala Thr Cys
                85                  90                  95

Gly Gly Cys Thr Thr Gly Cys Thr Ala Gly Cys Cys Ala Thr Thr Gly
            100                 105                 110

Cys Thr Gly Gly Ala Ala Thr Cys Cys Gly Gly Cys Thr Gly Cys Ala
        115                 120                 125

Cys Ala Gly Ala Gly Cys Cys Gly Cys Cys Ala Thr Cys Thr Ala Cys
    130                 135                 140

Ala Cys Cys Gly Cys Cys Gly Ala Gly Ala Thr Cys Cys Ala Cys Ala
145                 150                 155                 160

Ala Gly Ala Gly Cys Cys Thr Gly Ala Gly Cys Ala Cys Cys Ala Ala
                165                 170                 175

Cys Cys Thr Gly Gly Ala Cys Gly Thr Gly Ala Cys Cys Ala Ala Cys
            180                 185                 190

Ala Gly Cys Ala Thr Cys Gly Ala Gly Cys Ala Thr Cys Ala Gly Gly
        195                 200                 205

Thr Cys Ala Ala Gly Gly Ala Cys Gly Thr Gly Cys Thr Gly Ala Cys
    210                 215                 220

Cys Cys Cys Cys Cys Thr Gly Thr Thr Thr Ala Ala Gly Ala Thr Cys
225                 230                 235                 240
```

-continued

```
Ala Thr Cys Gly Gly Cys Gly Ala Cys Gly Ala Ala Gly Thr Gly Gly
                245                 250                 255

Gly Cys Cys Thr Gly Cys Gly Gly Ala Cys Cys Cys Cys Cys Cys Ala
            260                 265                 270

Gly Ala Gly Ala Thr Thr Cys Ala Cys Cys Gly Ala Cys Cys Thr Gly
        275                 280                 285

Gly Thr Cys Ala Ala Gly Thr Thr Cys Ala Thr Cys Ala Gly Cys Gly
    290                 295                 300

Ala Cys Ala Ala Gly Ala Thr Cys Ala Ala Gly Thr Thr Cys Cys Thr
305                 310                 315                 320

Gly Ala Ala Cys Cys Cys Cys Gly Ala Cys Cys Gly Gly Gly Ala Gly
                325                 330                 335

Thr Ala Cys Gly Ala Cys Thr Thr Cys Cys Gly Gly Gly Ala Cys Cys
            340                 345                 350

Thr Gly Ala Cys Cys Thr Gly Gly Thr Gly Cys Ala Thr Cys Ala Ala
        355                 360                 365

Cys Cys Cys Cys Cys Cys Cys Gly Ala Gly Cys Gly Gly Ala Thr Cys
    370                 375                 380

Ala Ala Gly Cys Thr Gly Gly Ala Cys Thr Ala Cys Gly Ala Cys Cys
385                 390                 395                 400

Ala Gly Thr Ala Cys Thr Gly Cys Gly Cys Cys Gly Ala Thr Gly Thr
                405                 410                 415

Gly Gly Cys Cys Gly Cys Cys Gly Ala Gly Gly Ala Ala Cys Thr Gly
            420                 425                 430

Ala Thr Gly Ala Ala Thr Gly Cys Ala Thr Thr Gly Gly Thr Gly Ala
        435                 440                 445

Ala Cys Thr Cys Ala Ala Cys Thr Cys Thr Ala Cys Thr Gly Gly Ala
    450                 455                 460

Gly Ala Cys Cys Ala Gly Ala Ala Cys Ala Ala Cys Cys Ala Ala Thr
465                 470                 475                 480

Cys Ala Gly Thr Thr Cys Cys Thr Ala Gly Cys Thr Gly Thr Cys Thr
                485                 490                 495

Cys Ala Ala Ala Gly Gly Gly Ala Ala Ala Cys Thr Gly Cys Thr Cys
            500                 505                 510

Ala Gly Gly Gly Cys Cys Cys Ala Cys Thr Ala Cys Ala Ala Thr Cys
        515                 520                 525

Ala Gly Ala Gly Gly Thr Cys Ala Ala Thr Thr Cys Thr Cys Ala Ala
    530                 535                 540

Ala Cys Ala Thr Gly Thr Cys Gly Cys Thr Gly Thr Cys Cys Cys Thr
545                 550                 555                 560

Gly Thr Thr Ala Gly Ala Cys Thr Thr Gly Thr Ala Thr Thr Thr Ala
                565                 570                 575

Gly Gly Thr Cys Gly Ala Gly Gly Thr Thr Ala Cys Ala Ala Thr Gly
            580                 585                 590

Thr Gly Thr Cys Ala Thr Cys Thr Ala Thr Ala Gly Thr Cys Ala Cys
        595                 600                 605

Thr Ala Thr Gly Ala Cys Ala Thr Cys Cys Cys Ala Gly Gly Gly Ala
    610                 615                 620

Ala Thr Gly Thr Ala Thr Gly Gly Gly Gly Gly Ala Ala Cys Thr Thr
625                 630                 635                 640

Ala Cys Cys Thr Ala Gly Thr Gly Gly Ala Ala Ala Ala Gly Cys Cys
                645                 650                 655
```

-continued

```
Thr Ala Ala Thr Cys Thr Gly Ala Gly Cys Ala Gly Cys Ala Ala Ala
            660                 665                 670

Ala Gly Gly Thr Cys Ala Gly Ala Gly Thr Thr Gly Thr Cys Ala Cys
        675                 680                 685

Ala Ala Cys Thr Gly Ala Gly Cys Ala Thr Gly Thr Ala Cys Cys Gly
    690                 695                 700

Ala Gly Thr Gly Thr Thr Thr Gly Ala Ala Gly Thr Ala Gly Gly Thr
705                 710                 715                 720

Gly Thr Thr Ala Thr Cys Ala Gly Ala Ala Ala Thr Cys Cys Gly Gly
                725                 730                 735

Gly Thr Thr Thr Gly Gly Gly Gly Gly Cys Thr Cys Cys Gly Gly Thr
            740                 745                 750

Gly Thr Thr Cys Cys Ala Thr Ala Thr Gly Ala Cys Ala Ala Ala Cys
        755                 760                 765

Thr Ala Thr Cys Thr Thr Gly Ala Gly Cys Ala Ala Cys Cys Ala Gly
    770                 775                 780

Thr Cys Ala Gly Thr Ala Ala Thr Gly Ala Thr Cys Thr Cys Ala Gly
785                 790                 795                 800

Cys Ala Ala Cys Thr Gly Thr Ala Thr Gly Gly Thr Gly Gly Cys Thr
                805                 810                 815

Thr Thr Gly Gly Gly Gly Ala Gly Cys Thr Cys Ala Ala Ala Cys
            820                 825                 830

Thr Cys Gly Cys Ala Gly Cys Cys Cys Thr Thr Thr Gly Thr Cys Ala
        835                 840                 845

Cys Gly Gly Gly Gly Ala Ala Gly Ala Thr Thr Cys Thr Ala Thr Cys
    850                 855                 860

Ala Cys Ala Ala Thr Thr Cys Cys Cys Thr Ala Thr Cys Ala Gly Gly
865                 870                 875                 880

Gly Ala Thr Cys Ala Gly Gly Gly Ala Ala Ala Gly Gly Thr Gly Thr
                885                 890                 895

Cys Ala Gly Cys Thr Thr Cys Cys Ala Gly Cys Thr Cys Gly Thr Cys
            900                 905                 910

Ala Ala Gly Cys Thr Ala Gly Gly Thr Gly Thr Cys Thr Gly Gly Ala
        915                 920                 925

Ala Ala Thr Cys Cys Cys Cys Ala Ala Cys Cys Gly Ala Cys Ala Thr
    930                 935                 940

Gly Cys Ala Ala Thr Cys Cys Thr Gly Gly Gly Thr Cys Cys Cys Cys
945                 950                 955                 960

Thr Thr Ala Thr Cys Ala Ala Cys Gly Gly Ala Thr Gly Ala Thr Cys
                965                 970                 975

Cys Ala Gly Thr Gly Ala Thr Ala Gly Ala Cys Ala Gly Gly Cys Thr
            980                 985                 990

Thr Thr Ala Cys Cys Thr Cys Thr  Cys Ala Thr Cys Thr  Cys Ala Cys
        995                 1000                1005

Ala Gly  Ala Gly Gly Thr Gly  Thr Thr Ala Thr Cys  Gly Cys Thr
    1010                1015                1020

Gly Ala  Cys Ala Ala Cys Cys  Ala Ala Gly Cys Ala  Ala Ala Ala
    1025                1030                1035

Thr Gly  Gly Gly Cys Thr Gly  Thr Cys Cys Cys Gly  Ala Cys Ala
    1040                1045                1050

Ala Cys  Ala Cys Gly Ala Ala  Cys Ala Gly Ala Thr  Gly Ala Cys
    1055                1060                1065

Ala Ala  Gly Thr Thr Gly Cys  Gly Ala Ala Thr Gly  Gly Ala Gly
```

```
    1070                1075                1080

Ala Cys  Ala Thr Gly Cys Thr  Thr Cys Cys Ala Ala  Cys Ala Gly
    1085                1090                1095

Gly Cys  Gly Thr Gly Thr Ala  Ala Gly Gly Gly Thr  Ala Ala Ala
    1100                1105                1110

Ala Thr  Cys Cys Ala Ala Gly  Cys Ala Cys Thr Cys  Thr Gly Cys
    1115                1120                1125

Gly Ala  Gly Ala Ala Thr Cys  Cys Cys Gly Ala Gly  Thr Gly Gly
    1130                1135                1140

Gly Cys  Ala Cys Cys Ala Thr  Thr Gly Ala Ala Gly  Gly Ala Thr
    1145                1150                1155

Ala Ala  Cys Ala Gly Gly Ala  Thr Thr Cys Cys Thr  Thr Cys Ala
    1160                1165                1170

Thr Ala  Cys Gly Gly Gly Gly  Thr Cys Thr Thr Gly  Thr Cys Thr
    1175                1180                1185

Gly Thr  Thr Gly Ala Thr Cys  Thr Gly Ala Gly Thr  Cys Thr Gly
    1190                1195                1200

Ala Cys  Ala Gly Thr Thr Gly  Ala Gly Cys Thr Thr  Ala Ala Ala
    1205                1210                1215

Ala Thr  Cys Ala Ala Ala Ala  Thr Thr Gly Cys Thr  Thr Cys Gly
    1220                1225                1230

Gly Gly  Ala Thr Thr Cys Gly  Gly Gly Cys Cys Ala  Thr Thr Gly
    1235                1240                1245

Ala Thr  Cys Ala Cys Ala Cys  Ala Cys Gly Gly Thr  Thr Cys Ala
    1250                1255                1260

Gly Gly  Gly Ala Thr Gly Gly  Ala Cys Cys Thr Ala  Thr Ala Cys
    1265                1270                1275

Ala Ala  Ala Thr Cys Cys Ala  Ala Cys Cys Ala Cys  Ala Ala Cys
    1280                1285                1290

Ala Ala  Thr Gly Thr Gly Thr  Ala Thr Thr Gly Gly  Cys Thr Gly
    1295                1300                1305

Ala Cys  Thr Ala Thr Cys Cys  Cys Gly Cys Cys Ala  Ala Thr Gly
    1310                1315                1320

Ala Ala  Gly Ala Ala Cys Cys  Thr Ala Gly Cys Cys  Thr Thr Ala
    1325                1330                1335

Gly Gly  Thr Gly Thr Ala Ala  Thr Cys Ala Ala Cys  Ala Cys Ala
    1340                1345                1350

Thr Thr  Gly Gly Ala Gly Thr  Gly Gly Ala Thr Ala  Cys Cys Gly
    1355                1360                1365

Ala Gly  Ala Thr Thr Cys Ala  Ala Gly Gly Thr Thr  Ala Gly Thr
    1370                1375                1380

Cys Cys  Cys Thr Ala Thr Cys  Thr Cys Thr Thr Cys  Ala Cys Ala
    1385                1390                1395

Gly Thr  Cys Cys Cys Ala Ala  Thr Thr Ala Ala Gly  Gly Ala Ala
    1400                1405                1410

Gly Cys  Ala Gly Gly Cys Gly  Gly Ala Gly Ala Cys  Thr Gly Cys
    1415                1420                1425

Cys Ala  Thr Gly Cys Cys Cys  Cys Ala Ala Cys Ala  Thr Ala Cys
    1430                1435                1440

Cys Thr  Ala Cys Cys Thr Gly  Cys Gly Gly Ala Gly  Gly Thr Gly
    1445                1450                1455

Gly Ala  Thr Gly Gly Thr Gly  Ala Thr Gly Thr Cys  Ala Ala Ala
    1460                1465                1470
```

```
Cys Thr Cys Ala Gly Thr Thr Cys Cys Ala Ala Thr Cys Thr Gly
    1475                1480                1485

Gly Thr Gly Ala Thr Thr Cys Thr Ala Cys Cys Thr Gly Gly Thr
    1490                1495                1500

Cys Ala Ala Gly Ala Thr Cys Thr Cys Cys Ala Ala Thr Ala Thr
    1505                1510                1515

Gly Thr Thr Thr Thr Gly Gly Cys Ala Ala Cys Cys Thr Ala Cys
    1520                1525                1530

Gly Ala Thr Ala Cys Thr Thr Cys Cys Cys Gly Gly Gly Thr Thr
    1535                1540                1545

Gly Ala Ala Cys Ala Thr Gly Cys Thr Gly Thr Gly Gly Thr Thr
    1550                1555                1560

Thr Ala Thr Thr Ala Cys Gly Thr Thr Thr Ala Cys Ala Gly Cys
    1565                1570                1575

Cys Cys Ala Ala Gly Cys Cys Gly Cys Thr Cys Ala Thr Thr Thr
    1580                1585                1590

Thr Cys Thr Thr Ala Cys Thr Thr Thr Thr Ala Thr Cys Cys Thr
    1595                1600                1605

Thr Thr Thr Ala Gly Gly Thr Thr Gly Cys Cys Thr Ala Thr Ala
    1610                1615                1620

Ala Ala Gly Gly Gly Gly Gly Thr Cys Cys Cys Cys Ala Thr Cys
    1625                1630                1635

Gly Ala Ala Thr Thr Ala Cys Ala Ala Gly Thr Gly Gly Ala Ala
    1640                1645                1650

Thr Gly Cys Thr Thr Cys Ala Cys Ala Thr Gly Gly Gly Ala Cys
    1655                1660                1665

Cys Ala Ala Ala Ala Ala Cys Thr Cys Thr Gly Gly Thr Gly Cys
    1670                1675                1680

Cys Gly Thr Cys Ala Cys Thr Thr Cys Thr Gly Thr Gly Thr Gly
    1685                1690                1695

Cys Thr Thr Gly Cys Gly Gly Ala Cys Thr Cys Ala Gly Ala Ala
    1700                1705                1710

Thr Cys Thr Gly Gly Thr Gly Gly Ala Cys Ala Thr Ala Thr Cys
    1715                1720                1725

Ala Cys Thr Cys Ala Cys Thr Cys Thr Gly Gly Gly Ala Thr Gly
    1730                1735                1740

Gly Thr Gly Gly Gly Cys Ala Thr Gly Gly Gly Ala Gly Thr Cys
    1745                1750                1755

Ala Gly Cys Thr Gly Cys Ala Cys Ala Gly Thr Cys Ala Cys Cys
    1760                1765                1770

Cys Gly Gly Gly Ala Ala Gly Ala Thr Gly Gly Ala Ala Cys Cys
    1775                1780                1785

Ala Ala Thr Gly Ala Cys Thr Ala Cys Ala Ala Ala Gly Ala Cys
    1790                1795                1800

Gly Ala Thr Gly Ala Cys Gly Ala Cys Ala Ala Gly Thr Gly Ala
    1805                1810                1815
```

<210> SEQ ID NO 19
<211> LENGTH: 605
<212> TYPE: PRT
<213> ORGANISM: Artificial Sequence
<220> FEATURE:
<223> OTHER INFORMATION: Synthetic Polypeptide

<400> SEQUENCE: 19

```
Met Gly Ser Arg Ile Val Ile Asn Arg Glu His Leu Met Ile Asp Arg
1               5                   10                  15

Pro Tyr Val Leu Leu Ala Val Leu Phe Val Met Phe Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
            100                 105                 110

Tyr Asp Phe Arg Asp Leu Thr Trp Cys Ile Asn Pro Pro Glu Arg Ile
        115                 120                 125

Lys Leu Asp Tyr Asp Gln Tyr Cys Ala Asp Val Ala Ala Glu Glu Leu
    130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
            180                 185                 190

Gly Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                245                 250                 255

Tyr Leu Glu Gln Pro Val Ser Asn Asp Leu Ser Asn Cys Met Val Ala
            260                 265                 270

Leu Gly Glu Leu Lys Leu Ala Ala Leu Cys His Gly Glu Asp Ser Ile
        275                 280                 285

Thr Ile Pro Tyr Gln Gly Ser Gly Lys Gly Val Ser Phe Gln Leu Val
    290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                325                 330                 335

Arg Gly Val Ile Ala Asp Asn Gln Ala Lys Trp Ala Val Pro Thr Thr
            340                 345                 350

Arg Thr Asp Asp Lys Leu Arg Met Glu Thr Cys Phe Gln Gln Ala Cys
        355                 360                 365

Lys Gly Lys Ile Gln Ala Leu Cys Glu Asn Pro Glu Trp Ala Pro Leu
    370                 375                 380

Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
                405                 410                 415
```

```
Ile Thr His Gly Ser Gly Met Asp Leu Tyr Lys Ser Asn His Asn Asn
            420                 425                 430

Val Tyr Trp Leu Thr Ile Pro Pro Met Lys Asn Leu Ala Leu Gly Val
        435                 440                 445

Ile Asn Thr Leu Glu Trp Ile Pro Arg Phe Lys Val Ser Pro Tyr Leu
    450                 455                 460

Phe Thr Val Pro Ile Lys Glu Ala Gly Gly Asp Cys His Ala Pro Thr
465                 470                 475                 480

Tyr Leu Pro Ala Glu Val Asp Gly Asp Val Lys Leu Ser Ser Asn Leu
                485                 490                 495

Val Ile Leu Pro Gly Gln Asp Leu Gln Tyr Val Leu Ala Thr Tyr Asp
            500                 505                 510

Thr Ser Arg Val Glu His Ala Val Val Tyr Tyr Val Tyr Ser Pro Ser
        515                 520                 525

Arg Ser Phe Ser Tyr Phe Tyr Pro Phe Arg Leu Pro Ile Lys Gly Val
    530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
                565                 570                 575

Thr His Ser Gly Met Val Gly Met Gly Val Ser Cys Thr Val Thr Arg
            580                 585                 590

Glu Asp Gly Thr Asn Asp Tyr Lys Asp Asp Asp Asp Lys
        595                 600                 605


<210> SEQ ID NO 20
<211> LENGTH: 1818
<212> TYPE: PRT
<213> ORGANISM: Artificial Sequence
<220> FEATURE:
<223> OTHER INFORMATION: Synthetic Polypeptide

<400> SEQUENCE: 20

Ala Thr Gly Gly Gly Cys Ala Gly Cys Cys Gly Gly Ala Thr Cys Gly
1               5                   10                  15

Thr Gly Ala Thr Cys Ala Ala Cys Cys Gly Gly Gly Ala Gly Cys Ala
            20                  25                  30

Cys Cys Thr Gly Ala Thr Gly Ala Thr Cys Gly Ala Cys Cys Gly Gly
        35                  40                  45

Cys Cys Cys Thr Ala Cys Gly Thr Gly Cys Thr Gly Cys Thr Gly Gly
    50                  55                  60

Cys Cys Gly Thr Gly Cys Thr Gly Thr Thr Cys Gly Thr Gly Ala Thr
65                  70                  75                  80

Gly Thr Thr Cys Cys Thr Gly Ala Gly Cys Cys Thr Gly Ala Thr Cys
                85                  90                  95

Gly Gly Cys Thr Thr Gly Cys Thr Ala Gly Cys Cys Ala Thr Thr Gly
            100                 105                 110

Cys Thr Gly Gly Ala Ala Thr Cys Cys Gly Gly Cys Thr Gly Cys Ala
        115                 120                 125

Cys Ala Gly Ala Gly Cys Cys Gly Cys Cys Ala Thr Cys Thr Ala Cys
    130                 135                 140

Ala Cys Cys Gly Cys Cys Gly Ala Gly Ala Thr Cys Cys Ala Cys Ala
145                 150                 155                 160

Ala Gly Ala Gly Cys Cys Thr Gly Ala Gly Cys Ala Cys Cys Ala Ala
                165                 170                 175
```

-continued

```
Cys Cys Thr Gly Gly Ala Cys Gly Thr Gly Ala Cys Cys Ala Ala Cys
            180                 185                 190

Ala Gly Cys Ala Thr Cys Gly Ala Gly Cys Ala Thr Cys Ala Gly Gly
        195                 200                 205

Thr Cys Ala Ala Gly Gly Ala Cys Gly Thr Gly Cys Thr Gly Ala Cys
    210                 215                 220

Cys Cys Cys Cys Cys Thr Gly Thr Thr Thr Ala Ala Gly Ala Thr Cys
225                 230                 235                 240

Ala Thr Cys Gly Gly Cys Gly Ala Cys Gly Ala Ala Gly Thr Gly Gly
                245                 250                 255

Gly Cys Cys Thr Gly Cys Gly Gly Ala Cys Cys Cys Cys Cys Cys Ala
            260                 265                 270

Gly Ala Gly Ala Thr Thr Cys Ala Cys Cys Gly Ala Cys Cys Thr Gly
        275                 280                 285

Gly Thr Cys Ala Ala Gly Thr Thr Cys Ala Thr Cys Ala Gly Cys Gly
    290                 295                 300

Ala Cys Ala Ala Gly Ala Thr Cys Ala Ala Gly Thr Thr Cys Cys Thr
305                 310                 315                 320

Gly Ala Ala Cys Cys Cys Cys Gly Ala Cys Cys Gly Gly Gly Ala Gly
                325                 330                 335

Thr Ala Cys Gly Ala Cys Thr Thr Cys Cys Gly Gly Gly Ala Cys Cys
            340                 345                 350

Thr Gly Ala Cys Cys Thr Gly Gly Thr Gly Cys Ala Thr Cys Ala Ala
        355                 360                 365

Cys Cys Cys Cys Cys Cys Cys Gly Ala Gly Cys Gly Gly Ala Thr Cys
    370                 375                 380

Ala Ala Gly Cys Thr Gly Gly Ala Cys Thr Ala Cys Gly Ala Cys Cys
385                 390                 395                 400

Ala Gly Thr Ala Cys Thr Gly Cys Gly Cys Cys Gly Ala Thr Gly Thr
                405                 410                 415

Gly Gly Cys Cys Gly Cys Cys Gly Ala Gly Gly Ala Ala Cys Thr Gly
            420                 425                 430

Ala Thr Gly Ala Ala Thr Gly Cys Ala Thr Thr Gly Gly Thr Gly Ala
        435                 440                 445

Ala Cys Thr Cys Ala Ala Cys Thr Cys Thr Ala Cys Thr Gly Gly Ala
    450                 455                 460

Gly Ala Cys Cys Ala Gly Ala Ala Cys Ala Ala Cys Cys Ala Ala Thr
465                 470                 475                 480

Cys Ala Gly Thr Thr Cys Cys Thr Ala Gly Cys Thr Gly Thr Cys Thr
                485                 490                 495

Cys Ala Ala Ala Gly Gly Gly Ala Ala Ala Cys Thr Gly Cys Thr Cys
            500                 505                 510

Ala Gly Gly Gly Cys Cys Cys Ala Cys Thr Ala Cys Ala Ala Thr Cys
        515                 520                 525

Ala Gly Ala Gly Gly Thr Cys Ala Ala Thr Thr Cys Thr Cys Ala Ala
    530                 535                 540

Ala Cys Ala Thr Gly Thr Cys Gly Cys Thr Gly Thr Cys Cys Cys Thr
545                 550                 555                 560

Gly Thr Thr Ala Gly Ala Cys Thr Thr Gly Thr Ala Thr Thr Thr Ala
                565                 570                 575

Gly Gly Thr Cys Gly Ala Gly Gly Thr Thr Ala Cys Ala Ala Thr Gly
            580                 585                 590

Thr Gly Thr Cys Ala Thr Cys Thr Ala Thr Ala Gly Thr Cys Ala Cys
```

-continued

```
        595                 600                 605

Thr Ala Thr Gly Ala Cys Ala Thr Cys Cys Cys Ala Gly Gly Gly Ala
    610                 615                 620

Ala Thr Gly Thr Ala Thr Gly Gly Gly Gly Gly Ala Ala Cys Thr Thr
625                 630                 635                 640

Ala Cys Cys Thr Ala Gly Thr Gly Gly Ala Ala Ala Ala Gly Cys Cys
                645                 650                 655

Thr Ala Ala Thr Cys Thr Gly Ala Gly Cys Ala Gly Cys Ala Ala Ala
            660                 665                 670

Ala Gly Gly Thr Cys Ala Gly Ala Gly Thr Thr Gly Thr Cys Ala Cys
        675                 680                 685

Ala Ala Cys Thr Gly Ala Gly Cys Ala Thr Gly Thr Ala Cys Cys Gly
    690                 695                 700

Ala Gly Thr Gly Thr Thr Thr Gly Ala Ala Gly Thr Ala Gly Gly Thr
705                 710                 715                 720

Gly Thr Thr Ala Thr Cys Ala Gly Ala Ala Ala Thr Cys Cys Gly Gly
                725                 730                 735

Gly Thr Thr Thr Gly Gly Gly Gly Gly Cys Thr Cys Cys Gly Gly Thr
            740                 745                 750

Gly Thr Thr Cys Cys Ala Thr Ala Thr Gly Ala Cys Ala Ala Ala Cys
        755                 760                 765

Thr Ala Thr Cys Thr Thr Gly Ala Gly Cys Ala Ala Cys Cys Ala Gly
    770                 775                 780

Thr Cys Ala Gly Thr Ala Ala Thr Gly Ala Thr Cys Thr Cys Ala Gly
785                 790                 795                 800

Cys Ala Ala Cys Thr Gly Thr Ala Thr Gly Gly Thr Gly Gly Cys Thr
                805                 810                 815

Thr Thr Gly Gly Gly Gly Gly Ala Gly Cys Thr Cys Ala Ala Ala Cys
            820                 825                 830

Thr Cys Gly Cys Ala Gly Cys Cys Cys Thr Thr Thr Gly Thr Cys Ala
        835                 840                 845

Cys Gly Gly Gly Gly Ala Ala Gly Ala Thr Thr Cys Thr Ala Thr Cys
    850                 855                 860

Ala Cys Ala Ala Thr Thr Cys Cys Cys Thr Ala Thr Cys Ala Gly Gly
865                 870                 875                 880

Gly Ala Thr Cys Ala Gly Gly Gly Ala Ala Gly Gly Thr Gly Thr
                885                 890                 895

Cys Ala Gly Cys Thr Thr Cys Cys Ala Gly Cys Thr Cys Gly Thr Cys
            900                 905                 910

Ala Ala Gly Cys Thr Ala Gly Gly Thr Gly Thr Cys Thr Gly Gly Ala
        915                 920                 925

Ala Ala Thr Cys Cys Cys Cys Ala Ala Cys Cys Gly Ala Cys Ala Thr
    930                 935                 940

Gly Cys Ala Ala Thr Cys Cys Thr Gly Gly Gly Thr Cys Cys Cys Cys
945                 950                 955                 960

Thr Thr Ala Thr Cys Ala Ala Cys Gly Gly Ala Thr Gly Ala Thr Cys
                965                 970                 975

Cys Ala Gly Thr Gly Ala Thr Ala Gly Ala Cys Ala Gly Gly Cys Thr
            980                 985                 990

Thr Thr Ala Cys Cys Thr Cys Thr  Cys Ala Thr Cys Thr  Cys Ala Cys
        995                 1000                1005

Ala Gly  Ala Gly Gly Thr Gly  Thr Thr Ala Thr Cys  Gly Cys Thr
    1010                1015                1020
```

-continued

Gly Ala Cys Ala Ala Cys Cys Ala Ala Gly Cys Ala Ala Ala Ala
1025 1030 1035

Thr Gly Gly Gly Cys Thr Gly Thr Cys Cys Cys Gly Ala Cys Ala
1040 1045 1050

Ala Cys Ala Cys Gly Ala Ala Cys Ala Gly Ala Thr Gly Ala Cys
1055 1060 1065

Ala Ala Gly Thr Thr Gly Cys Gly Ala Ala Thr Gly Gly Ala Gly
1070 1075 1080

Ala Cys Ala Thr Gly Cys Thr Thr Cys Cys Ala Ala Cys Ala Gly
1085 1090 1095

Gly Cys Gly Thr Gly Thr Ala Ala Gly Gly Gly Thr Ala Ala Ala
1100 1105 1110

Ala Thr Cys Cys Ala Ala Gly Cys Ala Cys Thr Cys Thr Gly Cys
1115 1120 1125

Gly Ala Gly Ala Ala Thr Cys Cys Cys Gly Ala Gly Thr Gly Gly
1130 1135 1140

Gly Cys Ala Cys Cys Ala Thr Thr Gly Ala Ala Gly Gly Ala Thr
1145 1150 1155

Ala Ala Cys Ala Gly Gly Ala Thr Thr Cys Cys Thr Thr Cys Ala
1160 1165 1170

Thr Ala Cys Gly Gly Gly Gly Thr Cys Thr Thr Gly Thr Cys Thr
1175 1180 1185

Gly Thr Thr Gly Ala Thr Cys Thr Gly Ala Gly Thr Cys Thr Gly
1190 1195 1200

Ala Cys Ala Gly Thr Thr Gly Ala Gly Cys Thr Thr Ala Ala Ala
1205 1210 1215

Ala Thr Cys Ala Ala Ala Ala Thr Thr Gly Cys Thr Thr Cys Gly
1220 1225 1230

Gly Gly Ala Thr Thr Cys Gly Gly Gly Cys Cys Ala Thr Thr Gly
1235 1240 1245

Ala Thr Cys Ala Cys Ala Cys Ala Cys Gly Gly Thr Thr Cys Ala
1250 1255 1260

Gly Gly Gly Ala Thr Gly Gly Ala Cys Cys Thr Ala Thr Ala Cys
1265 1270 1275

Ala Ala Ala Thr Cys Cys Ala Ala Cys Cys Ala Cys Ala Ala Cys
1280 1285 1290

Ala Ala Thr Gly Thr Gly Thr Ala Thr Thr Gly Gly Cys Thr Gly
1295 1300 1305

Ala Cys Thr Ala Thr Cys Cys Cys Gly Cys Cys Ala Ala Thr Gly
1310 1315 1320

Ala Ala Gly Ala Ala Cys Cys Thr Ala Gly Cys Cys Thr Thr Ala
1325 1330 1335

Gly Gly Thr Gly Thr Ala Ala Thr Cys Ala Ala Cys Ala Cys Ala
1340 1345 1350

Thr Thr Gly Gly Ala Gly Thr Gly Gly Ala Thr Ala Cys Cys Gly
1355 1360 1365

Ala Gly Ala Thr Thr Cys Ala Ala Gly Gly Thr Thr Ala Gly Thr
1370 1375 1380

Cys Cys Cys Gly Cys Gly Cys Thr Cys Thr Thr Cys Ala Ala Thr
1385 1390 1395

Gly Thr Cys Cys Cys Ala Ala Thr Thr Ala Ala Gly Gly Ala Ala
1400 1405 1410

Gly Cys Ala Gly Gly Cys Gly Gly Ala Gly Ala Cys Thr Gly Cys
1415 1420 1425

Cys Ala Thr Gly Cys Cys Cys Cys Ala Ala Cys Ala Thr Ala Cys
1430 1435 1440

Cys Thr Ala Cys Cys Thr Gly Cys Gly Gly Ala Gly Gly Thr Gly
1445 1450 1455

Gly Ala Thr Gly Gly Thr Gly Ala Thr Gly Thr Cys Ala Ala Ala
1460 1465 1470

Cys Thr Cys Ala Gly Thr Thr Cys Cys Ala Ala Thr Cys Thr Gly
1475 1480 1485

Gly Thr Gly Ala Thr Thr Cys Thr Ala Cys Cys Thr Gly Gly Thr
1490 1495 1500

Cys Ala Ala Gly Ala Thr Cys Thr Cys Cys Ala Ala Thr Ala Thr
1505 1510 1515

Gly Thr Thr Thr Thr Gly Gly Cys Ala Ala Cys Cys Thr Ala Cys
1520 1525 1530

Gly Ala Thr Ala Cys Thr Thr Cys Cys Gly Cys Gly Gly Thr Thr
1535 1540 1545

Gly Ala Ala Cys Ala Thr Gly Cys Thr Gly Thr Gly Gly Thr Thr
1550 1555 1560

Thr Ala Thr Thr Ala Cys Gly Thr Thr Thr Ala Cys Ala Gly Cys
1565 1570 1575

Cys Cys Ala Ala Gly Cys Cys Gly Cys Thr Cys Ala Thr Thr Thr
1580 1585 1590

Thr Cys Thr Thr Ala Cys Thr Thr Thr Thr Ala Thr Cys Cys Thr
1595 1600 1605

Thr Thr Thr Ala Gly Gly Thr Thr Gly Cys Cys Thr Ala Thr Ala
1610 1615 1620

Ala Ala Gly Gly Gly Gly Gly Thr Cys Cys Cys Cys Ala Thr Cys
1625 1630 1635

Gly Ala Ala Thr Thr Ala Cys Ala Ala Gly Thr Gly Gly Ala Ala
1640 1645 1650

Thr Gly Cys Thr Thr Cys Ala Cys Ala Thr Gly Gly Gly Ala Cys
1655 1660 1665

Cys Ala Ala Ala Ala Ala Cys Thr Cys Thr Gly Gly Thr Gly Cys
1670 1675 1680

Cys Gly Thr Cys Ala Cys Thr Thr Cys Thr Gly Thr Gly Thr Gly
1685 1690 1695

Cys Thr Thr Gly Cys Gly Gly Ala Cys Thr Cys Ala Gly Ala Ala
1700 1705 1710

Thr Cys Thr Gly Gly Thr Gly Gly Ala Cys Ala Thr Ala Thr Cys
1715 1720 1725

Ala Cys Thr Cys Ala Cys Thr Cys Thr Gly Gly Gly Ala Thr Gly
1730 1735 1740

Gly Thr Gly Gly Gly Cys Ala Thr Gly Gly Gly Ala Gly Thr Cys
1745 1750 1755

Ala Gly Cys Thr Gly Cys Ala Cys Ala Gly Thr Cys Ala Cys Cys
1760 1765 1770

Cys Gly Gly Gly Ala Ala Gly Ala Thr Gly Gly Ala Ala Cys Cys
1775 1780 1785

Ala Ala Thr Gly Ala Cys Thr Ala Cys Ala Ala Ala Gly Ala Cys
1790 1795 1800

Gly Ala Thr Gly Ala Cys Gly Ala Cys Ala Ala Gly Thr Gly Ala 1805 1810 1815

<210> SEQ ID NO 21
<211> LENGTH: 605
<212> TYPE: PRT
<213> ORGANISM: Artificial Sequence
<220> FEATURE:
<223> OTHER INFORMATION: Synthetic Polypeptide

<400> SEQUENCE: 21

```
Met Gly Ser Arg Ile Val Ile Asn Arg Glu His Leu Met Ile Asp Arg
1               5                   10                  15

Pro Tyr Val Leu Leu Ala Val Leu Phe Val Met Phe Leu Ser Leu Ile
            20                  25                  30

Gly Leu Leu Ala Ile Ala Gly Ile Arg Leu His Arg Ala Ala Ile Tyr
        35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
            100                 105                 110

Tyr Asp Phe Arg Asp Leu Thr Trp Cys Ile Asn Pro Pro Glu Arg Ile
        115                 120                 125

Lys Leu Asp Tyr Asp Gln Tyr Cys Ala Asp Val Ala Ala Glu Glu Leu
    130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
            180                 185                 190

Gly Arg Gly Tyr Asn Val Ser Ser Ile Val Thr Met Thr Ser Gln Gly
        195                 200                 205

Met Tyr Gly Gly Thr Tyr Leu Val Glu Lys Pro Asn Leu Ser Ser Lys
    210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                245                 250                 255

Tyr Leu Glu Gln Pro Val Ser Asn Asp Leu Ser Asn Cys Met Val Ala
            260                 265                 270

Leu Gly Glu Leu Lys Leu Ala Ala Leu Cys His Gly Glu Asp Ser Ile
        275                 280                 285

Thr Ile Pro Tyr Gln Gly Ser Gly Lys Gly Val Ser Phe Gln Leu Val
    290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                325                 330                 335

Arg Gly Val Ile Ala Asp Asn Gln Ala Lys Trp Ala Val Pro Thr Thr
            340                 345                 350

Arg Thr Asp Asp Lys Leu Arg Met Glu Thr Cys Phe Gln Gln Ala Cys
```

```
        355                 360                 365

Lys Gly Lys Ile Gln Ala Leu Cys Glu Asn Pro Glu Trp Ala Pro Leu
    370                 375                 380

Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
                405                 410                 415

Ile Thr His Gly Ser Gly Met Asp Leu Tyr Lys Ser Asn His Asn Asn
            420                 425                 430

Val Tyr Trp Leu Thr Ile Pro Pro Met Lys Asn Leu Ala Leu Gly Val
        435                 440                 445

Ile Asn Thr Leu Glu Trp Ile Pro Arg Phe Lys Val Ser Pro Ala Leu
    450                 455                 460

Phe Asn Val Pro Ile Lys Glu Ala Gly Gly Asp Cys His Ala Pro Thr
465                 470                 475                 480

Tyr Leu Pro Ala Glu Val Asp Gly Asp Val Lys Leu Ser Ser Asn Leu
                485                 490                 495

Val Ile Leu Pro Gly Gln Asp Leu Gln Tyr Val Leu Ala Thr Tyr Asp
            500                 505                 510

Thr Ser Ala Val Glu His Ala Val Val Tyr Tyr Val Tyr Ser Pro Ser
        515                 520                 525

Arg Ser Phe Ser Tyr Phe Tyr Pro Phe Arg Leu Pro Ile Lys Gly Val
    530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
                565                 570                 575

Thr His Ser Gly Met Val Gly Met Gly Val Ser Cys Thr Val Thr Arg
            580                 585                 590

Glu Asp Gly Thr Asn Asp Tyr Lys Asp Asp Asp Asp Lys
        595                 600                 605


<210> SEQ ID NO 22
<211> LENGTH: 1785
<212> TYPE: PRT
<213> ORGANISM: Artificial Sequence
<220> FEATURE:
<223> OTHER INFORMATION: Synthetic Polypeptide

<400> SEQUENCE: 22

Ala Thr Gly Ala Ala Gly Ala Ala Gly Ala Thr Cys Ala Ala Cys Gly
1               5                   10                  15

Ala Gly Gly Gly Cys Cys Thr Gly Cys Thr Gly Gly Ala Cys Ala Gly
            20                  25                  30

Cys Ala Ala Gly Ala Thr Cys Cys Thr Gly Ala Gly Cys Gly Cys Cys
        35                  40                  45

Thr Thr Cys Ala Ala Cys Ala Cys Cys Gly Thr Gly Ala Thr Thr Gly
    50                  55                  60

Cys Cys Cys Thr Gly Cys Thr Gly Gly Gly Cys Thr Cys Thr Ala Thr
65                  70                  75                  80

Cys Gly Thr Gly Ala Thr Cys Ala Thr Cys Gly Thr Gly Ala Thr Gly
                85                  90                  95

Ala Ala Cys Ala Thr Cys Ala Thr Gly Ala Thr Cys Ala Thr Cys Cys
            100                 105                 110

Ala Gly Ala Ala Cys Thr Ala Cys Ala Cys Cys Cys Gly Gly Thr Cys
```

-continued

```
        115                 120                 125

Cys Ala Cys Cys Gly Ala Cys Ala Ala Cys Cys Ala Gly Gly Cys Cys
    130                 135                 140

Gly Thr Gly Ala Thr Thr Ala Ala Gly Gly Ala Thr Gly Cys Thr Cys
145                 150                 155                 160

Thr Gly Cys Ala Gly Gly Gly Ala Ala Thr Cys Cys Ala Gly Cys Ala
                165                 170                 175

Gly Cys Ala Gly Ala Thr Cys Ala Ala Ala Gly Gly Cys Cys Thr Gly
            180                 185                 190

Gly Cys Cys Gly Ala Cys Ala Ala Gly Ala Thr Cys Gly Gly Cys Ala
        195                 200                 205

Cys Ala Gly Ala Gly Ala Thr Cys Gly Gly Cys Cys Cys Thr Ala Ala
    210                 215                 220

Gly Gly Thr Gly Thr Cys Cys Cys Thr Gly Ala Thr Cys Gly Ala Cys
225                 230                 235                 240

Ala Cys Cys Ala Gly Cys Ala Gly Cys Ala Cys Cys Ala Thr Cys Ala
                245                 250                 255

Cys Ala Ala Thr Cys Cys Cys Cys Gly Cys Cys Ala Ala Thr Ala Thr
            260                 265                 270

Cys Gly Gly Ala Cys Thr Gly Cys Thr Gly Gly Gly Ala Ala Gly Cys
        275                 280                 285

Ala Ala Gly Ala Thr Cys Ala Gly Cys Cys Ala Gly Ala Gly Cys Ala
    290                 295                 300

Cys Cys Gly Cys Cys Ala Gly Cys Ala Thr Cys Ala Ala Cys Gly Ala
305                 310                 315                 320

Gly Ala Ala Cys Gly Thr Gly Ala Ala Cys Gly Ala Gly Ala Ala Gly
                325                 330                 335

Thr Gly Cys Ala Ala Gly Thr Thr Cys Ala Cys Cys Cys Thr Gly Cys
            340                 345                 350

Cys Thr Cys Cys Ala Cys Thr Gly Ala Ala Gly Ala Thr Cys Cys Ala
        355                 360                 365

Cys Gly Ala Gly Thr Gly Cys Ala Ala Cys Ala Thr Cys Ala Gly Cys
    370                 375                 380

Thr Gly Cys Cys Cys Cys Ala Ala Thr Cys Cys Thr Cys Thr Gly Cys
385                 390                 395                 400

Cys Ala Thr Thr Cys Ala Gly Ala Gly Ala Gly Thr Ala Cys Ala Gly
                405                 410                 415

Ala Cys Cys Cys Cys Ala Gly Ala Cys Ala Gly Ala Gly Gly Gly Cys
            420                 425                 430

Gly Thr Gly Thr Cys Cys Ala Ala Thr Cys Thr Cys Gly Thr Gly Gly
        435                 440                 445

Gly Cys Cys Thr Gly Cys Cys Thr Ala Ala Cys Ala Ala Cys Ala Thr
    450                 455                 460

Cys Thr Gly Cys Cys Thr Gly Cys Ala Gly Ala Ala Ala Ala Cys Cys
465                 470                 475                 480

Ala Gly Cys Ala Ala Cys Cys Ala Gly Ala Thr Cys Cys Thr Gly Ala
                485                 490                 495

Ala Gly Cys Cys Thr Ala Ala Gly Cys Thr Gly Ala Thr Cys Thr Cys
            500                 505                 510

Cys Thr Ala Cys Ala Cys Ala Cys Thr Gly Cys Cys Cys Gly Thr Cys
        515                 520                 525

Gly Thr Gly Gly Gly Cys Cys Ala Gly Ala Gly Cys Gly Gly Cys Ala
    530                 535                 540
```

```
Cys Cys Thr Gly Thr Ala Thr Thr Ala Cys Ala Gly Ala Thr Cys Cys
545                 550                 555                 560

Thr Cys Thr Gly Cys Thr Gly Gly Cys Cys Ala Thr Gly Gly Ala Cys
                565                 570                 575

Gly Ala Gly Gly Gly Cys Thr Ala Cys Thr Thr Thr Gly Cys Cys Thr
            580                 585                 590

Ala Cys Ala Gly Cys Cys Ala Cys Cys Thr Gly Gly Ala Ala Ala Gly
        595                 600                 605

Ala Ala Thr Cys Gly Gly Cys Ala Gly Cys Thr Gly Thr Ala Gly Cys
    610                 615                 620

Cys Gly Gly Gly Gly Ala Gly Thr Gly Thr Cys Cys Ala Ala Gly Cys
625                 630                 635                 640

Ala Gly Ala Gly Ala Ala Thr Cys Ala Thr Cys Gly Gly Cys Gly Thr
                645                 650                 655

Gly Gly Gly Cys Gly Ala Ala Gly Thr Gly Cys Thr Gly Gly Ala Thr
            660                 665                 670

Ala Gly Ala Gly Gly Cys Gly Ala Cys Gly Ala Ala Gly Thr Gly Cys
        675                 680                 685

Cys Cys Ala Gly Cys Cys Thr Gly Thr Thr Cys Ala Thr Gly Ala Cys
    690                 695                 700

Cys Ala Ala Thr Gly Thr Gly Thr Gly Gly Ala Cys Cys Cys Cys Thr
705                 710                 715                 720

Cys Cys Thr Ala Ala Thr Cys Cys Thr Ala Ala Cys Ala Cys Cys Gly
                725                 730                 735

Thr Gly Thr Ala Cys Cys Ala Cys Thr Gly Cys Ala Gly Cys Gly Cys
            740                 745                 750

Cys Gly Thr Gly Thr Ala Cys Ala Ala Cys Ala Ala Cys Gly Ala Gly
        755                 760                 765

Thr Thr Cys Thr Ala Cys Thr Ala Cys Gly Thr Gly Cys Thr Gly Thr
    770                 775                 780

Gly Cys Gly Cys Cys Gly Thr Gly Thr Cys Cys Ala Cys Ala Gly Thr
785                 790                 795                 800

Gly Gly Gly Cys Gly Ala Cys Cys Cys Thr Ala Thr Cys Cys Thr Gly
                805                 810                 815

Ala Ala Cys Ala Gly Cys Ala Cys Cys Thr Ala Thr Thr Gly Gly Ala
            820                 825                 830

Gly Cys Gly Gly Cys Ala Gly Cys Cys Thr Gly Ala Thr Gly Ala Thr
        835                 840                 845

Gly Ala Cys Cys Ala Gly Ala Cys Thr Gly Gly Cys Cys Gly Thr Gly
    850                 855                 860

Ala Ala Gly Cys Cys Cys Ala Ala Gly Ala Gly Cys Ala Ala Thr Gly
865                 870                 875                 880

Gly Cys Gly Gly Cys Gly Gly Ala Thr Ala Cys Ala Ala Cys Cys Ala
                885                 890                 895

Gly Cys Ala Thr Cys Ala Gly Cys Thr Gly Gly Cys Cys Cys Thr Gly
            900                 905                 910

Cys Gly Gly Thr Cys Cys Ala Thr Cys Gly Ala Gly Ala Ala Gly Gly
        915                 920                 925

Gly Cys Ala Gly Ala Thr Ala Cys Gly Ala Cys Ala Ala Ala Gly Thr
    930                 935                 940

Gly Ala Thr Gly Cys Cys Thr Thr Ala Cys Gly Gly Cys Cys Cys Cys
945                 950                 955                 960
```

```
Ala Gly Cys Gly Gly Cys Ala Thr Cys Ala Ala Gly Cys Ala Ala Gly
                965                 970                 975

Gly Cys Gly Ala Thr Ala Cys Cys Cys Thr Gly Thr Ala Cys Thr Thr
            980                 985                 990

Thr Cys Cys Cys Gly Cys Cys Gly  Thr Gly Gly Gly Ala  Thr Thr Thr
        995                 1000                 1005

Cys Thr  Cys Gly Thr Gly Cys  Gly Gly Ala Cys Cys  Gly Ala Gly
    1010                 1015                 1020

Thr Thr  Cys Ala Ala Gly Thr  Ala Cys Ala Ala Cys  Gly Ala Cys
    1025                 1030                 1035

Ala Gly  Cys Ala Ala Cys Thr  Gly Cys Cys Cys Cys  Ala Thr Cys
    1040                 1045                 1050

Ala Cys  Cys Ala Ala Gly Thr  Gly Cys Cys Ala Gly  Thr Ala Cys
    1055                 1060                 1065

Ala Gly  Cys Ala Ala Gly Cys  Cys Cys Gly Ala Gly  Ala Ala Cys
    1070                 1075                 1080

Thr Gly  Cys Ala Gly Ala Cys  Thr Gly Ala Gly Cys  Ala Thr Gly
    1085                 1090                 1095

Gly Gly  Cys Ala Thr Cys Ala  Gly Ala Cys Cys Cys  Ala Ala Cys
    1100                 1105                 1110

Ala Gly  Cys Cys Ala Cys Thr  Ala Cys Ala Thr Cys  Cys Thr Gly
    1115                 1120                 1125

Ala Gly  Ala Ala Gly Cys Gly  Gly Cys Cys Thr Gly  Cys Thr Gly
    1130                 1135                 1140

Ala Ala  Gly Thr Ala Cys Ala  Ala Cys Cys Thr Gly  Ala Gly Cys
    1145                 1150                 1155

Gly Ala  Cys Gly Gly Cys Gly  Ala Gly Ala Ala Cys  Cys Cys Cys
    1160                 1165                 1170

Ala Ala  Gly Gly Thr Gly Gly  Thr Gly Thr Thr Cys  Ala Thr Cys
    1175                 1180                 1185

Gly Ala  Gly Ala Thr Cys Ala  Gly Cys Gly Ala Cys  Cys Ala Gly
    1190                 1195                 1200

Cys Gly  Gly Cys Thr Gly Thr  Cys Thr Ala Thr Cys  Gly Gly Cys
    1205                 1210                 1215

Ala Gly  Cys Cys Cys Cys Thr  Cys Cys Ala Ala Gly  Ala Thr Cys
    1220                 1225                 1230

Thr Ala  Cys Gly Ala Cys Thr  Cys Thr Cys Thr Gly  Gly Gly Cys
    1235                 1240                 1245

Cys Ala  Gly Cys Cys Ala Gly  Thr Gly Thr Thr Cys  Thr Ala Cys
    1250                 1255                 1260

Cys Ala  Gly Gly Cys Cys Ala  Gly Cys Thr Thr Thr  Ala Gly Cys
    1265                 1270                 1275

Thr Gly  Gly Gly Ala Cys Ala  Cys Cys Ala Thr Gly  Ala Thr Cys
    1280                 1285                 1290

Ala Ala  Gly Thr Thr Cys Gly  Gly Cys Gly Ala Cys  Gly Thr Gly
    1295                 1300                 1305

Cys Thr  Gly Ala Cys Cys Gly  Thr Gly Ala Ala Thr  Cys Cys Cys
    1310                 1315                 1320

Cys Thr  Gly Gly Thr Gly Gly  Thr Cys Ala Ala Cys  Thr Gly Gly
    1325                 1330                 1335

Cys Gly  Gly Ala Ala Cys Ala  Ala Thr Ala Cys Cys  Gly Thr Gly
    1340                 1345                 1350

Ala Thr  Cys Ala Gly Cys Cys  Gly Gly Cys Cys Thr  Gly Gly Cys
```

```
    1355                1360                1365

Cys Ala  Gly Thr Cys Thr Cys  Ala Gly Thr Gly Cys  Cys Cys Cys
    1370                1375                1380

Ala Gly  Ala Thr Thr Cys Ala  Ala Thr Ala Cys Cys  Thr Gly Thr
    1385                1390                1395

Cys Cys  Thr Gly Cys Cys Ala  Thr Thr Thr Gly Cys  Gly Cys Cys
    1400                1405                1410

Gly Ala  Ala Gly Gly Cys Gly  Thr Gly Thr Ala Cys  Ala Ala Thr
    1415                1420                1425

Gly Ala  Cys Gly Cys Cys Thr  Thr Cys Cys Thr Gly  Ala Thr Cys
    1430                1435                1440

Gly Ala  Thr Cys Gly Gly Ala  Thr Cys Ala Ala Cys  Thr Gly Gly
    1445                1450                1455

Ala Thr  Cys Thr Cys Thr Gly  Cys Cys Gly Gly Cys  Gly Thr Gly
    1460                1465                1470

Thr Thr  Cys Cys Thr Gly Gly  Ala Cys Thr Cys Thr  Ala Ala Thr
    1475                1480                1485

Gly Cys  Cys Ala Cys Ala Gly  Cys Cys Gly Cys Cys  Ala Ala Thr
    1490                1495                1500

Cys Cys  Thr Gly Thr Gly Thr  Thr Cys Ala Cys Cys  Gly Thr Gly
    1505                1510                1515

Thr Thr  Cys Ala Ala Gly Gly  Ala Cys Ala Ala Thr  Gly Ala Gly
    1520                1525                1530

Ala Thr  Cys Cys Thr Gly Thr  Ala Thr Cys Gly Gly  Gly Cys Cys
    1535                1540                1545

Cys Ala  Gly Cys Thr Gly Gly  Cys Cys Thr Cys Cys  Gly Ala Gly
    1550                1555                1560

Gly Ala  Cys Ala Cys Ala Ala  Ala Thr Gly Cys Cys  Cys Ala Gly
    1565                1570                1575

Ala Ala  Ala Ala Cys Ala Ala  Thr Cys Ala Cys Cys  Ala Ala Cys
    1580                1585                1590

Thr Gly  Cys Thr Thr Thr Cys  Thr Gly Cys Thr Cys  Ala Ala Gly
    1595                1600                1605

Ala Ala  Cys Ala Ala Gly Ala  Thr Cys Thr Gly Gly  Thr Gly Cys
    1610                1615                1620

Ala Thr  Cys Ala Gly Cys Cys  Thr Gly Gly Thr Gly  Gly Ala Ala
    1625                1630                1635

Ala Thr  Cys Thr Ala Cys Gly  Ala Cys Ala Cys Cys  Gly Gly Cys
    1640                1645                1650

Gly Ala  Cys Ala Ala Cys Gly  Thr Gly Ala Thr Cys  Ala Gly Gly
    1655                1660                1665

Cys Cys  Cys Ala Ala Gly Cys  Thr Gly Thr Thr Cys  Gly Cys Cys
    1670                1675                1680

Gly Thr  Gly Ala Ala Gly Ala  Thr Cys Cys Cys Thr  Gly Ala Gly
    1685                1690                1695

Cys Ala  Gly Thr Gly Thr Ala  Cys Ala Gly Gly Cys  Gly Gly Cys
    1700                1705                1710

Gly Gly  Ala Gly Gly Ala Thr  Cys Thr Gly Gly Cys  Gly Gly Ala
    1715                1720                1725

Gly Gly  Thr Gly Gly Ala Ala  Gly Cys Gly Gly Ala  Gly Gly Cys
    1730                1735                1740

Gly Gly  Thr Gly Gly Ala Thr  Cys Thr Gly Cys Thr  Ala Gly Cys
    1745                1750                1755
```

```
Gly Ala  Thr Thr Ala Cys Ala  Ala Gly Gly Ala Thr  Gly Ala Cys
    1760                 1765                 1770

Gly Ala  Cys Gly Ala Thr Ala  Ala Gly Thr Gly Ala
    1775                 1780                 1785


<210> SEQ ID NO 23
<211> LENGTH: 594
<212> TYPE: PRT
<213> ORGANISM: Artificial Sequence
<220> FEATURE:
<223> OTHER INFORMATION: Synthetic Polypeptide

<400> SEQUENCE: 23

Met Lys Lys Ile Asn Glu Gly Leu Leu Asp Ser Lys Ile Leu Ser Ala
1               5                   10                  15

Phe Asn Thr Val Ile Ala Leu Leu Gly Ser Ile Val Ile Ile Val Met
            20                  25                  30

Asn Ile Met Ile Ile Gln Asn Tyr Thr Arg Ser Thr Asp Asn Gln Ala
        35                  40                  45

Val Ile Lys Asp Ala Leu Gln Gly Ile Gln Gln Gln Ile Lys Gly Leu
    50                  55                  60

Ala Asp Lys Ile Gly Thr Glu Ile Gly Pro Lys Val Ser Leu Ile Asp
65                  70                  75                  80

Thr Ser Ser Thr Ile Thr Ile Pro Ala Asn Ile Gly Leu Leu Gly Ser
                85                  90                  95

Lys Ile Ser Gln Ser Thr Ala Ser Ile Asn Glu Asn Val Asn Glu Lys
            100                 105                 110

Cys Lys Phe Thr Leu Pro Pro Leu Lys Ile His Glu Cys Asn Ile Ser
        115                 120                 125

Cys Pro Asn Pro Leu Pro Phe Arg Glu Tyr Arg Pro Gln Thr Glu Gly
    130                 135                 140

Val Ser Asn Leu Val Gly Leu Pro Asn Asn Ile Cys Leu Gln Lys Thr
145                 150                 155                 160

Ser Asn Gln Ile Leu Lys Pro Lys Leu Ile Ser Tyr Thr Leu Pro Val
                165                 170                 175

Val Gly Gln Ser Gly Thr Cys Ile Thr Asp Pro Leu Leu Ala Met Asp
            180                 185                 190

Glu Gly Tyr Phe Ala Tyr Ser His Leu Glu Arg Ile Gly Ser Cys Ser
        195                 200                 205

Arg Gly Val Ser Lys Gln Arg Ile Ile Gly Val Gly Glu Val Leu Asp
    210                 215                 220

Arg Gly Asp Glu Val Pro Ser Leu Phe Met Thr Asn Val Trp Thr Pro
225                 230                 235                 240

Pro Asn Pro Asn Thr Val Tyr His Cys Ser Ala Val Tyr Asn Asn Glu
                245                 250                 255

Phe Tyr Tyr Val Leu Cys Ala Val Ser Thr Val Gly Asp Pro Ile Leu
            260                 265                 270

Asn Ser Thr Tyr Trp Ser Gly Ser Leu Met Met Thr Arg Leu Ala Val
        275                 280                 285

Lys Pro Lys Ser Asn Gly Gly Gly Tyr Asn Gln His Gln Leu Ala Leu
    290                 295                 300

Arg Ser Ile Glu Lys Gly Arg Tyr Asp Lys Val Met Pro Tyr Gly Pro
305                 310                 315                 320

Ser Gly Ile Lys Gln Gly Asp Thr Leu Tyr Phe Pro Ala Val Gly Phe
                325                 330                 335
```

```
Leu Val Arg Thr Glu Phe Lys Tyr Asn Asp Ser Asn Cys Pro Ile Thr
            340                 345                 350

Lys Cys Gln Tyr Ser Lys Pro Glu Asn Cys Arg Leu Ser Met Gly Ile
        355                 360                 365

Arg Pro Asn Ser His Tyr Ile Leu Arg Ser Gly Leu Leu Lys Tyr Asn
    370                 375                 380

Leu Ser Asp Gly Glu Asn Pro Lys Val Val Phe Ile Glu Ile Ser Asp
385                 390                 395                 400

Gln Arg Leu Ser Ile Gly Ser Pro Ser Lys Ile Tyr Asp Ser Leu Gly
                405                 410                 415

Gln Pro Val Phe Tyr Gln Ala Ser Phe Ser Trp Asp Thr Met Ile Lys
            420                 425                 430

Phe Gly Asp Val Leu Thr Val Asn Pro Leu Val Val Asn Trp Arg Asn
        435                 440                 445

Asn Thr Val Ile Ser Arg Pro Gly Gln Ser Gln Cys Pro Arg Phe Asn
    450                 455                 460

Thr Cys Pro Ala Ile Cys Ala Glu Gly Val Tyr Asn Asp Ala Phe Leu
465                 470                 475                 480

Ile Asp Arg Ile Asn Trp Ile Ser Ala Gly Val Phe Leu Asp Ser Asn
                485                 490                 495

Ala Thr Ala Ala Asn Pro Val Phe Thr Val Phe Lys Asp Asn Glu Ile
            500                 505                 510

Leu Tyr Arg Ala Gln Leu Ala Ser Glu Asp Thr Asn Ala Gln Lys Thr
        515                 520                 525

Ile Thr Asn Cys Phe Leu Leu Lys Asn Lys Ile Trp Cys Ile Ser Leu
    530                 535                 540

Val Glu Ile Tyr Asp Thr Gly Asp Asn Val Ile Arg Pro Lys Leu Phe
545                 550                 555                 560

Ala Val Lys Ile Pro Glu Gln Cys Thr Gly Gly Gly Gly Ser Gly Gly
                565                 570                 575

Gly Gly Ser Gly Gly Gly Gly Ser Ala Ser Asp Tyr Lys Asp Asp Asp
            580                 585                 590

Asp Lys


<210> SEQ ID NO 24
<211> LENGTH: 609
<212> TYPE: PRT
<213> ORGANISM: Artificial Sequence
<220> FEATURE:
<223> OTHER INFORMATION: Synthetic Polypeptide

<400> SEQUENCE: 24

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95
```

-continued

```
Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Ala Thr Asn Phe Ser Leu Leu
305                 310                 315                 320

Lys Gln Ala Gly Asp Val Glu Glu Asn Pro Gly Pro Met Glu Thr Leu
                325                 330                 335

Leu Gly Leu Leu Ile Leu Trp Leu Gln Leu Gln Trp Val Ser Ser Lys
            340                 345                 350

Gln Glu Val Thr Gln Ile Pro Ala Ala Leu Ser Val Pro Glu Gly Glu
        355                 360                 365

Asn Leu Val Leu Asn Cys Ser Phe Thr Asp Ser Ala Ile Tyr Asn Leu
    370                 375                 380

Gln Trp Phe Arg Gln Asp Pro Gly Lys Gly Leu Thr Ser Leu Leu Leu
385                 390                 395                 400

Ile Gln Ser Ser Gln Arg Glu Gln Thr Ser Gly Arg Leu Asn Ala Ser
                405                 410                 415

Leu Asp Lys Ser Ser Gly Ser Ser Thr Leu Tyr Ile Ala Ala Ser Gln
            420                 425                 430

Pro Gly Asp Ser Ala Thr Tyr Leu Cys Ala Val Arg Pro Thr Ser Gly
        435                 440                 445

Gly Ser Tyr Ile Pro Thr Phe Gly Arg Gly Thr Ser Leu Ile Val His
    450                 455                 460

Pro Tyr Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
```

```
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser Ala Ala
        595                 600                 605

Ala


<210> SEQ ID NO 25
<211> LENGTH: 609
<212> TYPE: PRT
<213> ORGANISM: Artificial Sequence
<220> FEATURE:
<223> OTHER INFORMATION: Synthetic Polypeptide

<400> SEQUENCE: 25

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gln Thr Thr Asp Gln Gly Glu Val Pro
65                  70                  75                  80

Asn Gly Tyr Asn Val Ser Arg Ser Thr Ile Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Leu Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270
```

Gly Val Leu Ser Ala Thr Ile Leu Tyr Glu Ile Leu Leu Gly Lys Ala
275 280 285

Thr Leu Tyr Ala Val Leu Val Ser Ala Leu Val Leu Met Ala Met Val
290 295 300

Lys Arg Lys Asp Ser Arg Gly Gly Ser Ala Thr Asn Phe Ser Leu Leu
305 310 315 320

Lys Gln Ala Gly Asp Val Glu Glu Asn Pro Gly Pro Met Glu Thr Leu
325 330 335

Leu Gly Leu Leu Ile Leu Trp Leu Gln Leu Gln Trp Val Ser Ser Lys
340 345 350

Gln Glu Val Thr Gln Ile Pro Ala Ala Leu Ser Val Pro Glu Gly Glu
355 360 365

Asn Leu Val Leu Asn Cys Ser Phe Thr Asp Ser Ala Ile Tyr Asn Leu
370 375 380

Gln Trp Phe Arg Gln Asp Pro Gly Lys Gly Leu Thr Ser Leu Leu Leu
385 390 395 400

Ile Gln Ser Ser Gln Arg Glu Gln Thr Ser Gly Arg Leu Asn Ala Ser
405 410 415

Leu Asp Lys Ser Ser Gly Ser Ser Thr Leu Tyr Ile Ala Ala Ser Gln
420 425 430

Pro Gly Asp Ser Ala Thr Tyr Leu Cys Ala Val Arg Pro Met Ile Gly
435 440 445

Gly Thr Tyr Ile Pro Thr Phe Gly Arg Gly Thr Ser Leu Ile Val His
450 455 460

Pro Tyr Ile Gln Asn Pro Asp Pro Ala Val Tyr Gln Leu Arg Asp Ser
465 470 475 480

Lys Ser Ser Asp Lys Ser Val Cys Leu Phe Thr Asp Phe Asp Ser Gln
485 490 495

Thr Asn Val Ser Gln Ser Lys Asp Ser Asp Val Tyr Ile Thr Asp Lys
500 505 510

Thr Val Leu Asp Met Arg Ser Met Asp Phe Lys Ser Asn Ser Ala Val
515 520 525

Ala Trp Ser Asn Lys Ser Asp Phe Ala Cys Ala Asn Ala Phe Asn Asn
530 535 540

Ser Ile Ile Pro Glu Asp Thr Phe Phe Pro Ser Pro Glu Ser Ser Cys
545 550 555 560

Asp Val Lys Leu Val Glu Lys Ser Phe Glu Thr Asp Thr Asn Leu Asn
565 570 575

Phe Gln Asn Leu Ser Val Ile Gly Phe Arg Ile Leu Leu Leu Lys Val
580 585 590

Ala Gly Phe Asn Leu Leu Met Thr Leu Arg Leu Trp Ser Ser Ala Ala
595 600 605

Ala

<210> SEQ ID NO 26
<211> LENGTH: 609
<212> TYPE: PRT
<213> ORGANISM: Artificial Sequence
<220> FEATURE:
<223> OTHER INFORMATION: Synthetic Polypeptide

<400> SEQUENCE: 26

Met Ser Ile Gly Leu Leu Cys Cys Ala Ala Leu Ser Leu Leu Trp Ala
1 5 10 15

-continued

Gly Pro Val Asn Ala Gly Val Thr Gln Thr Pro Lys Phe Gln Val Leu
20 25 30

Lys Thr Gly Gln Ser Met Thr Leu Gln Cys Ala Gln Asp Met Asn His
35 40 45

Glu Tyr Met Ser Trp Tyr Arg Gln Asp Pro Gly Met Gly Leu Arg Leu
50 55 60

Ile His Tyr Ser Val Gly Ala Gly Thr Thr Asp Arg Gly Glu Val Pro
65 70 75 80

Asn Gly Tyr Asn Val Ser Arg Ser Thr Ile Glu Asp Phe Pro Leu Arg
85 90 95

Leu Leu Ser Ala Ala Pro Ser Gln Thr Ser Val Tyr Phe Cys Ala Ser
100 105 110

Ser Tyr Val Gly Asp Thr Gly Glu Leu Phe Phe Gly Glu Gly Ser Arg
115 120 125

Leu Thr Val Leu Glu Asp Leu Lys Asn Val Phe Pro Pro Glu Val Ala
130 135 140

Val Phe Glu Pro Ser Glu Ala Glu Ile Ser His Thr Gln Lys Ala Thr
145 150 155 160

Leu Val Cys Leu Ala Thr Gly Phe Tyr Pro Asp His Val Glu Leu Ser
165 170 175

Trp Trp Val Asn Gly Lys Glu Val His Ser Gly Val Ser Thr Asp Pro
180 185 190

Gln Pro Leu Lys Glu Gln Pro Ala Leu Asn Asp Ser Arg Tyr Cys Leu
195 200 205

Ser Ser Arg Leu Arg Val Ser Ala Thr Phe Trp Gln Asn Pro Arg Asn
210 215 220

His Phe Arg Cys Gln Val Gln Phe Tyr Gly Leu Ser Glu Asn Asp Glu
225 230 235 240

Trp Thr Gln Asp Arg Ala Lys Pro Val Thr Gln Ile Val Ser Ala Glu
245 250 255

Ala Trp Gly Arg Ala Asp Cys Gly Phe Thr Ser Glu Ser Tyr Gln Gln
260 265 270

Gly Val Leu Ser Ala Thr Ile Leu Tyr Glu Ile Leu Leu Gly Lys Ala
275 280 285

Thr Leu Tyr Ala Val Leu Val Ser Ala Leu Val Leu Met Ala Met Val
290 295 300

Lys Arg Lys Asp Ser Arg Gly Gly Ser Ala Thr Asn Phe Ser Leu Leu
305 310 315 320

Lys Gln Ala Gly Asp Val Glu Glu Asn Pro Gly Pro Met Glu Thr Leu
325 330 335

Leu Gly Leu Leu Ile Leu Trp Leu Gln Leu Gln Trp Val Ser Ser Lys
340 345 350

Gln Glu Val Thr Gln Ile Pro Ala Ala Leu Ser Val Pro Glu Gly Glu
355 360 365

Asn Leu Val Leu Asn Cys Ser Phe Thr Asp Ser Ala Ile Tyr Asn Leu
370 375 380

Gln Trp Phe Arg Gln Asp Pro Gly Lys Gly Leu Thr Ser Leu Leu Leu
385 390 395 400

Ile Gln Ser Ser Gln Arg Glu Gln Thr Ser Gly Arg Leu Asn Ala Ser
405 410 415

Leu Asp Lys Ser Ser Gly Ser Ser Thr Leu Tyr Ile Ala Ala Ser Gln
420 425 430

Pro Gly Asp Ser Ala Thr Tyr Leu Cys Ala Val Arg Pro Leu Leu Asp

```
        435                 440                 445

Gly Thr Tyr Ile Pro Thr Phe Gly Arg Gly Thr Ser Leu Ile Val His
    450                 455                 460

Pro Tyr Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser Ala Ala
        595                 600                 605

Ala


<210> SEQ ID NO 27
<211> LENGTH: 609
<212> TYPE: PRT
<213> ORGANISM: Artificial Sequence
<220> FEATURE:
<223> OTHER INFORMATION: Synthetic Polypeptide

<400> SEQUENCE: 27

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Ala Ile Gln Thr Thr Asp Gln Gly Glu Val Pro
65                  70                  75                  80

Asn Gly Tyr Asn Val Ser Arg Ser Thr Ile Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Leu Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190
```

```
Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly Gly Ser Ala Thr Asn Phe Ser Leu Leu
305                 310                 315                 320

Lys Gln Ala Gly Asp Val Glu Glu Asn Pro Gly Pro Met Glu Thr Leu
                325                 330                 335

Leu Gly Leu Leu Ile Leu Trp Leu Gln Leu Gln Trp Val Ser Ser Lys
            340                 345                 350

Gln Glu Val Thr Gln Ile Pro Ala Ala Leu Ser Val Pro Glu Gly Glu
        355                 360                 365

Asn Leu Val Leu Asn Cys Ser Phe Thr Asp Ser Ala Ile Tyr Asn Leu
    370                 375                 380

Gln Trp Phe Arg Gln Asp Pro Gly Lys Gly Leu Thr Ser Leu Leu Leu
385                 390                 395                 400

Ile Thr Pro Trp Gln Arg Glu Gln Thr Ser Gly Arg Leu Asn Ala Ser
                405                 410                 415

Leu Asp Lys Ser Ser Gly Ser Ser Thr Leu Tyr Ile Ala Ala Ser Gln
            420                 425                 430

Pro Gly Asp Ser Ala Thr Tyr Leu Cys Ala Val Arg Pro Leu Leu Asp
        435                 440                 445

Gly Thr Tyr Ile Pro Thr Phe Gly Arg Gly Thr Ser Leu Ile Val His
    450                 455                 460

Pro Tyr Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser Ala Ala
        595                 600                 605
```

Ala

<210> SEQ ID NO 28
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 28

```
Val Val Val Ile Ser Ala Ile Leu Ala Leu Val Val Leu Thr Ile Ile
1               5                   10                  15

Ser Leu Ile Ile Leu Ile Met Leu Trp Gln Lys Lys Pro Arg
            20                  25                  30
```

<210> SEQ ID NO 29
<211> LENGTH: 60
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (7)..(60)
<223> OTHER INFORMATION: may be absent

<400> SEQUENCE: 29

```
Gly Ala Pro Gly Ala Ser Gly Ala Pro Gly Ala Ser Gly Ala Pro Gly
1               5                   10                  15

Ala Ser Gly Ala Pro Gly Ala Ser Gly Ala Pro Gly Ala Ser Gly Ala
            20                  25                  30

Pro Gly Ala Ser Gly Ala Pro Gly Ala Ser Gly Ala Pro Gly Ala Ser
        35                  40                  45

Gly Ala Pro Gly Ala Ser Gly Ala Pro Gly Ala Ser
    50                  55                  60
```

<210> SEQ ID NO 30
<211> LENGTH: 50
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(50)
<223> OTHER INFORMATION: may be absent

<400> SEQUENCE: 30

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50
```

<210> SEQ ID NO 31
<211> LENGTH: 603
<212> TYPE: PRT
<213> ORGANISM: Artificial Sequence
<220> FEATURE:
<223> OTHER INFORMATION: Synthetic Polypeptide

<400> SEQUENCE: 31

```
Met Ser Ile Gly Leu Leu Cys Cys Ala Ala Leu Ser Leu Leu Trp Ala
1               5                   10                  15

Gly Pro Val Asn Ala Asp Ala Gly Val Thr Gln Ser Pro Thr His Leu
            20                  25                  30

Ile Lys Thr Arg Gly Gln Gln Val Thr Leu Arg Cys Ser Pro Lys Gln
        35                  40                  45

Gly His Asp Thr Val Ser Trp Tyr Gln Gln Ala Leu Gly Gln Gly Pro
    50                  55                  60

Gln Phe Ile Phe Gln Tyr Tyr Glu Glu Glu Glu Arg Gln Arg Gly Asn
65                  70                  75                  80

Phe Pro Asp Arg Phe Ser Gly His Gln Phe Pro Asn Tyr Ser Ser Glu
                85                  90                  95

Leu Asn Val Asn Ala Leu Leu Leu Gly Asp Ser Ala Leu Tyr Leu Cys
            100                 105                 110

Ala Ser Ser Asp Thr Val Ser Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asp Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly Gly Ser Ala Thr Asn Phe Ser Leu
305                 310                 315                 320

Leu Lys Gln Ala Gly Asp Val Glu Glu Asn Pro Gly Pro Met Glu Thr
                325                 330                 335

Leu Leu Gly Leu Leu Ile Leu Trp Leu Gln Leu Gln Trp Val Ser Ser
            340                 345                 350

Lys Glu Val Glu Gln Asn Ser Gly Pro Leu Ser Val Pro Glu Gly Ala
        355                 360                 365

Ile Ala Ser Leu Asn Cys Thr Tyr Ser Asp Arg Gly Ser Gln Ser Phe
    370                 375                 380

Phe Trp Tyr Arg Gln Tyr Ser Gly Lys Ser Pro Glu Leu Ile Met Phe
385                 390                 395                 400

Ile Tyr Ser Asn Gly Asp Lys Glu Asp Gly Arg Phe Thr Ala Gln Leu
                405                 410                 415
```

```
Asn Lys Ala Ser Gln Tyr Ile Ser Leu Leu Ile Arg Asp Ser Lys Leu
            420                 425                 430

Ser Asp Ser Ala Thr Tyr Leu Cys Ala Val Arg Thr Asn Ser Gly Tyr
        435                 440                 445

Ala Leu Asn Phe Gly Lys Gly Thr Ser Leu Leu Val Thr Pro His Ile
    450                 455                 460

Gln Lys Pro Asp Pro Ala Val Tyr Gln Leu Arg Asp Ser Lys Ser Ser
465                 470                 475                 480

Asp Lys Ser Val Cys Leu Phe Thr Asp Phe Asp Ser Gln Thr Asn Val
                485                 490                 495

Ser Gln Ser Lys Asp Ser Asp Val Tyr Ile Thr Asp Lys Thr Val Leu
            500                 505                 510

Asp Met Arg Ser Met Asp Phe Lys Ser Asn Ser Ala Val Ala Trp Ser
        515                 520                 525

Asn Lys Ser Asp Phe Ala Cys Ala Asn Ala Phe Asn Asn Ser Ile Ile
    530                 535                 540

Pro Glu Asp Thr Phe Phe Pro Ser Pro Glu Ser Ser Cys Asp Val Lys
545                 550                 555                 560

Leu Val Glu Lys Ser Phe Glu Thr Asp Thr Asn Leu Asn Phe Gln Asn
                565                 570                 575

Leu Ser Val Ile Gly Phe Arg Ile Leu Leu Leu Lys Val Ala Gly Phe
            580                 585                 590

Asn Leu Leu Met Thr Leu Arg Leu Trp Ser Ser
        595                 600
```

<210> SEQ ID NO 32
<211> LENGTH: 1812
<212> TYPE: DNA
<213> ORGANISM: Artificial Sequence
<220> FEATURE:
<223> OTHER INFORMATION: Synthetic Polynucleotide

<400> SEQUENCE: 32

```
atgtctatcg ggctgctgtg ttgcgccgct ctgtccctgc tgtgggccgg acctgtcaat      60

gctgatgctg gcgtaacgca gagcccgaca catctgataa aaacaagagg ccaacaagtt     120

actctgaggt gcagtccaaa gcaagggcac gatactgtgt cttggtacca acaggctctt     180

gggcaagggc cacaattcat ctttcaatac tacgaggaag aagagcgcca acgaggaaac     240

tttcctgatc gcttcagcgg tcaccaattt cctaattaca gttccgaatt gaatgtaaat     300

gctctcctgc tcggcgatag cgctctgtac ctttgtgcct cctccgacac cgtaagctat     360

gaacaatact ttggtcctgg cactcgcctc accgtaaccg aagatctgaa gaacgttttt     420

ccgccagagg tcgccgtttt tgaaccaagc gaagcggaaa tcagtcacac acagaaggca     480

acactcgttt gtctggccac tggcttctac cccgatcacg tcgaactttc atggtgggtc     540

aatggaaagg aagttcacag cggtgtaagt actgatccac agcctctcaa agagcagccc     600

gccttgaatg acagcagata ttgtttgagt tcacggttga gagtaagcgc taccttctgg     660

caagatcctc gcaatcactt ccgatgtcag gtgcagtttt atggactgtc agaaaatgat     720

gaatggacac aagatagggc taaacccgtg acccaaatcg tgagcgctga ggcatggggt     780

cgagcagact gcggcttcac aagtgaatca taccagcagg gggtgctgag cgccactatc     840

ctgtacgaga ttctgctggg aaaggctacc ctgtatgcag tgctggtctc cgccctggtg     900

ctgatggcta tggtcaagcg aaaagacagc cggggcgggt ccgcaacaaa cttttccctg     960

ctgaaacagg ccggcgatgt ggaggaaaat cctgggccaa tggagactct gctgggactg    1020
```

```
ctgatcctgt ggctgcagct gcagtgggtg tcaagcaaag aagtagaaca aaactcaggc   1080

cccctgtccg taccagaggg agctatagcg tctctcaatt gtacgtacag cgaccggggc   1140

tcccaatcat tcttctggta tcggcagtac agcgggaaaa gtccggaatt gattatgttc   1200

atatattcta acggcgacaa agaggacggg cgatttacgg cacaactgaa caaagcgagc   1260

caatacatca gtcttcttat tcgagatagc aaattgtctg actccgctac atacctctgt   1320

gcagtccgga ctaactccgg ttacgccttg aactttggga aagggacgtc attgttggtc   1380

acgccgcaca tacagaagcc cgatcctgca gtttaccaac tccgggactc aaagtcttcc   1440

gataagagtg tctgtctttt caccgacttc gatagtcaaa cgaatgttag ccagtctaag   1500

gacagcgatg tttatatcac cgacaaaacc gtcctcgaca tgaggtctat ggacttcaag   1560

agcaacagcg cggtagcgtg gtcaaataag agcgactttg cttgcgcgaa cgctttcaat   1620

aattcaatca tacccgagga tactttcttc ccaagtccgg aatctagttg tgacgtgaag   1680

ctggtcgaga aaagtttcga aacagatact aacctgaatt ttcagaacct gtcagtgatc   1740

ggcttccgga ttctgctgct gaaggtcgcc gggttcaatc tgctgatgac cctgagactg   1800

tggtcaagct ga                                                         1812


<210> SEQ ID NO 33
<211> LENGTH: 609
<212> TYPE: PRT
<213> ORGANISM: Artificial Sequence
<220> FEATURE:
<223> OTHER INFORMATION: Synthetic Polypeptide

<400> SEQUENCE: 33

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Arg Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Glu Ser Val Ser Thr Leu
                85                  90                  95

Thr Ile Gln Arg Thr Gln Gln Glu Asp Ser Ala Val Tyr Leu Cys Ala
            100                 105                 110

Ser Ser Gln Thr Gln Leu Trp Glu Thr Gln Tyr Phe Gly Pro Gly Thr
        115                 120                 125

Arg Leu Leu Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
```

```
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly Gly Ser Ala Thr Asn Phe Ser Leu
305                 310                 315                 320

Leu Lys Gln Ala Gly Asp Val Glu Glu Asn Pro Gly Pro Met Glu Lys
                325                 330                 335

Asn Pro Leu Ala Ala Pro Leu Leu Ile Leu Trp Phe His Leu Asp Cys
            340                 345                 350

Val Ser Ser Ile Leu Asn Val Glu Gln Ser Pro Gln Ser Leu His Val
        355                 360                 365

Gln Glu Gly Asp Ser Thr Asn Phe Thr Cys Ser Phe Pro Ser Ser Asn
    370                 375                 380

Phe Tyr Ala Leu His Trp Tyr Arg Trp Glu Thr Ala Lys Ser Pro Glu
385                 390                 395                 400

Ala Leu Phe Val Met Thr Leu Asn Gly Asp Glu Lys Lys Lys Gly Arg
                405                 410                 415

Ile Ser Ala Thr Leu Asn Thr Lys Glu Gly Tyr Ser Tyr Leu Tyr Ile
            420                 425                 430

Lys Gly Ser Gln Pro Glu Asp Ser Ala Thr Tyr Leu Cys Ala Phe Ile
        435                 440                 445

Thr Gly Asn Gln Phe Tyr Phe Gly Thr Gly Thr Ser Leu Thr Val Ile
    450                 455                 460

Pro Asn Ile Gln Asn Pro Asp Pro Ala Val Tyr Gln Leu Arg Asp Ser
465                 470                 475                 480

Lys Ser Ser Asp Lys Ser Val Cys Leu Phe Thr Asp Phe Asp Ser Gln
                485                 490                 495

Thr Asn Val Ser Gln Ser Lys Asp Ser Asp Val Tyr Ile Thr Asp Lys
            500                 505                 510

Thr Val Leu Asp Met Arg Ser Met Asp Phe Lys Ser Asn Ser Ala Val
        515                 520                 525

Ala Trp Ser Asn Lys Ser Asp Phe Ala Cys Ala Asn Ala Phe Asn Asn
    530                 535                 540

Ser Ile Ile Pro Glu Asp Thr Phe Phe Pro Ser Pro Glu Ser Ser Cys
545                 550                 555                 560

Asp Val Lys Leu Val Glu Lys Ser Phe Glu Thr Asp Thr Asn Leu Asn
                565                 570                 575

Phe Gln Asn Leu Ser Val Ile Gly Phe Arg Ile Leu Leu Leu Lys Val
            580                 585                 590

Ala Gly Phe Asn Leu Leu Met Thr Leu Arg Leu Trp Ser Ser Ala Ala
        595                 600                 605

Ala
```

<210> SEQ ID NO 34
<211> LENGTH: 1830

<212> TYPE: DNA
<213> ORGANISM: Artificial Sequence
<220> FEATURE:
<223> OTHER INFORMATION: Synthetic Polynucleotide

<400> SEQUENCE: 34
atgggcacac ggttgctgtt ttgggttgct ttctgcctgc tcggcgcaga tcacacggga 60
gcgggggtta gtcagtcccc tagcaataaa gtgacggaaa aagggaaaga tgtcgagctg 120
aggtgtgatc caatttctgg acacactgcc ctctactggt atagacaacg ccttggtcag 180
gggctggagt tccttatcta tttccagggc aactccgcgc ccgacaaaag tggtctcccg 240
agcgaccggt tttcagcgga gcgcacgggt gaaagtgtta gcacactgac aatccaacgg 300
acgcagcagg aggatagtgc tgtttatctg tgtgcctcta gtcagactca actttgggaa 360
actcaatact tcggccctgg tacgcgcctg ctcgttcttg aagacctgaa gaatgtcttc 420
ccccctgagg tggccgtctt tgaaccttca gaggctgaaa ttagccacac tcagaaagct 480
accctggtgt gtctggcaac tggcttctat ccagatcacg tggagctgag ctggtgggtc 540
aacgggaagg aagtgcattc cggagtctct acagacccac agcccctgaa agagcagccc 600
gccctgaatg attcccggta ttgcctgtct agtcggctga gagtgtctgc taccttttgg 660
cagaacccta ggaatcattt ccgctgtcag gtgcagtttt acggcctgtc tgagaatgac 720
gaatggaccc aggatcgagc taagcctgtg acacagatcg tcagtgcaga ggcttgggga 780
cgagcagact gcggcttcac aagtgaatca taccagcagg gggtgctgag cgccactatc 840
ctgtacgaga ttctgctggg aaaggctacc ctgtatgcag tgctggtctc cgccctggtg 900
ctgatggcta tggtcaagcg aaaagacagc cggggcgggt ccgcaacaaa cttttccctg 960
ctgaaacagg ccggcgatgt ggaggaaaat cctgggccaa tggaaaagaa tccattggct 1020
gcacccttgc ttatactctg gtttcacttg gactgcgtat cctcaatttt gaatgttgaa 1080
caatcacccc agagtctcca cgtccaagaa ggggactcaa caaactttac ctgtagtttc 1140
ccctcaagta acttctacgc tctccactgg tatcggtggg agactgccaa gagccccgaa 1200
gctctcttcg taatgaccct taatggagac gaaaaaaaga aggggagaat aagtgccact 1260
ctgaatacca aagagggcta ttcctatctc tacataaaag gaagtcaacc tgaggattcc 1320
gccacttacc tgtgcgcgtt catcactgga aaccagttct atttcgggac cggaacatct 1380
ctgactgtaa tcccaaatat tcagaacccc gatcctgccg tctatcagct gagggacagc 1440
aagagctccg ataaatccgt gtgtctgttc acagactttg attctcagac taatgtgagc 1500
cagtccaagg acagtgatgt gtacatcacc gacaaaacag tcctggatat gcgcagcatg 1560
gacttcaagt ctaacagtgc agtggcctgg agtaacaagt cagacttcgc ttgcgcaaac 1620
gcctttaaca attcaatcat tcccgaggat accttctttc caagccccga atctagttgt 1680
gacgtgaagc tggtcgagaa aagtttcgaa acagatacta acctgaattt tcagaacctg 1740
tcagtgatcg gcttccggat tctgctgctg aaggtcgccg ggttcaatct gctgatgacc 1800
ctgagactgt ggtcaagcgc ggccgcctga 1830

<210> SEQ ID NO 35
<211> LENGTH: 474
<212> TYPE: PRT
<213> ORGANISM: Artificial Sequence
<220> FEATURE:
<223> OTHER INFORMATION: Synthetic Polypeptide

<400> SEQUENCE: 35

```
Met Ser Arg Ser Val Ala Leu Ala Val Leu Ala Leu Leu Ser Leu Ser
1               5                   10                  15

Gly Leu Glu Ala Ser Leu Tyr Asn Thr Val Ala Thr Leu Gly Gly Gly
            20                  25                  30

Ala Ser Gly Gly Gly Gly Ser Gly Gly Gly Gly Ser Ile Gln Arg Thr
        35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
    130                 135                 140

Gly Gly Gly Ser Gly Gly Gly Gly Ser Gly Gly Gly Gly Ser Gly Gly
145                 150                 155                 160

Gly Gly Ser His Ser Met Arg Tyr Phe Phe Thr Ser Val Ser Arg Pro
                165                 170                 175

Gly Arg Gly Glu Pro Arg Phe Ile Ala Val Gly Tyr Val Asp Asp Thr
            180                 185                 190

Gln Phe Val Arg Phe Asp Ser Asp Ala Ala Ser Gln Arg Met Glu Pro
        195                 200                 205

Arg Ala Pro Trp Ile Glu Gln Glu Gly Pro Glu Tyr Trp Asp Gly Glu
    210                 215                 220

Thr Arg Lys Val Lys Ala His Ser Gln Thr His Arg Val Asp Leu Gly
225                 230                 235                 240

Thr Leu Arg Gly Ala Tyr Asn Gln Ser Glu Ala Gly Ser His Thr Val
                245                 250                 255

Gln Arg Met Tyr Gly Cys Asp Val Gly Ser Asp Trp Arg Phe Leu Arg
            260                 265                 270

Gly Tyr His Gln Tyr Ala Tyr Asp Gly Lys Asp Tyr Ile Ala Leu Lys
        275                 280                 285

Glu Asp Leu Arg Ser Trp Thr Ala Ala Asp Met Ala Ala Gln Thr Thr
    290                 295                 300

Lys His Lys Trp Glu Ala Ala His Val Ala Glu Gln Leu Arg Ala Tyr
305                 310                 315                 320

Leu Glu Gly Thr Cys Val Glu Trp Leu Arg Arg Tyr Leu Glu Asn Gly
                325                 330                 335

Lys Glu Thr Leu Gln Arg Thr Asp Ala Pro Lys Thr His Met Thr His
            340                 345                 350

His Ala Val Ser Asp His Glu Ala Thr Leu Arg Cys Trp Ala Leu Ser
        355                 360                 365

Phe Tyr Pro Ala Glu Ile Thr Leu Thr Trp Gln Arg Asp Gly Glu Asp
    370                 375                 380

Gln Thr Gln Asp Thr Glu Leu Val Glu Thr Arg Pro Ala Gly Asp Gly
385                 390                 395                 400

Thr Phe Gln Lys Trp Ala Ala Val Val Val Pro Ser Gly Gln Glu Gln
                405                 410                 415

Arg Tyr Thr Cys His Val Gln His Glu Gly Leu Pro Lys Pro Leu Thr
```

420 425 430

Leu Arg Trp Glu Pro Ser Ser Gln Pro Thr Ile Pro Ile Val Gly Ile
435 440 445

Ile Ala Gly Leu Val Leu Phe Gly Ala Val Ile Thr Gly Ala Val Val
450 455 460

Ala Ala Val Met Trp Arg Arg Lys Ser Ser
465 470

<210> SEQ ID NO 36
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 36
atgagccgca gcgtggcgct ggcggtgctg gcgctgctga gcctgagcgg cctggaagcg 60
agcctttaca acacggtcgc gacactgggt ggaggagcta gcggaggtgg tggtagtggt 120
ggtggtggtt ccatacaaag aactccaaag atccaagttt acagtagaca tcctgctgaa 180
aacggtaaat ctaatttctt gaactgttac gtctccggtt tccacccaag tgatatagaa 240
gttgacttgt tgaaaaatgg tgaaagaatc gaaaaggttg aacattcaga tttgtctttt 300
tctaaggact ggtccttcta tttgttgtac tacacagagt tcactccaac tgaaaaggat 360
gaatacgctt gcagagttaa tcatgtaacc ttgtctcaac ctaaaatcgt taagtgggat 420
agagacatgg gtggtggcgg cagtggtggc gggggcagcg gtggtggggg cagcggtggt 480
ggtggttccc atagtatgag atatttcttt acttctgttt caagaccagg tagaggtgaa 540
cctagattca tcgcagtcgg ttacgttgat gacacacaat ttgtaagatt cgattccgac 600
gctgcaagtc aaagaatgga accaagagca ccttggattg aacaagaagg tccagaatat 660
tgggatggtg aaactagaaa agttaaggcc cattctcaaa ctcacagagt agatttgggt 720
acattaagag gtgcttataa tcaatctgaa gcaggttcac atacagtaca aagaatgtac 780
ggttgtgatg tcggttcaga ctggagattt ttgagaggtt atcaccaata tgcttacgat 840
ggtaaagact acattgcatt gaaggaagat ttgagatcct ggaccgccgc tgacatggca 900
gcccaaacta caaaacataa gtgggaagct gcacacgtag cagaacaatt gagagcctat 960
ttggaaggta catgtgtcga atggttgaga agatacttag aaaacggtaa agaaacattg 1020
caaagaaccg atgctccaaa gactcatatg acacatcacg ccgttagtga tcacgaagct 1080
actttgagat gctgggcatt atctttttac cctgccgaaa tcacattgac ctggcaaaga 1140
gatggtgaag accaaaccca agatactgaa ttagttgaaa ccagaccagc aggtgacggt 1200
actttccaaa aatgggccgc tgttgtagtc ccttcaggtc aagaacaaag atacacatgc 1260
catgtccaac acgaaggttt accaaagcca ttgacattga gatgggaacc atcctctcag 1320
cctacaatac caatagtcgg cataatcgct ggactggtcc tgttcggggc ggtaatcacg 1380
ggagctgtag tcgctgcggt gatgtggcgc agaaaaagct cctga 1425

<210> SEQ ID NO 37
<211> LENGTH: 474
<212> TYPE: PRT
<213> ORGANISM: Artificial Sequence
<220> FEATURE:
<223> OTHER INFORMATION: Synthetic Polypeptide

<400> SEQUENCE: 37

-continued

```
Met Ser Arg Ser Val Ala Leu Ala Val Leu Ala Leu Leu Ser Leu Ser
1               5                   10                  15

Gly Leu Glu Ala Asn Leu Val Pro Met Val Ala Thr Val Gly Ala Ser
            20                  25                  30

Gly Gly Ser Gly Gly Gly Ser Gly Gly Gly Gly Ser Ile Gln Arg Thr
        35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
    130                 135                 140

Gly Gly Gly Ser Gly Gly Gly Gly Ser Gly Gly Gly Gly Ser Gly Gly
145                 150                 155                 160

Gly Gly Ser His Ser Met Arg Tyr Phe Phe Thr Ser Val Ser Arg Pro
                165                 170                 175

Gly Arg Gly Glu Pro Arg Phe Ile Ala Val Gly Tyr Val Asp Asp Thr
            180                 185                 190

Gln Phe Val Arg Phe Asp Ser Asp Ala Ala Ser Gln Arg Met Glu Pro
        195                 200                 205

Arg Ala Pro Trp Ile Glu Gln Glu Gly Pro Glu Tyr Trp Asp Gly Glu
    210                 215                 220

Thr Arg Lys Val Lys Ala His Ser Gln Thr His Arg Val Asp Leu Gly
225                 230                 235                 240

Thr Leu Arg Gly Ala Tyr Asn Gln Ser Glu Ala Gly Ser His Thr Val
                245                 250                 255

Gln Arg Met Tyr Gly Cys Asp Val Gly Ser Asp Trp Arg Phe Leu Arg
            260                 265                 270

Gly Tyr His Gln Tyr Ala Tyr Asp Gly Lys Asp Tyr Ile Ala Leu Lys
        275                 280                 285

Glu Asp Leu Arg Ser Trp Thr Ala Ala Asp Met Ala Ala Gln Thr Thr
    290                 295                 300

Lys His Lys Trp Glu Ala Ala His Val Ala Glu Gln Leu Arg Ala Tyr
305                 310                 315                 320

Leu Glu Gly Thr Cys Val Glu Trp Leu Arg Arg Tyr Leu Glu Asn Gly
                325                 330                 335

Lys Glu Thr Leu Gln Arg Thr Asp Ala Pro Lys Thr His Met Thr His
            340                 345                 350

His Ala Val Ser Asp His Glu Ala Thr Leu Arg Cys Trp Ala Leu Ser
        355                 360                 365

Phe Tyr Pro Ala Glu Ile Thr Leu Thr Trp Gln Arg Asp Gly Glu Asp
    370                 375                 380

Gln Thr Gln Asp Thr Glu Leu Val Glu Thr Arg Pro Ala Gly Asp Gly
385                 390                 395                 400

Thr Phe Gln Lys Trp Ala Ala Val Val Val Pro Ser Gly Gln Glu Gln
                405                 410                 415

Arg Tyr Thr Cys His Val Gln His Glu Gly Leu Pro Lys Pro Leu Thr
```

```
        420                 425                 430

Leu Arg Trp Glu Pro Ser Ser Gln Pro Thr Ile Pro Ile Val Gly Ile
    435                 440                 445

Ile Ala Gly Leu Val Leu Phe Gly Ala Val Ile Thr Gly Ala Val Val
  450                 455                 460

Ala Ala Val Met Trp Arg Arg Lys Ser Ser
465                 470
```

<210> SEQ ID NO 38
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 38

```
atgagccgca gcgtggcgct ggcggtgctg gcgctgctga gcctgagcgg cctggaagcg     60

aacttggttc cgatggtggc aaccgtaggt gctagcggag ggtccggcgg gggtagcggt    120

ggtggaggaa gcatacaaag aactccaaag atccaagttt acagtagaca tcctgctgaa    180

aacggtaaat ctaatttctt gaactgttac gtctccggtt tccacccaag tgatatagaa    240

gttgacttgt tgaaaaatgg tgaaagaatc gaaaaggttg aacattcaga tttgtctttt    300

tctaaggact ggtccttcta tttgttgtac tacacagagt tcactccaac tgaaaaggat    360

gaatacgctt gcagagttaa tcatgtaacc ttgtctcaac ctaaaatcgt taagtgggat    420

agagacatgg gtggtggcgg cagtggtggc gggggcagcg gtggtggggg cagcggtggt    480

ggtggttccc atagtatgag atatttcttt acttctgttt caagaccagg tagaggtgaa    540

cctagattca tcgcagtcgg ttacgttgat gacacacaat ttgtaagatt cgattccgac    600

gctgcaagtc aaagaatgga accaagagca ccttggattg aacaagaagg tccagaatat    660

tgggatggtg aaactagaaa agttaaggcc cattctcaaa ctcacagagt agatttgggt    720

acattaagag gtgcttataa tcaatctgaa gcaggttcac atacagtaca aagaatgtac    780

ggttgtgatg tcggttcaga ctggagattt ttgagaggtt atcaccaata tgcttacgat    840

ggtaaagact acattgcatt gaaggaagat ttgagatcct ggaccgccgc tgacatggca    900

gcccaaacta caaaacataa gtgggaagct gcacacgtag cagaacaatt gagagcctat    960

ttggaaggta catgtgtcga atggttgaga agatacttag aaaacggtaa agaaacattg   1020

caaagaaccg atgctccaaa gactcatatg acacatcacg ccgttagtga tcacgaagct   1080

actttgagat gctgggcatt atctttttac cctgccgaaa tcacattgac ctggcaaaga   1140

gatggtgaag accaaaccca agatactgaa ttagttgaaa ccagaccagc aggtgacggt   1200

actttccaaa aatgggccgc tgttgtagtc ccttcaggtc aagaacaaag atacacatgc   1260

catgtccaac acgaaggttt accaaagcca ttgacattga gatgggaacc atcctctcag   1320

cctacaatac caatagtcgg cataatcgct ggactggtcc tgttcggggc ggtaatcacg   1380

ggagctgtag tcgctgcggt gatgtggcgc agaaaaagct cctga                    1425
```

<210> SEQ ID NO 39
<211> LENGTH: 482
<212> TYPE: PRT
<213> ORGANISM: Artificial Sequence
<220> FEATURE:
<223> OTHER INFORMATION: Synthetic Polypeptide

<400> SEQUENCE: 39

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gly Ile Leu Gly Phe Val
            20                  25                  30

Phe Thr Leu Gly Cys Ser Gly Gly Ser Gly Gly Gly Ser Gly Gly Gly
        35                  40                  45

Gly Ser Ile Gln Arg Thr Pro Lys Ile Gln Val Tyr Ser Arg His Pro
    50                  55                  60

Ala Glu Asn Gly Lys Ser Asn Phe Leu Asn Cys Tyr Val Ser Gly Phe
65                  70                  75                  80

His Pro Ser Asp Ile Glu Val Asp Leu Leu Lys Asn Gly Glu Arg Ile
                85                  90                  95

Glu Lys Val Glu His Ser Asp Leu Ser Phe Ser Lys Asp Trp Ser Phe
            100                 105                 110

Tyr Leu Leu Tyr Tyr Thr Glu Phe Thr Pro Thr Glu Lys Asp Glu Tyr
        115                 120                 125

Ala Cys Arg Val Asn His Val Thr Leu Ser Gln Pro Lys Ile Val Lys
    130                 135                 140

Trp Asp Arg Asp Met Gly Gly Gly Gly Ser Gly Gly Ser Gly Ser Gly
145                 150                 155                 160

Gly Ser Gly Ser Gly Gly Gly Ser Gly Gly Ser His Ser Met Arg Tyr
                165                 170                 175

Phe Phe Thr Ser Val Ser Arg Pro Gly Arg Gly Glu Pro Arg Phe Ile
            180                 185                 190

Ala Val Gly Tyr Val Asp Asp Thr Gln Phe Val Arg Phe Asp Ser Asp
        195                 200                 205

Ala Ala Ser Gln Arg Met Glu Pro Arg Ala Pro Trp Ile Glu Gln Glu
    210                 215                 220

Gly Pro Glu Tyr Trp Asp Gly Glu Thr Arg Lys Val Lys Ala His Ser
225                 230                 235                 240

Gln Thr His Arg Val Asp Leu Gly Thr Leu Arg Gly Cys Tyr Asn Gln
                245                 250                 255

Ser Glu Ala Gly Ser His Thr Val Gln Arg Met Tyr Gly Cys Asp Val
            260                 265                 270

Gly Ser Asp Trp Arg Phe Leu Arg Gly Tyr His Gln Tyr Ala Tyr Asp
        275                 280                 285

Gly Lys Asp Tyr Ile Ala Leu Lys Glu Asp Leu Arg Ser Trp Thr Ala
    290                 295                 300

Ala Asp Met Ala Ala Gln Thr Thr Lys His Lys Trp Glu Ala Ala His
305                 310                 315                 320

Val Ala Glu Gln Leu Arg Ala Tyr Leu Glu Gly Thr Cys Val Glu Trp
                325                 330                 335

Leu Arg Arg Tyr Leu Glu Asn Gly Lys Glu Thr Leu Gln Arg Thr Asp
            340                 345                 350

Ala Pro Lys Thr His Met Thr His His Ala Val Ser Asp His Glu Ala
        355                 360                 365

Thr Leu Arg Cys Trp Ala Leu Ser Phe Tyr Pro Ala Glu Ile Thr Leu
    370                 375                 380

Thr Trp Gln Arg Asp Gly Glu Asp Gln Thr Gln Asp Thr Glu Leu Val
385                 390                 395                 400

Glu Thr Arg Pro Ala Gly Asp Gly Thr Phe Gln Lys Trp Ala Ala Val
                405                 410                 415

Val Val Pro Ser Gly Gln Glu Gln Arg Tyr Thr Cys His Val Gln His
```

```
            420                 425                 430

Glu Gly Leu Pro Lys Pro Leu Thr Leu Arg Trp Glu Pro Ser Ser Gln
        435                 440                 445

Pro Thr Ile Pro Ile Val Gly Ile Ile Ala Gly Leu Val Leu Phe Gly
    450                 455                 460

Ala Val Ile Thr Gly Ala Val Val Ala Ala Val Met Trp Arg Arg Lys
465                 470                 475                 480

Ser Ser


<210> SEQ ID NO 40
<211> LENGTH: 1449
<212> TYPE: DNA
<213> ORGANISM: Artificial Sequence
<220> FEATURE:
<223> OTHER INFORMATION: Synthetic Polynucleotide

<400> SEQUENCE: 40

atggcgacgg gttcaagaac ttccctactt cttgcatttg gcctgctttg tttgccgtgg     60

ttacaggagg gatccgcagg tatcctcgga tttgtgttta cacttggatg cagcggaggg    120

tccggcgggg gtagcggtgg tggaggaagc atacaaagaa ctccaaagat ccaagtttac    180

agtagacatc ctgctgaaaa cggtaaatct aatttcttga actgttacgt ctccggtttc    240

cacccaagtg atatagaagt tgacttgttg aaaaatggtg aaagaatcga aaaggttgaa    300

cattcagatt tgtctttttc taaggactgg tccttctatt tgttgtacta cacagagttc    360

actccaactg aaaaggatga atacgcttgc agagttaatc atgtaacctt gtctcaacct    420

aaaatcgtta agtgggatag agacatggga ggcggcggct ctggtggcag cggctctgga    480

ggttctggaa gtggaggcgg ctctggaggc tcccatagta tgagatattt ctttacttct    540

gtttcaagac caggtagagg tgaacctaga ttcatcgcag tcggttacgt tgatgacaca    600

caatttgtaa gattcgattc cgacgctgca agtcaaagaa tggaaccaag agcaccttgg    660

attgaacaag aaggtccaga atattgggat ggtgaaacta gaaaagttaa ggcccattct    720

caaactcaca gagtagattt gggtacatta agaggttgtt ataatcaatc tgaagcaggt    780

tcacatacag tacaaagaat gtacggttgt gatgtcggtt cagactggag atttttgaga    840

ggttatcacc aatatgctta cgatggtaaa gactacattg cattgaagga agatttgaga    900

tcctggaccg ccgctgacat ggcagcccaa actacaaaac ataagtggga agctgcacac    960

gtagcagaac aattgagagc ctatttggaa ggtacatgtg tcgaatggtt gagaagatac   1020

ttagaaaacg gtaaagaaac attgcaaaga accgatgctc caaagactca tatgacacat   1080

cacgccgtta gtgatcacga agctactttg agatgctggg cattatcttt ttaccctgcc   1140

gaaatcacat tgacctggca aagagatggt gaagaccaaa cccaagatac tgaattagtt   1200

gaaaccagac cagcaggtga cggtactttc caaaaatggg ccgctgttgt agtcccttca   1260

ggtcaagaac aaagatacac atgccatgtc caacacgaag gtttaccaaa gccattgaca   1320

ttgagatggg aaccatcctc tcagcctaca ataccaatag tcggcataat cgctggactg   1380

gtcctgttcg ggcggtaat cacgggagct gtagtcgctg cggtgatgtg gcgcagaaaa   1440

agctcctga                                                            1449


<210> SEQ ID NO 41
<211> LENGTH: 474
<212> TYPE: PRT
<213> ORGANISM: Artificial Sequence
<220> FEATURE:
```

<223> OTHER INFORMATION: Synthetic Polypeptide

<400> SEQUENCE: 41

```
Met Ser Arg Ser Val Ala Leu Ala Val Leu Ala Leu Leu Ser Leu Ser
1               5                   10                  15

Gly Leu Glu Ala Gly Ile Leu Gly Phe Val Phe Thr Leu Gly Gly Gly
            20                  25                  30

Ala Ser Gly Gly Gly Gly Ser Gly Gly Gly Gly Ser Ile Gln Arg Thr
        35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110

Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
    130                 135                 140

Gly Gly Gly Ser Gly Gly Gly Gly Ser Gly Gly Gly Gly Ser Gly Gly
145                 150                 155                 160

Gly Gly Ser His Ser Met Arg Tyr Phe Phe Thr Ser Val Ser Arg Pro
                165                 170                 175

Gly Arg Gly Glu Pro Arg Phe Ile Ala Val Gly Tyr Val Asp Asp Thr
            180                 185                 190

Gln Phe Val Arg Phe Asp Ser Asp Ala Ala Ser Gln Arg Met Glu Pro
        195                 200                 205

Arg Ala Pro Trp Ile Glu Gln Glu Gly Pro Glu Tyr Trp Asp Gly Glu
    210                 215                 220

Thr Arg Lys Val Lys Ala His Ser Gln Thr His Arg Val Asp Leu Gly
225                 230                 235                 240

Thr Leu Arg Gly Ala Tyr Asn Gln Ser Glu Ala Gly Ser His Thr Val
                245                 250                 255

Gln Arg Met Tyr Gly Cys Asp Val Gly Ser Asp Trp Arg Phe Leu Arg
            260                 265                 270

Gly Tyr His Gln Tyr Ala Tyr Asp Gly Lys Asp Tyr Ile Ala Leu Lys
        275                 280                 285

Glu Asp Leu Arg Ser Trp Thr Ala Ala Asp Met Ala Ala Gln Thr Thr
    290                 295                 300

Lys His Lys Trp Glu Ala Ala His Val Ala Glu Gln Leu Arg Ala Tyr
305                 310                 315                 320

Leu Glu Gly Thr Cys Val Glu Trp Leu Arg Arg Tyr Leu Glu Asn Gly
                325                 330                 335

Lys Glu Thr Leu Gln Arg Thr Asp Ala Pro Lys Thr His Met Thr His
            340                 345                 350

His Ala Val Ser Asp His Glu Ala Thr Leu Arg Cys Trp Ala Leu Ser
        355                 360                 365

Phe Tyr Pro Ala Glu Ile Thr Leu Thr Trp Gln Arg Asp Gly Glu Asp
    370                 375                 380

Gln Thr Gln Asp Thr Glu Leu Val Glu Thr Arg Pro Ala Gly Asp Gly
385                 390                 395                 400
```

-continued

```
Thr Phe Gln Lys Trp Ala Ala Val Val Val Pro Ser Gly Gln Glu Gln
                405                 410                 415

Arg Tyr Thr Cys His Val Gln His Glu Gly Leu Pro Lys Pro Leu Thr
            420                 425                 430

Leu Arg Trp Glu Pro Ser Ser Gln Pro Thr Ile Pro Ile Val Gly Ile
        435                 440                 445

Ile Ala Gly Leu Val Leu Phe Gly Ala Val Ile Thr Gly Ala Val Val
    450                 455                 460

Ala Ala Val Met Trp Arg Arg Lys Ser Ser
465                 470
```

<210> SEQ ID NO 42
<211> LENGTH: 1425
<212> TYPE: DNA
<213> ORGANISM: Artificial Sequence
<220> FEATURE:
<223> OTHER INFORMATION: Synthetic Polynucleotide

<400> SEQUENCE: 42

```
atgagccgca gcgtggcgct ggcggtgctg gcgctgctga gcctgagcgg cctggaagcg     60

ggtatcctcg gatttgtgtt tacacttggt ggaggagcta gcggaggtgg tggtagtggt    120

ggtggtggtt ccatacaaag aactccaaag atccaagttt acagtagaca tcctgctgaa    180

aacggtaaat ctaatttctt gaactgttac gtctccggtt tccacccaag tgatatagaa    240

gttgacttgt tgaaaaatgg tgaaagaatc gaaaaggttg aacattcaga tttgtctttt    300

tctaaggact ggtccttcta tttgttgtac tacacagagt tcactccaac tgaaaaggat    360

gaatacgctt gcagagttaa tcatgtaacc ttgtctcaac ctaaaatcgt taagtgggat    420

agagacatgg gtggtggcgg cagtggtggc gggggcagcg gtggtggggg cagcggtggt    480

ggtggttccc atagtatgag atatttcttt acttctgttt caagaccagg tagaggtgaa    540

cctagattca tcgcagtcgg ttacgttgat gacacacaat ttgtaagatt cgattccgac    600

gctgcaagtc aaagaatgga accaagagca ccttggattg aacaagaagg tccagaatat    660

tgggatggtg aaactagaaa agttaaggcc cattctcaaa ctcacagagt agatttgggt    720

acattaagag gtgcttataa tcaatctgaa gcaggttcac atacagtaca aagaatgtac    780

ggttgtgatg tcggttcaga ctggagattt ttgagaggtt atcaccaata tgcttacgat    840

ggtaaagact acattgcatt gaaggaagat ttgagatcct ggaccgccgc tgacatggca    900

gcccaaacta caaaacataa gtgggaagct gcacacgtag cagaacaatt gagagcctat    960

ttggaaggta catgtgtcga atggttgaga agatacttag aaaacggtaa agaaacattg   1020

caaagaaccg atgctccaaa gactcatatg acacatcacg ccgttagtga tcacgaagct   1080

actttgagat gctgggcatt atctttttac cctgccgaaa tcacattgac ctggcaaaga   1140

gatggtgaag accaaaccca agatactgaa ttagttgaaa ccagaccagc aggtgacggt   1200

actttccaaa aatgggccgc tgttgtagtc ccttcaggtc aagaacaaag atacacatgc   1260

catgtccaac acgaaggttt accaaagcca ttgacattga gatgggaacc atcctctcag   1320

cctacaatac caatagtcgg cataatcgct ggactggtcc tgttcggggc ggtaatcacg   1380

ggagctgtag tcgctgcggt gatgtggcgc agaaaaagct cctga                    1425
```

<210> SEQ ID NO 43
<211> LENGTH: 273
<212> TYPE: PRT
<213> ORGANISM: Artificial Sequence
<220> FEATURE:

<223> OTHER INFORMATION: Synthetic Polypeptide

<400> SEQUENCE: 43

Met Gly His Thr Arg Arg Gln Gly Thr Ser Pro Ser Lys Cys Pro Tyr
1 5 10 15

Leu Asn Phe Phe Gln Leu Leu Val Leu Ala Gly Leu Ser His Phe Cys
20 25 30

Ser Gly Val Ile His Val Thr Lys Glu Val Lys Glu Val Ala Thr Leu
35 40 45

Ser Cys Gly His Asn Val Ser Val Glu Glu Leu Ala Gln Thr Arg Ile
50 55 60

Tyr Trp Gln Lys Glu Lys Lys Met Val Leu Thr Met Met Ser Gly Asp
65 70 75 80

Met Asn Ile Trp Pro Glu Tyr Lys Asn Arg Thr Ile Phe Asp Ile Thr
85 90 95

Asn Asn Leu Ser Ile Val Ile Leu Ala Leu Arg Pro Ser Asp Glu Gly
100 105 110

Thr Tyr Glu Cys Val Val Leu Lys Tyr Glu Lys Asp Ala Phe Lys Arg
115 120 125

Glu His Leu Ala Glu Val Thr Leu Ser Val Lys Ala Asp Phe Pro Thr
130 135 140

Pro Ser Ile Ser Asp Phe Glu Ile Pro Thr Ser Asn Ile Arg Arg Ile
145 150 155 160

Ile Cys Ser Thr Ser Gly Gly Phe Pro Glu Pro His Leu Ser Trp Leu
165 170 175

Glu Asn Gly Glu Glu Leu Asn Ala Ile Asn Thr Thr Val Ser Gln Asp
180 185 190

Pro Glu Thr Glu Leu Tyr Ala Val Ser Ser Lys Leu Asp Phe Asn Met
195 200 205

Thr Thr Asn His Ser Phe Met Cys Leu Ile Lys Tyr Gly His Leu Arg
210 215 220

Val Asn Gln Thr Phe Asn Trp Asn Thr Thr Lys Gln Glu His Phe Pro
225 230 235 240

Asp Asn Leu Leu Pro Ser Trp Ala Ile Thr Leu Ile Ser Val Asn Gly
245 250 255

Ile Phe Val Ile Cys Cys Leu Thr Tyr Cys Phe Ala Pro Arg Cys Arg
260 265 270

Glu

<210> SEQ ID NO 44
<211> LENGTH: 822
<212> TYPE: DNA
<213> ORGANISM: Artificial Sequence
<220> FEATURE:
<223> OTHER INFORMATION: Synthetic Polynucleotide

<400> SEQUENCE: 44
atgggtcata cacgccgcca aggaacctca ccatctaagt gcccatatct gaatttcttt 60
caacttctcg tgctggcggg gctcagtcat ttctgcagtg gggtcattca cgttactaaa 120
gaggtcaagg aggtcgcaac attgagttgt ggccataacg tatcagttga agaactcgcg 180
cagacacgga tttactggca aaaggaaaag aagatggtgt tgacaatgat gagcggtgac 240
atgaacattt ggccagagta caaaaatcga acgatattcg atataaccaa taacttgtcc 300
atagtaatac ttgccttgcg accttctgac gagggaacgt atgaatgtgt agtgcttaag 360

-continued

```
tatgaaaaag atgcctttaa gcgggaacac ttggctgagg ttacactctc cgttaaggcg    420

gactttccta cgccgtctat atccgacttc gagataccca cttctaacat tcgacgcatc    480

atttgctcaa cctcaggtgg tttcccagag cctcacttga gctggctgga gaatggcgaa    540

gaacttaacg caatcaatac cacggtgtcc caagacccgg agacagagct gtacgccgtg    600

tcatccaaac tggattttaa catgacgaca aatcatagtt tcatgtgtct gatcaaatat    660

gggcatctca gggtgaatca gacttttaat tggaacacta ccaaacaaga gcacttccca    720

gataatctgt tgccaagctg ggcgataact cttatctccg tcaacggtat cttcgtaatt    780

tgctgcctca cctattgttt cgcgcctcga tgccgagaat ga                        822


<210> SEQ ID NO 45
<211> LENGTH: 275
<212> TYPE: PRT
<213> ORGANISM: Artificial Sequence
<220> FEATURE:
<223> OTHER INFORMATION: Synthetic Polypeptide

<400> SEQUENCE: 45

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
        35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Val Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg
        275
```

<210> SEQ ID NO 46
<211> LENGTH: 828
<212> TYPE: DNA
<213> ORGANISM: Artificial Sequence
<220> FEATURE:
<223> OTHER INFORMATION: Synthetic Polynucleotide

<400> SEQUENCE: 46
atggatccgc aatgcacaat ggggcttagc aacattctct ttgtaatggc ttttctcctg 60
tccggtgcag cgcccctcaa gattcaggca tattttaacg aaaccgcgga cctcccttgt 120
cagttcgcaa atagtcagaa tcaaagtctc agtgagttgg tcgtattttg gcaggatcaa 180
gagaatctcg tcctgaacga ggtttacctg ggcaaagaga agtttgattc cgtgcatagt 240
aagtacatgg gtcgcacgtc ctttgactcc gacagctgga cacttaggct gcacaacctc 300
cagatcaaag ataagggtct ttaccagtgc attatacacc ataaaaaacc tactgggatg 360
atcaggattc accagatgaa cagcgagttg tcagtgttgg caaatttctc acaaccagaa 420
atagtaccta tctcaaacat caccgaaaac gtatatatta acctcacctg ttctagtatc 480
catggttatc cagagccaaa gaaaatgtcc gtgttgctga gaacaaagaa ctctacaata 540
gagtacgacg gagtgatgca aaaatcccag gacaacgtaa cagaactgta cgatgttagc 600
atctctcttt ctgtgagctt tcctgatgtg acatccaaca tgaccatttt ttgcatactc 660
gaaacagaca aaacgcgact tttgtcctcc cccttttcaa tcgagttgga ggatccccaa 720
cctccccccg accatatccc gtggatcacc gctgttcttc ctaccgtaat catctgtgtc 780
atggtattct gccttattct ctggaaatgg aagaaaaaga agcgatga 828

<210> SEQ ID NO 47
<211> LENGTH: 551
<212> TYPE: PRT
<213> ORGANISM: Artificial Sequence
<220> FEATURE:
<223> OTHER INFORMATION: Synthetic Polypeptide

<400> SEQUENCE: 47

Met Glu Thr Asp Thr Leu Leu Leu Trp Val Leu Leu Leu Trp Val Pro
1 5 10 15

Gly Ser Thr Gly Ala Asp Tyr Lys Asp Asp Asp Asp Lys Asp Ile Gln
20 25 30

Met Thr Gln Ser Pro Ser Ser Leu Pro Ala Ser Leu Gly Asp Arg Val
35 40 45

Thr Ile Asn Cys Gln Ala Ser Gln Asp Ile Ser Asn Tyr Leu Asn Trp
50 55 60

Tyr Gln Gln Lys Pro Gly Lys Ala Pro Lys Leu Leu Ile Tyr Tyr Thr
65 70 75 80

Asn Lys Leu Ala Asp Gly Val Pro Ser Arg Phe Ser Gly Ser Gly Ser
85 90 95

Gly Arg Asp Ser Ser Phe Thr Ile Ser Ser Leu Glu Ser Glu Asp Ile
100 105 110

Gly Ser Tyr Tyr Cys Gln Gln Tyr Tyr Asn Tyr Pro Trp Thr Phe Gly
115 120 125

Pro Gly Thr Lys Leu Glu Ile Lys Arg Ala Asp Ala Lys Pro Thr Val
130 135 140

Ser Ile Phe Pro Pro Ser Ser Glu Gln Leu Gly Thr Gly Ser Ala Thr
145 150 155 160

```
Leu Val Cys Phe Val Asn Asn Phe Tyr Pro Lys Asp Ile Asn Val Lys
                165                 170                 175

Trp Lys Val Asp Gly Ser Glu Lys Arg Asp Gly Val Leu Gln Ser Val
            180                 185                 190

Thr Asp Gln Asp Ser Lys Asp Ser Thr Tyr Ser Leu Ser Ser Thr Leu
        195                 200                 205

Ser Leu Thr Lys Ala Asp Tyr Glu Arg His Asn Leu Tyr Thr Cys Glu
    210                 215                 220

Val Thr His Lys Thr Ser Thr Ala Ala Ile Val Lys Thr Leu Asn Arg
225                 230                 235                 240

Asn Glu Cys Gly Ser Gly Ala Thr Asn Phe Ser Leu Leu Lys Gln Ala
                245                 250                 255

Gly Asp Val Glu Glu Asn Pro Gly Pro Met Val Pro Cys Thr Leu Leu
            260                 265                 270

Leu Leu Leu Ala Ala Ala Leu Ala Pro Thr Gln Thr Arg Ala Glu Val
        275                 280                 285

Gln Leu Val Glu Ser Gly Gly Gly Leu Val Gln Pro Gly Lys Ser Leu
    290                 295                 300

Lys Leu Ser Cys Glu Ala Ser Gly Phe Thr Phe Ser Gly Tyr Gly Met
305                 310                 315                 320

His Trp Val Arg Gln Ala Pro Gly Arg Gly Leu Glu Ser Val Ala Tyr
                325                 330                 335

Ile Thr Ser Ser Ser Ile Asn Ile Lys Tyr Ala Asp Ala Val Lys Gly
            340                 345                 350

Arg Phe Thr Val Ser Arg Asp Asn Ala Lys Asn Leu Leu Phe Leu Gln
        355                 360                 365

Met Asn Ile Leu Lys Ser Glu Asp Thr Ala Met Tyr Tyr Cys Ala Arg
    370                 375                 380

Phe Asp Trp Asp Lys Asn Tyr Trp Gly Gln Gly Thr Met Val Thr Val
385                 390                 395                 400

Ser Ser Ala Lys Thr Thr Ala Pro Ser Val Tyr Pro Leu Ala Pro Ala
                405                 410                 415

Cys Asp Ser Thr Thr Ser Thr Thr Asn Thr Val Thr Leu Gly Cys Leu
            420                 425                 430

Val Lys Gly Tyr Phe Pro Glu Pro Val Thr Val Ile Trp Asn Ser Gly
        435                 440                 445

Ala Leu Thr Ser Gly Val His Thr Phe Pro Ser Val Leu His Ser Gly
    450                 455                 460

Leu Tyr Ser Leu Ser Ser Ser Val Thr Val Pro Ser Ser Thr Trp Pro
465                 470                 475                 480

Ser Gln Thr Val Thr Cys Asn Val Ala His Pro Ala Ser Ser Thr Thr
                485                 490                 495

Val Asp Leu Lys Ile Glu Ala Val Gly Gln Asp Thr Gln Glu Val Ile
            500                 505                 510

Val Val Pro His Ser Leu Pro Phe Lys Val Val Val Ile Ser Ala Ile
        515                 520                 525

Leu Ala Leu Val Val Leu Thr Ile Ile Ser Leu Ile Ile Leu Ile Met
    530                 535                 540

Leu Trp Gln Lys Lys Pro Arg
545                 550
```

<210> SEQ ID NO 48
<211> LENGTH: 1656
<212> TYPE: DNA

-continued

<213> ORGANISM: Artificial Sequence
<220> FEATURE:
<223> OTHER INFORMATION: Synthetic Polynucleotide

<400> SEQUENCE: 48

```
atggaaaccg acaccttgct cctgtgggtt ctcctgttgt gggtgccggg atcaacggga     60
gctgattaca aggatgacga cgataaggac attcaaatga cccagtctcc ttccagcctg    120
ccagcgagcc tgggggacag agtgaccatt aactgtcagg cttcacagga tattagcaat    180
tacctcaact ggtatcaaca gaagccaggc aaggccccca aactgctcat ttattacacg    240
aacaaactgg cggacggtgt tccttccaga tttagcggct ccggttccgg gcgggacagt    300
agctttacta taagcagttt ggaatccgag gacataggtt cctattactg ccagcagtat    360
tacaattacc cttggacatt tggtccgggt actaagctcg agataaagcg ggccgatgcc    420
aagcccaccg tatcaatctt cccgccatcc agtgagcagc tcggtacagg aagcgcgact    480
ctggtttgtt tcgttaacaa tttttatcct aaggacataa acgttaagtg gaaggtagac    540
ggaagcgaga aacgagatgg tgtattgcag agtgtcacag accaggattc caaagactcc    600
acatactccc tctcctcaac tcttagtctt acgaaggctg attacgaaag gcacaacctg    660
tatacgtgtg aggtcactca taaaaccagt actgcggcga ttgtaaaaac gctgaacagg    720
aacgaatgtg gaagtggtgc tacgaacttc tcactgctta agcaagctgg agatgttgag    780
gaaaaccctg gaccaatggt gccgtgcacc ctcctttttgc ttttggccgc tgcgttggct    840
ccaacccaga ctagggcaga agtacagctt gtggaaagcg gcggagggct tgtgcagcct    900
ggcaaatccc tcaaactcag ttgtgaggct agtggcttca catttagcgg gtacggtatg    960
cactgggtcc gacaggcacc tggcgcgcgga ttggaaagcg tcgcatacat tacaagctca   1020
agcataaata taaaatatgc ggatgctgtc aaggggagat tcaccgtttc tagggataac   1080
gcgaagaacc ttttgttcct gcaaatgaac attctcaaga gcgaggacac ggctatgtac   1140
tattgtgcta ggttcgactg ggacaagaat tattggggac aaggtactat ggttacagta   1200
agtagtgcta aaactactgc tccgtcagta tatcccctcg caccagcctg cgattctact   1260
accagcacta ctaatacagt aacactcggg tgcctcgtga aggggtattt ccctgaacca   1320
gttacggtca tctggaatag tggggccttg actagtggtg tacatacgtt cccatccgtc   1380
cttcactcag gactctacag cctcagctca agtgttaccg taccctcttc aacatggccg   1440
tctcagacag ttacgtgcaa cgtcgctcat cctgcaagtt ccacgactgt ggaccttaaa   1500
attgaagccg tcggccagga cacccaggag gtaattgttg tcccacattc acttccattc   1560
aaggtggtcg tgatctctgc gatcctcgcg ctcgtcgttt tgacgatcat tagcctcatc   1620
atcctcatca tgttgtggca gaaaaagccc cggtaa                             1656
```

<210> SEQ ID NO 49
<211> LENGTH: 555
<212> TYPE: PRT
<213> ORGANISM: Artificial Sequence
<220> FEATURE:
<223> OTHER INFORMATION: Synthetic Polypeptide

<400> SEQUENCE: 49

```
Met Glu Thr Asp Thr Leu Leu Leu Trp Val Leu Leu Leu Trp Val Pro
1               5                   10                  15

Gly Ser Thr Gly Ala Asp Tyr Lys Asp Asp Asp Asp Lys Tyr Glu Leu
            20                  25                  30

Ile Gln Pro Ser Ser Ala Ser Val Thr Val Gly Glu Thr Val Lys Ile
```

```
        35                  40                  45

Thr Cys Ser Gly Asp Gln Leu Pro Lys Asn Phe Ala Tyr Trp Phe Gln
    50                  55                  60

Gln Lys Ser Asp Lys Asn Ile Leu Leu Leu Ile Tyr Met Asp Asn Lys
65                  70                  75                  80

Arg Pro Ser Gly Ile Pro Glu Arg Phe Ser Gly Ser Thr Ser Gly Thr
                85                  90                  95

Thr Ala Thr Leu Thr Ile Ser Gly Ala Gln Pro Glu Asp Glu Ala Ala
            100                 105                 110

Tyr Tyr Cys Leu Ser Ser Tyr Gly Asp Asn Asn Asp Leu Val Phe Gly
        115                 120                 125

Ser Gly Thr Gln Leu Thr Val Leu Arg Gly Pro Lys Ser Ser Pro Lys
    130                 135                 140

Val Thr Val Phe Pro Pro Ser Pro Glu Glu Leu Arg Thr Asn Lys Ala
145                 150                 155                 160

Thr Leu Val Cys Leu Val Asn Asp Phe Tyr Pro Gly Ser Ala Thr Val
                165                 170                 175

Thr Trp Lys Ala Asn Gly Ala Thr Ile Asn Asp Gly Val Lys Thr Thr
            180                 185                 190

Lys Pro Ser Lys Gln Gly Gln Asn Tyr Met Thr Ser Ser Tyr Leu Ser
        195                 200                 205

Leu Thr Ala Asp Gln Trp Lys Ser His Asn Arg Val Ser Cys Gln Val
    210                 215                 220

Thr His Glu Gly Glu Thr Val Glu Lys Ser Leu Ser Pro Ala Glu Cys
225                 230                 235                 240

Leu Gly Ser Gly Ala Thr Asn Phe Ser Leu Leu Lys Gln Ala Gly Asp
                245                 250                 255

Val Glu Glu Asn Pro Gly Pro Met Val Pro Cys Thr Leu Leu Leu Leu
            260                 265                 270

Leu Ala Ala Ala Leu Ala Pro Thr Gln Thr Arg Ala Glu Val Tyr Leu
        275                 280                 285

Val Glu Ser Gly Gly Asp Leu Val Gln Pro Gly Ser Ser Leu Lys Val
    290                 295                 300

Ser Cys Ala Ala Ser Gly Phe Thr Phe Ser Asp Phe Trp Met Tyr Trp
305                 310                 315                 320

Val Arg Gln Ala Pro Gly Lys Gly Leu Glu Trp Val Gly Arg Ile Lys
                325                 330                 335

Asn Ile Pro Asn Asn Tyr Ala Thr Glu Tyr Ala Asp Ser Val Arg Gly
            340                 345                 350

Arg Phe Thr Ile Ser Arg Asp Asp Ser Arg Asn Ser Ile Tyr Leu Gln
        355                 360                 365

Met Asn Arg Leu Arg Val Asp Asp Thr Ala Ile Tyr Tyr Cys Thr Arg
    370                 375                 380

Ala Gly Arg Phe Asp His Phe Asp Tyr Trp Gly Gln Gly Thr Met Val
385                 390                 395                 400

Thr Val Ser Ser Ala Thr Thr Thr Ala Pro Ser Val Tyr Pro Leu Ala
                405                 410                 415

Pro Ala Cys Asp Ser Thr Thr Ser Thr Thr Asp Thr Val Thr Leu Gly
            420                 425                 430

Cys Leu Val Lys Gly Tyr Phe Pro Glu Pro Val Thr Val Ser Trp Asn
        435                 440                 445

Ser Gly Ala Leu Thr Ser Gly Val His Thr Phe Pro Ser Val Leu His
    450                 455                 460
```

```
Ser Gly Leu Tyr Ser Leu Ser Ser Ser Val Thr Val Pro Ser Ser Thr
465                 470                 475                 480

Trp Pro Lys Gln Pro Ile Thr Cys Asn Val Ala His Pro Ala Ser Ser
                485                 490                 495

Thr Lys Val Asp Lys Lys Ile Glu Pro Arg Ala Val Gly Gln Asp Thr
            500                 505                 510

Gln Glu Val Ile Val Val Pro His Ser Leu Pro Phe Lys Val Val Val
        515                 520                 525

Ile Ser Ala Ile Leu Ala Leu Val Val Leu Thr Ile Ile Ser Leu Ile
    530                 535                 540

Ile Leu Ile Met Leu Trp Gln Lys Lys Pro Arg
545                 550                 555
```

<210> SEQ ID NO 50
<211> LENGTH: 1668
<212> TYPE: DNA
<213> ORGANISM: Artificial Sequence
<220> FEATURE:
<223> OTHER INFORMATION: Synthetic Polynucleotide

<400> SEQUENCE: 50

```
atggaaaccg acaccttgct cctgtgggtt ctcctgttgt gggtgccggg atcaacggga     60

gctgattaca aggatgacga cgataagtat gaattgatcc aaccctccag tgcgagtgtc    120

actgtcggtg agaccgttaa aataacttgt agcggcgacc aacttccgaa gaactttgct    180

tactggtttc aacaaaagtc agacaagaat atattgcttt tgatatatat ggacaataag    240

agacccagtg ggattccaga gagattttcc ggctcaacct ctggaacaac agccacactt    300

acgatatcag ggcccagcc tgaagacgag gcagcgtact actgcctttc ctcctacgga    360

gataataacg atcttgtgtt cggctccgga acacagctta ccgttctgcg gggaccaaag    420

agcagtccca aagtaaccgt ctttccccca agccccgagg agcttaggac taataaagcg    480

acgctggtct gtcttgtcaa tgacttttac cctggctcag ccacagtgac atggaaggca    540

aatggggcca ctattaacga cggtgtcaag actacgaagc caagcaaaca ggggcaaaac    600

tacatgacaa gcagctactt gagtttgact gcggaccagt ggaagtctca caatagagtt    660

agctgtcaag tcacacatga aggcgagact gttgaaaaat cactctcccc tgcggaatgc    720

ttgggaagtg gtgctacgaa cttctcactg cttaagcaag ctggagatgt tgaggaaaac    780

cctggaccaa tggtgccgtg caccctcctt ttgcttttgg ccgctgcgtt ggctccaacc    840

cagactaggg cagaggttta tcttgttgag tccggaggtg acttggtgca gcctggctct    900

tcccttaagg tctcatgcgc cgcatccggc tttacattct ctgatttttg gatgtattgg    960

gttcgccagg ctcctggtaa agggctggaa tgggtgggca gaatcaagaa catccccaat   1020

aactacgcta cagaatatgc cgactcagtg agggggcgct tcactatatc acgagacgat   1080

tcacggaact ctatttatct gcagatgaac cggttgaggg ttgatgacac cgcgatatat   1140

tattgcacca gagctggcag gtttgaccac tttgactact ggggacaggg tacgatggtg   1200

actgtgagta gcgcaacgac aaccgcacct tcagtgtacc cactcgctcc tgcttgcgac   1260

tccaccacta gcacgacaga caccgtcact ctcggatgtt tggtaaaagg atattttcca   1320

gaacctgtca ccgtttcttg gaatagtggc gcattgactt caggtgtcca tacgttccct   1380

tccgtcttgc acagtggact gtactcattg tcatctagtg ttacagtacc gtcctccaca   1440

tggccgaagc agccgataac ttgtaatgtc gcccatccag cctcctccac taaggtggac   1500
```

aagaaaatag agcctagagc cgtcggccag gacacccagg aggtaattgt tgtcccacat 1560
tcacttccat tcaaggtggt cgtgatctct gcgatcctcg cgctcgtcgt tttgacgatc 1620
attagcctca tcatcctcat catgttgtgg cagaaaaagc cccggtaa 1668

<210> SEQ ID NO 51
<211> LENGTH: 512
<212> TYPE: PRT
<213> ORGANISM: Artificial Sequence
<220> FEATURE:
<223> OTHER INFORMATION: Synthetic Polypeptide

<400> SEQUENCE: 51

Met Asn Phe Leu Leu Leu Thr Phe Ile Val Leu Pro Leu Cys Ser His
1 5 10 15

Ala Lys Phe Ser Ile Val Phe Pro Gln Ser Gln Lys Gly Asn Trp Lys
20 25 30

Asn Val Pro Ser Ser Tyr His Tyr Cys Pro Ser Ser Ser Asp Gln Asn
35 40 45

Trp His Asn Asp Leu Leu Gly Ile Thr Met Lys Val Lys Met Pro Lys
50 55 60

Thr His Lys Ala Ile Gln Ala Asp Gly Trp Met Cys His Ala Ala Lys
65 70 75 80

Trp Ile Thr Thr Cys Asp Phe Arg Trp Tyr Gly Pro Lys Tyr Ile Thr
85 90 95

His Ser Ile His Ser Ile Gln Pro Thr Ser Glu Gln Cys Lys Glu Ser
100 105 110

Ile Lys Gln Thr Lys Gln Gly Thr Trp Met Ser Pro Gly Phe Pro Pro
115 120 125

Gln Asn Cys Gly Tyr Ala Thr Val Thr Asp Ser Val Ala Val Val Val
130 135 140

Gln Ala Thr Pro His His Val Leu Val Asp Glu Tyr Thr Gly Glu Trp
145 150 155 160

Ile Asp Ser Gln Phe Pro Asn Gly Lys Cys Glu Thr Glu Glu Cys Glu
165 170 175

Thr Val His Asn Ser Thr Val Trp Tyr Ser Asp Tyr Lys Val Thr Gly
180 185 190

Leu Cys Asp Ala Thr Leu Val Asp Thr Glu Ile Thr Phe Phe Ser Glu
195 200 205

Asp Gly Lys Lys Glu Ser Ile Gly Lys Pro Asn Thr Gly Tyr Arg Ser
210 215 220

Asn Tyr Phe Ala Tyr Glu Lys Gly Asp Lys Val Cys Lys Met Asn Tyr
225 230 235 240

Cys Lys His Ala Gly Val Arg Leu Pro Ser Gly Val Trp Phe Glu Phe
245 250 255

Val Asp Gln Asp Val Tyr Ala Ala Ala Lys Leu Pro Glu Cys Pro Val
260 265 270

Gly Ala Thr Ile Ser Ala Pro Thr Gln Thr Ser Val Asp Val Ser Leu
275 280 285

Ile Leu Asp Val Glu Arg Ile Leu Asp Tyr Ser Leu Cys Gln Glu Thr
290 295 300

Trp Ser Lys Ile Arg Ser Lys Gln Pro Val Ser Pro Val Asp Leu Ser
305 310 315 320

Tyr Leu Ala Pro Lys Asn Pro Gly Thr Gly Pro Ala Phe Thr Ile Ile
325 330 335

-continued

Asn Gly Thr Leu Lys Tyr Phe Glu Thr Arg Tyr Ile Arg Ile Asp Ile
340 345 350

Asp Asn Pro Ile Ile Ser Lys Met Val Gly Lys Ile Ser Gly Ser Gln
355 360 365

Thr Glu Arg Glu Leu Trp Thr Glu Trp Phe Pro Tyr Glu Gly Val Glu
370 375 380

Ile Gly Pro Asn Gly Ile Leu Lys Thr Pro Thr Gly Tyr Lys Phe Pro
385 390 395 400

Leu Phe Met Ile Gly His Gly Met Leu Asp Ser Asp Leu His Lys Thr
405 410 415

Ser Gln Ala Glu Val Phe Glu His Pro His Leu Ala Glu Ala Pro Lys
420 425 430

Gln Leu Pro Glu Glu Glu Thr Leu Phe Phe Gly Asp Thr Gly Ile Ser
435 440 445

Lys Asn Pro Val Glu Leu Ile Glu Gly Trp Phe Ser Ser Trp Lys Ser
450 455 460

Thr Val Val Thr Phe Phe Phe Ala Ile Gly Val Phe Ile Leu Leu Tyr
465 470 475 480

Val Val Ala Arg Ile Val Ile Ala Val Arg Tyr Arg Tyr Gln Gly Ser
485 490 495

Asn Asn Lys Arg Ile Tyr Asn Asp Ile Glu Met Ser Arg Phe Arg Lys
500 505 510

<210> SEQ ID NO 52
<211> LENGTH: 1539
<212> TYPE: DNA
<213> ORGANISM: Artificial Sequence
<220> FEATURE:
<223> OTHER INFORMATION: Synthetic Polynucleotide

<400> SEQUENCE: 52
atgaactttc tgctgctcac gtttatcgta ctcccgttgt gctctcatgc gaaattttca 60
atagtctttc ctcagtccca gaaagggaat tggaaaaatg ttccctccag ttaccactat 120
tgtccctcct cctctgacca aaactggcac aatgacttgc tcgggattac aatgaaagta 180
aagatgccga aaacccataa agccatacag gcggatgggt ggatgtgtca cgctgcgaag 240
tggatcacta catgcgattt ccggtggtat ggccctaagt acattacaca ctctatccat 300
agcatacagc cgacatcaga gcaatgcaaa gagagtatta aacagaccaa acaagggaca 360
tggatgagcc ctggctttcc acctcagaat tgtgggtacg cgaccgtcac ggatagtgtc 420
gctgttgtgg tgcaggccac gccacatcac gtactcgtag atgaatatac tggtgaatgg 480
atcgactccc aattcccgaa tgggaaatgt gagacggaag agtgcgaaac agtgcataac 540
tcaaccgttt ggtattccga ttacaaggtt actggtcttt gcgacgccac cctcgtggat 600
accgagatca cgttttttag tgaggatggc aagaaagagt caataggcaa acctaatact 660
ggctaccgga gtaactattt cgcttacgag aagggtgaca aggtatgtaa aatgaactat 720
tgcaagcatg cgggagtgcg actccccagt ggggtatggt tcgaatttgt tgaccaagac 780
gtatacgccg ctgcgaagtt gccagaatgc cccgtaggcg cgaccatttc agcacctacc 840
caaacgtccg ttgacgtctc cttgatactg gatgtagagc gaatcctgga ctacagtctc 900
tgccaggaaa cgtggtcaaa aataagaagt aagcagccag tttcacccgt ggatctgtct 960
tatctggcgc caaaaaaccc gggcacgggc cctgctttta ccataattaa cggaacgctt 1020
aaatacttcg aaacccgcta cattagaatc gatatagaca atcctattat cagcaagatg 1080

-continued

```
gtagggaaga tatctgggtc tcaaacggag cgagaattgt ggacggagtg gttcccttat   1140

gagggagtgg aaattgggcc caacgggatc ctcaagaccc caacgggtta caagttccct   1200

ctgtttatga tcggccatgg catgttggac agtgacttgc acaaaacatc tcaggcagag   1260

gttttcgaac atccacattt ggcggaggcg cccaagcaac ttccagaaga agaaactctc   1320

ttctttggag atacaggcat ttcaaaaaat cctgtagaac tgatagaagg gtggttctct   1380

tcctggaaat caacggttgt cacgtttttc tttgcaatag gcgtatttat actcctgtac   1440

gtcgtagccc gcattgtgat cgcagtacga tacagatacc agggcagtaa caataaacgc   1500

atatataatg acatcgaaat gtcaaggttc cgaaagtga                          1539
```

```
<210> SEQ ID NO 53
<211> LENGTH: 512
<212> TYPE: PRT
<213> ORGANISM: Artificial Sequence
<220> FEATURE:
<223> OTHER INFORMATION: Synthetic Polypeptide

<400> SEQUENCE: 53

Met Asn Phe Leu Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
            20                  25                  30

Asn Val Pro Ser Ser Tyr His Tyr Cys Pro Ser Ser Ser Asp Gln Asn
        35                  40                  45

Trp His Asn Asp Leu Leu Gly Ile Thr Met Lys Val Lys Met Pro Gln
    50                  55                  60

Thr His Lys Ala Ile Gln Ala Asp Gly Trp Met Cys His Ala Ala Lys
65                  70                  75                  80

Trp Ile Thr Thr Cys Asp Phe Arg Trp Tyr Gly Pro Lys Tyr Ile Thr
                85                  90                  95

His Ser Ile His Ser Ile Gln Pro Thr Ser Glu Gln Cys Lys Glu Ser
            100                 105                 110

Ile Lys Gln Thr Lys Gln Gly Thr Trp Met Ser Pro Gly Phe Pro Pro
        115                 120                 125

Gln Asn Cys Gly Tyr Ala Thr Val Thr Asp Ser Val Ala Val Val Val
    130                 135                 140

Gln Ala Thr Pro His His Val Leu Val Asp Glu Tyr Thr Gly Glu Trp
145                 150                 155                 160

Ile Asp Ser Gln Phe Pro Asn Gly Lys Cys Glu Thr Glu Glu Cys Glu
                165                 170                 175

Thr Val His Asn Ser Thr Val Trp Tyr Ser Asp Tyr Lys Val Thr Gly
            180                 185                 190

Leu Cys Asp Ala Thr Leu Val Asp Thr Glu Ile Thr Phe Phe Ser Glu
        195                 200                 205

Asp Gly Lys Lys Glu Ser Ile Gly Lys Pro Asn Thr Gly Tyr Arg Ser
    210                 215                 220

Asn Tyr Phe Ala Tyr Glu Lys Gly Asp Lys Val Cys Lys Met Asn Tyr
225                 230                 235                 240

Cys Lys His Ala Gly Val Arg Leu Pro Ser Gly Val Trp Phe Glu Phe
                245                 250                 255

Val Asp Gln Asp Val Tyr Ala Ala Ala Lys Leu Pro Glu Cys Pro Val
            260                 265                 270

Gly Ala Thr Ile Ser Ala Pro Thr Gln Thr Ser Val Asp Val Ser Leu
        275                 280                 285
```

```
Ile Leu Asp Val Glu Arg Ile Leu Asp Tyr Ser Leu Cys Gln Glu Thr
    290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Ile Asp Ile
            340                 345                 350

Asp Asn Pro Ile Ile Ser Lys Met Val Gly Lys Ile Ser Gly Ser Gln
        355                 360                 365

Thr Glu Ala Glu Leu Trp Thr Glu Trp Phe Pro Tyr Glu Gly Val Glu
    370                 375                 380

Ile Gly Pro Asn Gly Ile Leu Lys Thr Pro Thr Gly Tyr Lys Phe Pro
385                 390                 395                 400

Leu Phe Met Ile Gly His Gly Met Leu Asp Ser Asp Leu His Lys Thr
                405                 410                 415

Ser Gln Ala Glu Val Phe Glu His Pro His Leu Ala Glu Ala Pro Lys
            420                 425                 430

Gln Leu Pro Glu Glu Glu Thr Leu Phe Phe Gly Asp Thr Gly Ile Ser
        435                 440                 445

Lys Asn Pro Val Glu Leu Ile Glu Gly Trp Phe Ser Ser Trp Lys Ser
    450                 455                 460

Thr Val Val Thr Phe Phe Phe Ala Ile Gly Val Phe Ile Leu Leu Tyr
465                 470                 475                 480

Val Val Ala Arg Ile Val Ile Ala Val Arg Tyr Arg Tyr Gln Gly Ser
                485                 490                 495

Asn Asn Lys Arg Ile Tyr Asn Asp Ile Glu Met Ser Arg Phe Arg Lys
            500                 505                 510


<210> SEQ ID NO 54
<211> LENGTH: 1539
<212> TYPE: DNA
<213> ORGANISM: Artificial Sequence
<220> FEATURE:
<223> OTHER INFORMATION: Synthetic Polynucleotide

<400> SEQUENCE: 54

atgaactttc tgctgctcac gtttatcgta ctcccgttgt gctctcatgc gaaattttca     60

atagtctttc ctcagtccca gaaagggaat tggaaaaatg ttccctccag ttaccactat    120

tgtccctcct cctctgacca aaactggcac aatgacttgc tcgggattac aatgaaagta    180

aagatgccgc agacccataa agccatacag gcggatgggt ggatgtgtca cgctgcgaag    240

tggatcacta catgcgattt ccggtggtat ggccctaagt acattacaca ctctatccat    300

agcatacagc cgacatcaga gcaatgcaaa gagagtatta aacagaccaa acaagggaca    360

tggatgagcc ctggctttcc acctcagaat tgtgggtacg cgaccgtcac ggatagtgtc    420

gctgttgtgg tgcaggccac gccacatcac gtactcgtag atgaatatac tggtgaatgg    480

atcgactccc aattcccgaa tgggaaatgt gagacggaag agtgcgaaac agtgcataac    540

tcaaccgttt ggtattccga ttacaaggtt actggtcttt gcgacgccac cctcgtggat    600

accgagatca cgttttttag tgaggatggc aagaaagagt caataggcaa acctaatact    660

ggctaccgga gtaactattt cgcttacgag aagggtgaca aggtatgtaa aatgaactat    720

tgcaagcatg cgggagtgcg actccccagt ggggtatggt tcgaatttgt tgaccaagac    780
```

-continued

```
gtatacgccg ctgcgaagtt gccagaatgc cccgtaggcg cgaccatttc agcacctacc    840
caaacgtccg ttgacgtctc cttgatactg gatgtagagc gaatcctgga ctacagtctc    900
tgccaggaaa cgtggtcaaa aataagaagt aagcagccag tttcacccgt ggatctgtct    960
tatctggcgc caaaaaaccc gggcacgggc cctgctttta ccataattaa cggaacgctt   1020
aaatacttcg aaacccgcta cattagaatc gatatagaca atcctattat cagcaagatg   1080
gtagggaaga tatctgggtc tcaaacggag gccgaattgt ggacggagtg gttcccttat   1140
gagggagtgg aaattgggcc caacgggatc ctcaagaccc caacgggtta caagttccct   1200
ctgtttatga tcggccatgg catgttggac agtgacttgc acaaaacatc tcaggcagag   1260
gttttcgaac atccacattt ggcggaggcg cccaagcaac ttccagaaga agaaactctc   1320
ttctttggag atacaggcat ttcaaaaaat cctgtagaac tgatagaagg gtggttctct   1380
tcctggaaat caacggttgt cacgtttttc tttgcaatag gcgtatttat actcctgtac   1440
gtcgtagccc gcattgtgat cgcagtacga tacagatacc agggcagtaa caataaacgc   1500
atatataatg acatcgaaat gtcaaggttc cgaaagtga                           1539
```

UNITED STATES PATENT AND TRADEMARK OFFICE
CERTIFICATE OF CORRECTION

| | |
|---|---|
| PATENT NO. | : 12,061,187 B2 |
| APPLICATION NO. | : 16/826665 |
| DATED | : August 13, 2024 |
| INVENTOR(S) | : Michael Birnbaum et al. |

It is certified that error appears in the above-identified patent and that said Letters Patent is hereby corrected as shown below:

In the Claims

At Column 170, Claim 17, Line 58:
"…a PDGFR stalk, a CD8a stalk…"
Should read:
--…a PDGFR stalk, a CD8α stalk…--

Signed and Sealed this
Tenth Day of December, 2024

*Katherine Kelly Vidal*
Katherine Kelly Vidal
*Director of the United States Patent and Trademark Office*